United States Patent [19]
Bard et al.

[11] Patent Number: 5,976,814
[45] Date of Patent: Nov. 2, 1999

[54] DNA ENCODING A HUMAN NEUROPEPTIDE Y/PEPTIDE YY/ PANCREATIC POLYPEPTIDE RECEPTOR (Y4) AND USES THEREOF

[75] Inventors: Jonathan A. Bard, Wyckoff; Mary W. Walker, Elmwood Park; Theresa Branchek; Richard L. Weinshank, both of Teaneck, all of N.J.

[73] Assignee: Synaptic Pharmaceutical Corporation, Paramus, N.J.

[21] Appl. No.: 08/495,695

[22] PCT Filed: Dec. 28, 1994

[86] PCT No.: PCT/US94/14436

§ 371 Date: Jan. 13, 1997

§ 102(e) Date: Jan. 13, 1997

[87] PCT Pub. No.: WO95/17906

PCT Pub. Date: Jul. 6, 1995

Related U.S. Application Data

[63] Continuation-in-part of application No. 08/176,412, Dec. 28, 1993, Pat. No. 5,516,653.

[51] Int. Cl.⁶ .......................... G01N 33/53; C07H 21/04; C12N 15/12; C12N 15/63
[52] U.S. Cl. .................... 435/7.2; 435/69.1; 435/320.1; 435/325; 435/252.3; 435/172.3; 530/350; 530/300
[58] Field of Search .................................... 435/7.2, 69.1, 435/320.1, 325, 252.3, 172.3; 530/350, 300

[56] References Cited

U.S. PATENT DOCUMENTS

| | | | |
|---|---|---|---|
| 4,839,343 | 6/1989 | Waeber et al. | 514/12 |
| 5,026,685 | 6/1991 | Boublik et al. | 514/13 |
| 5,053,337 | 10/1991 | Weinshank et al. | 435/240.2 |
| 5,328,899 | 7/1994 | Boublik et al. | 514/13 |
| 5,506,258 | 4/1996 | Christophe et al. | 514/423 |
| 5,571,695 | 11/1996 | Selbie et al. | 435/69.1 |
| 5,602,024 | 2/1997 | Gerald et al. | 435/325 |

FOREIGN PATENT DOCUMENTS

| | | |
|---|---|---|
| 2037433 | 10/1991 | Canada . |
| 2134428 | 10/1994 | Canada . |
| 0355793 | 2/1990 | European Pat. Off. . |
| 0355794 | 2/1990 | European Pat. Off. . |
| 0356021 | 2/1990 | European Pat. Off. . |
| 6116284 | 4/1994 | Japan . |
| 9200079 | 1/1992 | WIPO . |
| 9309227 | 5/1993 | WIPO . |
| 9324515 | 12/1993 | WIPO . |
| 9400486 | 1/1994 | WIPO . |
| 9422467 | 10/1994 | WIPO . |
| 9500161 | 1/1995 | WIPO . |
| 9614331 | 5/1996 | WIPO . |
| 9623809 | 8/1996 | WIPO . |
| 9717440 | 5/1997 | WIPO . |
| 9737998 | 10/1997 | WIPO . |
| 9748406 | 12/1997 | WIPO . |

OTHER PUBLICATIONS

Herzog, et al. "Cloned Human Neuropeptide Y Receptor Couples to Two Different Second Messenger Systems" *PNAS* (1992) 89(13): 5794–5798.

Larhammar, et al., "Cloning and Functional Expression of a Human Neuropeptide Y/Peptide YY Receptor of the Y1 Type" *The Journal of Biological Chemistry* (1992) 267(16): 10935–10938.

Lundberg, et al., "Comparative Immunohistochemical and Biochemical Analysis of Pancreatic Polypeptide–Like Peptides with Special Reference to Presence of Neuropeptide Y in Central and Peripherial Neurons" *The Journal of Neuroscience* (1984) 4(9): 2376–2386.

Wahlestedt, C., et al., "Identification of Cultured Cells Selectively Expressing Y1–, Y2–, or Y3–Type Receptors for Neuropeptide Y/Peptide YY" *Life Sciences* (1991) 50: P17–PL12.

Wahlestedt, C., et al., "Neuropeptide Y Receptor Subtypes, Y1and Y2" *Annals of the New York Academy of Sciences* (1990) 611: 7–26; and Whitcomb, D.C., et al., "Characterization of Saturable Binding Sites For Circulating Pancreatic Polypeptide In Rat Brain" *Am. J. Physiol.* (1990) 259: G687–G691.

Deferens *Eur. J. Pharm.* (1990) 186: 105–114.

Kotz, C.M., et al., "The Effect of Norbinaltorphimine, β–Funaltrexzmine and Naltrindole on NPY–Induced Feeding" *Brain Research* (1993) 631; 325–328.

Krause, J., et al., "Neuropeptide Y1 Subtype Pharmacology of a Recombinantly Expressed Neuropeptide Receptor" *Mol. Pharm.* (1992) 41: 817–821.

Leibo S.F., et al., "Blockade of Natural and Neuropeptide Y–Induced Carbohydrate Feeding By a Receptor Antagonist PYX –2" *NeuroReport* (1992) 3(11): 1023–1026.

*Patents Abstracts of Japan* (1992) 16(265): Abstract No. C–0951, corresponding to Japanese Patent Application No. 4 063 594, published Feb. 28, 1992.

Schwartz, T.W., et al., "Receptors of Phaechromocytoma Cells For Two Members of the PP–Fold Family–NPY and PP" *FEBS Letters* (1987) 225(1):209–214.

Vander, A.J., et al., *Human Physiology*, McGraw–Hill Publishing Co., (1990) pp. 207–210.

Wahlestedt, C., et al., "Neuropeptide Y–Related Peptides and Their Receptors–Are the Receptors Potential Therapeutic Drug Targets?" *Annu. Rev. Pharmacol. Toxicol.* (1993) 32: 309–352; and.

Weinberg, D.H., et al., "Cloning and Expression of a Novel Neuropeptide Y Receptor" *J. Biol. Chem.* (1996) 271(28): 16435–16438.

(List continued on next page.)

*Primary Examiner*—Paula K. Hutzell
*Assistant Examiner*—Nirmal S. Basi
*Attorney, Agent, or Firm*—John P. White; Cooper & Dunham LLP

[57] ABSTRACT

This invention provides methods for determining whether a chemical compound specifically binds to and activates or inhibits activation of a human or rat Y4 receptor.

10 Claims, 19 Drawing Sheets

OTHER PUBLICATIONS

Bard, J.A., et al., "Cloning and Functional Expression of a Human Y4 Subtype Receptor For Pancreatic Polypeptide, Neuropeptide Y, and Peptide YY" *J. Biol. Chem.* (1995) 270(45): 26762–26765.

Doughty, M.B., et al., "Benextramine–Neuropeptide Y Receptor Interactions : Contribution of the Benzylic Moieties to [$^3$H] Neuropeptide Y Displacement Activity" *J. Med. Chem.* (1993) 36(2): 272–279.

Gehlert, D.R., "Subtypes of Receptors for Neuropeptide Y: Implications for the Targeting of Therapeutics" Life Science (1994) 55(8): 551–562.

George, S.T., et al., "High–Efficiency Expression of Mammalian β –Adrenergic Receptor in Baculovirus–Infected Insect Cells" *Biochemical and Biophysical Research Communications* (1989) 163(3): 1265–1269.

Gerald, C., et al., "A Receptor Subtype Involved in Neuropeptide–Y–Induced Food Intake" *Nature* (1996) 382: 168–171.

Gilbert, W., et al., "Characterization of Specific Pancreatic Polypeptide Receptors on Basolateral Membranes of the Canine Small Intestine" *PNAS* (1988) 85: 4745–4749.

Goadsby, P.J., and Edvinsson, L., "Examination of the Involvement of Neuropeptide Y (NPY) in Cerebral Autoregulation Using the Novel NPY Antagonist PP56" *Neuropeptides* (1993) 24(1): 27–33.

Hu, Y., et al., "Identification of a Novel Hypothalamic Neuropeptide Y Receptor Associated With Feeding Behavior" *Journal of Biological Chemistry* (1996) 271(42): 26315–26319.

Jorgensen, I. Ch., et al., Structure–Function Studies on Neuropeptide Y and Pancreatic Polypeptide–Evidence for Two PP–Fold Receptors in Vas.

FIGURE 1A

| FIGURE 1A |
|-----------|
| FIGURE 1B |
| FIGURE 1C |
| FIGURE 1D |
| FIGURE 1E |

```
         -80                 -60                 -40
-28      AGTATTGTTTGTCTGTGTTTGCCTTGTAGGGGCGTCATCCCTCAAGTGTATCACTTAGTTCAA    31

-20                  -1                  20
 32      GAGTCCTGGAATCTTTTCACATCCCACTATGAACACCCTCTCCACCTCCTGGCCTTGCTGCTC    91
 -8                            M  N  T  S  H  L  L  A  L  L  L         11

40                   60                  80
 92      CCAAAATCTCCACAAGGTGAAAACAGAAGCAAACCCCTGGGCACCCCATACAACTTCTCT    151
 12       P  K  S  P  Q  G  E  N  R  S  K  P  L  G  T  P  Y  N  F  S     31

100                  120                 140
152      GAACATTGCCAGGATTCCGTGGACGTGATGGTCTTCATCGTCACTTCCTACAGCATTGAG    211
 32       E  H  C  Q  D  S  V  D  V  M  V  F  I  V  T  S  Y  S  I  E     51

160                  180                 200
212      ACTGTCGTGGGGGTCCTGGGTAACCTCTGCCTGATGTGTGACTGTGAGGCAGAAGGAG    271
 52       T  V  V  G  V  L  G  N  L  C  L  M  C  V  T  V  R  Q  K  E     71
```

FIGURE 1B

```
            220                 240                 260
272  AAAGCCAACGTGACCAACCTGCTTATCGCCAACCTGGCCTTCTCTGACTTCCTCATGTGC  331
 72   K   A   N   V   T   N   L   L   I   A   N   L   A   F   S   D   F   L   M   C    91

280                 300                 320
332  CTCCTCTGCCAGCCGCTGACCGCTGTCTACACCATCATGGACTACTGGATCTTTGGAGAG  391
 92   L   L   C   Q   P   L   T   A   V   Y   T   I   M   D   Y   W   I   F   G   E   111

340                 360                 380
392  ACCCTCTGCAAGATGTCGGCCTTCATCCAGTGCATGTCGGTGACGGTGTCCATCCTCTCG  451
112   T   L   C   K   M   S   A   F   I   Q   C   M   S   V   T   V   S   I   L   S   131

400                 420                 440
452  CTCGTCCTCGTGGCCCTGGAGAGGCATCAGCTCATCAACCCAACAGGCTGGAAGCCC  511
132   L   V   L   V   A   L   E   R   H   Q   L   I   I   N   P   T   G   W   K   P   151

460                 480                 500
512  AGCATCTCACAGGCCTACCTGGGGATTGTGCTCATCTGGGTCATTGCCTGTGTCCTCTCC  571
152   S   I   S   Q   A   Y   L   G   I   V   L   I   W   V   I   A   C   V   L   S   171
```

FIGURE 1C

```
       520         540         560
572 CTGCCCTTCCTGGCCAACAGCATCCTGGAGAATGTCTTCCACAAGAACCACTCCAAGGCT  631
172  L   P   F   L   A   N   S   I   L   E   N   V   F   H   K   N   H   S   K   A   191

580         600         620
632 CTGGAGTTCCTGGCAGATAAGGTGTCTGTACCGAGTCCTGGCCACTGGCCTCACCCACCGC  691
192  L   E   F   L   A   D   K   V   V   C   T   E   S   W   P   L   A   H   H   R   211

640         660         680
692 ACCATCTACACCACCTTCCTGCTCCTCTTCCAGTACTGCCTCCCACTGGGCTTCATCCTG  751
212  T   I   Y   T   T   F   L   L   L   F   Q   Y   C   L   P   L   G   F   I   L   231

700         720         740
752 GTCTGTTATGCACGCATCTACCGGCGCCTGCAGAGGCAGGGGCGTGTTTCACAAGGGC  811
232  V   C   Y   A   R   I   Y   R   R   L   Q   R   Q   G   R   V   F   H   K   G   251

760         780         800
812 ACCTACAGCTTGCGAGCTGGGCACATGAAGCAGGTCAATGTTGTCCTGGTGGTGATGGTG  871
252  T   Y   S   L   R   A   G   H   M   K   Q   V   N   V   V   L   V   V   M   V   271
```

FIGURE 1D

```
       820                840                860
872  GTGGCCTTTGCCGTGCTCTGGCTGCCTCTGCATGTGTTCAACAGCCTGGAAGACTGGCAC  931
272   V  A  F  A  V  L  W  L  P  L  H  V  F  N  S  L  E  D  W  H   291

880                900                920
932  CATGAGGCCATCCCCATCTGCCACGGGAACCCTCATCTTCTTAGTGTGCCACTTGCTTGCC  991
292   H  E  A  I  P  I  C  H  G  N  L  I  F  L  V  C  H  L  L  A   311

940                960                980
992  ATGGCCTCCACCTGCGTCAACCCATTCATCTATGGCTTTCTCAACACCAACTTCAAGAAG  1051
312   M  A  S  T  C  V  N  P  F  I  Y  G  F  L  N  T  N  F  K  K   331

1000               1020               1040
1052 GAGATCAAGGCCCTGGTGCTGACTTGCCAGCAGAGCGCCCCCCTGGAGGAGTCGGAGCAT  1111
332   E  I  K  A  L  V  L  T  C  Q  Q  S  A  P  L  E  E  S  E  H   351

1060               1080               1100
1112 CTGCCCCTGTCCACAGTACATACGGAAGTCTCCAAAGGGTCCCTGAGGCTAAGTGGCAGG  1171
352   L  P  L  S  T  V  H  T  E  V  S  K  G  S  L  R  L  S  G  R   371
```

FIGURE 1E

```
1172        1120               1140              1160
     TCCAATCCCATTTAACCAGGTCTAGGTCTCTTCCCCTGCCATGTCCCTTGCCAGGCTCTTC   1231
372   S   N   P   I   *                                             375

1232        1180              1200               1220
     CACTTAGCTAAGTGGGCACACTGCAAGCTGGGGTGGCACCCCAGCATTCCTGGCTTTCTG    1291
```

FIGURE 2A

| | FIGURE 2A |
|---|---|
| | FIGURE 2B |
| | FIGURE 2C |

```
                                                                              50
       1
hp25a      MNTSHLLALL LPKSPQGENR SKPLGTPYNF SEHCQDSVDV MVFIVTSYSI
human Y1   MN.STLFSQV ENHSVHSNFS EKNAQLLAFE NDDCHLPLAM IFTLALAYGA
rat Y1     MN.STLFSRV ENYSVHYNVS E.NSPFLAFE NDDCHLPLAV IFTLALAYGA
mouse Y1   MN.STLFSKV ENHSIHYNAS E.NSPLLAFE NDDCHLPLAV IFTLALAYGA I                                             II
       51                                                                    100
hp25a      ETVVGVLGNL CLMCVTVRQK EKANVTNLII ANLAFSDFLM CLLCQPLTAV
human Y1   VIILGVSGNL ALIIIILKQK EMRNVTNILI VNLSFSDLLV AIMCLPFTFV
rat Y1     VIILGVSGNL ALIIIILKQK EMRNVTNILI VNLSFSDLLV AVMCLPFTFV
mouse Y1   VIILGVSGNL ALIIIILKQK EMRNVTNILI VNLSFSDLIV AVMCLPFTFV III
       101                                                                   150
hp25a      YTIMDYWIFG ETLCKMSAFI QCMSVTVSIL SLVLVALERH QLIINPTGWK
human Y1   YTLMDHWVFG EAMCKLNPFV QCVSITVSIF SLVLIAVERH QLIINPRGWR
rat Y1     YTLMDHWVFG ETMCKLNPFV QCVSITVSIF SLVLIAVERH QLIINPRGWR
mouse Y1   YTLMDHWVFG ETMCKLNPFV QCVSITVSIF SLVLIAVERH QLIINPRGWR IV
       151                                                                   200
hp25a      PSISQAYLGI VLIWVIACVL SLPFLANSIL ENVFHKNHSK ALEFLADKVV
human Y1   PNNRHAYVGI AVIWVLAVAS SLPFLIYQVM TDEPFQNVT. .LDAYKDKYV
rat Y1     PNNRHAYIGI TVIWVLAVAS SLPFVIYQIL TDEPFQNVS. .LAAFKDKYV
mouse Y1   PNNRHAYIGI TVIWVLAVAS SLPFVIYQIL TDEPFQNVS. .LAAFKDKYV
```

FIGURE 2B

```
                                                                              250
         201                                                    V
hp25a    CTESWPLAHH  RTIYTTFLIL  FQYCLPLGFI  LVCYARTYRR  LQRQGRVFHK
human Y1 CFDQFPSDSH  RLSYTTLLEV  LQYFGPLCFI  FICYFKIYIR  LKRRNNMMDK
rat Y1   CFDKFPSDSH  RLSYTTLLEV  LQYFGPLCFI  FICYFKIYIR  LKRRNNMMDK
mouse Y1 CFDKFPSDSH  RLSYTTLLEV  LQYFGPLCFI  FICYFKIYIR  LKRRNNMMDK 300
         251                                                    VI
hp25a    GTYS.LRAGH  MKQVNVVLVV  MVVAFAVLWL  PLHVFNSLED  WHHEAIPICH
human Y1 MRDNKYRSSE  TKRINIMLLS  IVVAFAVCWL  PLTIFNTVFD  WNHQIIATCN
rat Y1   IRDSKYRSSE  TKRINVMLLS  IVVAFAVCWL  PLTIFNTVFD  WNHQIIATCN
mouse Y1 IRDSKYRSSE  TKRINIMLLS  IVVAFAVCWL  PLTIFNTVFD  WNHQIIATCN VII                                             350
         301
hp25a    GNLIFIVCHL  LAMASTCVNP  FIYGFLNTNF  KKEIKALVLT  CQQSAPLEES
human Y1 HNLFFLCHL   TAMISTCVNP  IFYGFLNKNF  QRDLQFFFNF  CDFRSRDDDY
rat Y1   HNLFFLCHL   TAMISTCVNP  IFYGFLNKNF  QRDLQFFFNF  CDFRSRDDDY
mouse Y1 HNLFFLCHL   TAMISTCVNP  IFYGFLNKNF  QRDLQFFFNF  CDFRSRDDDY
```

FIGURE 2C

```
          351                                              388
hp25a     EHLPLSTVHT EVSKGSLRLS GRSNPI*.... .........
human Y1  ETIAMSTMHT DVSKTSLKQA SPVAFKKINN NDDNEKI*
rat Y1    ETIAMSTMHT DVSKTSLKQA SPVAFKKISM N.DNEKI*
mouse Y1  ETIAMSTMHT DVSKTSLKQA SPVAFKKISM N.DNEKV*
```

FIGURE 3A

| FIGURE 3A |
|-----------|
| FIGURE 3B |
| FIGURE 3C |
| FIGURE 3D |

```
        -170              -150              -130
          .         .       .        .        .        .
ATAGCTCTCAAGCCATAAGATATAAGTAGCTAAGAATTGTCTCCCTCTCCCTGTCCCTTG

-110               -90               -70
          .         .       .        .        .        .
TTCTTACCTGGTTCCATTTTACATGCCTGGACCTTTGAGTTCCATTTGTTTGTTTTGCAG

-50               -30               -10
          .         .       .        .        .        .
GCTACACTCAGAAGTGGGCCCTTTAGTCTTGAAGTTCCTGGTCTTCTCACACCCACCATG
                                                            M 10                30                50
          .         .       .        .        .        .
AATACCTCTCATCTCATGGCCTCCCTTTCTCCGGCATTCCTACAAGGTAAGAATGGGACC
 N  T  S  H  L  M  A  S  L  S  P  A  F  L  Q  G  K  N  G  T 70                90               110
          .         .       .        .        .        .
AACCCACTGGATTCCCTCTATAATCTCTCTGACGGCTGCCAGGATTCGGCAGATCTGTTG
 N  P  L  D  S  L  Y  N  L  S  D  G  C  Q  D  S  A  D  L  L 130               150               170
          .         .       .        .        .        .
GCCTTCATCATCACCACCTACAGCGTTGAGACCGTCTTGGGGGTCCTAGGAAACCTCTGC
 A  F  I  I  T  T  Y  S  V  E  T  V  L  G  V  L  G  N  L  C 190               210               230
          .         .       .        .        .        .
TTGATATTTGTGACCACAAGGCAAAAGGAAAAGTCCAATGTGACCAACCTACTCATTGCC
 L  I  F  V  T  T  R  Q  K  E  K  S  N  V  T  N  L  L  I  A
```

FIGURE 3B

```
          250                    270                    290
AACCTGGCCTTCTCTGACTTCCTCATGTGTCTCATCTGCCAGCCGCTCACGGTCACCTAC
 N  L  A  F  S  D  F  L  M  C  L  I  C  Q  P  L  T  V  T  Y 310                    330                    350
ACCATCATGGACTACTGGATCTTCGGCGAAGTCCTTTGCAAGATGTTAACGTTCATCCAG
 T  I  M  D  Y  W  I  F  G  E  V  L  C  K  M  L  T  F  I  Q 370                    390                    410
TGTATGTCGGTGACAGTCTCCATCCTCTCACTGGTCCTTGTGGCCCTGGAGAGGCACCAG
 C  M  S  V  T  V  S  I  L  S  L  V  L  V  A  L  E  R  H  Q 430                    450                    470
CTCATTATCAACCCGACTGGCTGGAAACCCAGCATTTCCCAGGCCTACCTGGGGATTGTG
 L  I  I  N  P  T  G  W  K  P  S  I  S  Q  A  Y  L  G  I  V 490                    510                    530
GTCATCTGGTTCATTTCTTGTTTCCTCTCCTTGCCCTTCCTGGCCAATAGCATCCTGAAC
 V  I  W  F  I  S  C  F  L  S  L  P  F  L  A  N  S  I  L  N 550                    570                    590
GACCTCTTCCACTACAACCACTCTAAGGTTGTGGAGTTTCTGGAAGACAAGGTTGTCTGC
 D  L  F  H  Y  N  H  S  K  V  V  E  F  L  E  D  K  V  V  C 610                    630                    650
TTTGTGTCCTGGTCCTCGGATCACCACCGCCTCATCTACACCACCTTTCTGCTGCTCTTC
 F  V  S  W  S  S  D  H  H  R  L  I  Y  T  T  F  L  L  F
```

FIGURE 3C

```
           670                    690                     710
            .                      .                       .
CAATACTGCGTCCCTCTGGCCTTCATCCTGGTCTGCTACATGCGTATCTATCAGCGCCTG
 Q  Y  C  V  P  L  A  F  I  L  V  C  Y  M  R  I  Y  Q  R  L 730                    750                     770
            .                      .                       .
CAGAGGCAGAGGCGTGCGTTCCACACGCACACTTGCAGCTCACGAGTGGGGCAGATGAAG
 Q  R  Q  R  R  A  F  H  T  H  T  C  S  S  R  V  G  Q  M  K 790                    810                     830
            .                      .                       .
CGGATCAATGGCATGCTCATGGCAATGGTGACTGCCTTTGCAGTTCTCTGGCTGCCCCTG
 R  I  N  G  M  L  M  A  M  V  T  A  F  A  V  L  W  L  P  L 850                    870                     890
            .                      .                       .
CATGTGTTCAACACTCTGGAGGACTGGTACCAGGAAGCCATCCCTGCTTGCCATGGCAAC
 H  V  F  N  T  L  E  D  W  Y  Q  E  A  I  P  A  C  H  G  N 910                    930                     950
            .                      .                       .
CTCATCTTCTTGATGTGCCACCTGTTTGCCATGGCTTCCACCTGTGTCAACCCTTTCATC
 L  I  F  L  M  C  H  L  F  A  M  A  S  T  C  V  N  P  F  I 970                    990                    1010
            .                      .                       .
TATGGCTTTCTCAACATCAACTTCAAGAAGGACATCAAGGCTCTGGTTCTGACCTGCCGT
 Y  G  F  L  N  I  N  F  K  K  D  I  K  A  L  V  L  T  C  R 1030                   1050                    1070
            .                      .                       .
TGCAGGCCACCTCAAGGGGAGCCTGAGCCTCTGCCCCTGTCCACTGTGCACACGGACCTC
 C  R  P  P  Q  G  E  P  E  P  L  P  L  S  T  V  H  T  D  L
```

FIGURE 3D

```
         1090                    1110                    1130
           .                       .                       .
TCCAAGGGATCTATGAGGATGGGTAGCAAGTCTAACGTCATGTAGTCATGTCTAGGCTCT
 S  K  G  S  M  R  M  G  S  K  S  N  V  M  *

1150                    1170                    1190
           .                       .                       .
TCCGCCATTTTCTTTCGACACACCCTTTCACTGAGCTAAGTAGACACAATGCAAGCTGTG 1210                    1230                    1250
           .                       .                       .
GTATCATCCTGCCATTTCTGGTCTTTGGGGCCCAGACAGGCGGCAAGAGACTTGAAGCTT
```

FIGURE 4

```
              1                                                          50
                                                      ┌─────────────────
Y4rat    MNTSHLMASL  SPAFLQGKNG  TNPLDSLYNL  SDGCQDSADL  LAFIITTYSV
Y4hum    MNTSHLLALL  LPKSPQGENR  SKPLGTPYNF  SEHCQDSVDV  MVFIVTSYSI 51                                                         100
         ─── I ──────────────┐              ┌───────────── II ──────
Y4rat    ETVLGVLGNL  CLIFVTTRQK  EKSNVTNLLI  ANLAFSDFLM  CLICQPLTVT
Y4hum    ETVVGVLGNL  CLMCVTVRQK  EKANVTNLLI  ANLAFSDFLM  CLLCQPLTAV 101                                                        150
         ──┐              ┌───────── III ─────────┐
Y4rat    YTIMDYWIFG  EVLCKMLTFI  QCMSVTVSIL  SLVLVALERH  QLIINPTGWK
Y4hum    YTIMDYWIFG  ETLCKMSAPI  QCMSVTVSIL  SLVLVALERH  QLIINPTGWK 151                                                        200
                     ┌───────── IV ─────────┐
Y4rat    PSISQAYLGI  VVIWFISCFL  SLPFLANSIL  NDLFHYNHSK  VVEFLEDKVV
Y4hum    PSISQAYLGI  VLIWVIACVL  SLPFLANSIL  ENVFHKNHSK  ALEFLADKVV 201                                                        250
                             ┌───────── V ─────────┐
Y4rat    CFVSWSSDHH  RLIYTTFLLL  PQYCVPLAFI  LVCYMRIYQR  LQRQRRAFHT
Y4hum    CTESWPLAHH  RTIYTTFLLL  PQYCLPLGFI  LVCYARIYRR  LQRQGRVFHK 251                                                        300
                             ┌───────── VI ─────────┐
Y4rat    HTCSSRVGQM  KRINGMLMAM  VTAPAVLWLP  LHVFNTLEDW  YQEAIPACHG
Y4hum    GTYSLRAGHM  KQVNVVLVVM  VVAFAVLWLP  LHVFNSLEDW  HHEAIPICHG 301                                                        350
                  ┌───────── VII ─────────┐
Y4rat    NLIFLMCHLP  AMASTCVNPF  IYGFLNINFK  KDIKALVLTC  RCRPPQGEPE
Y4hum    NLIFLVCHLL  AMASTCVNPF  IYGFLNTNFK  KEIKALVLTC  QQSAPLEESE
```

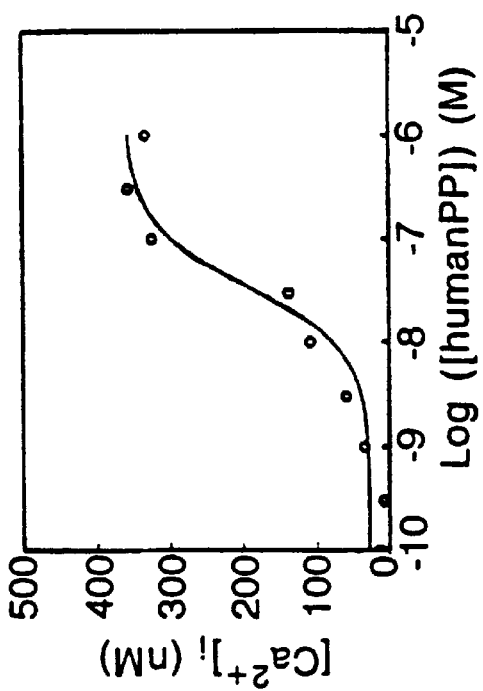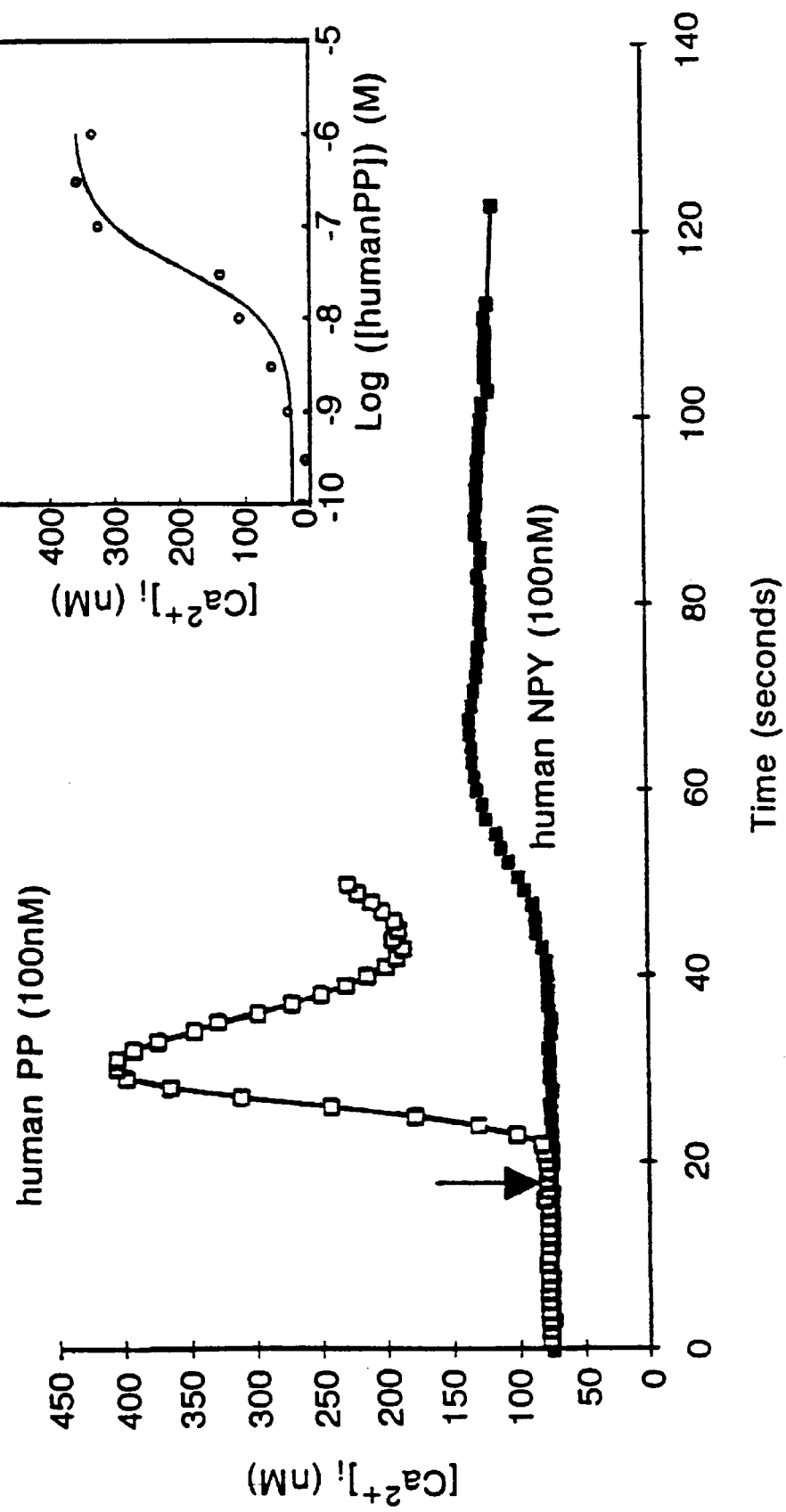

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 1320 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 88..1212

(xi) SEQUENCE DESCRIPTION: SEQ ID NO:1:

```
AGTATTGTTT GTCTGTTTGC CTTGTAGGGC GTCATCCCTC AAGTGTATCA CTTAGTTCAA          60

GAGTCCTGGA ATCTTTTCAC ATCCACT ATG AAC ACC TCT CAC CTC CTG GCC            111
                              Met Asn Thr Ser His Leu Leu Ala
                                1               5

TTG CTG CTC CCA AAA TCT CCA CAA GGT GAA AAC AGA AGC AAA CCC CTG          159
Leu Leu Leu Pro Lys Ser Pro Gln Gly Glu Asn Arg Ser Lys Pro Leu
         10              15                  20

GGC ACC CCA TAC AAC TTC TCT GAA CAT TGC CAG GAT TCC GTG GAC GTG          207
Gly Thr Pro Tyr Asn Phe Ser Glu His Cys Gln Asp Ser Val Asp Val
 25              30                  35                  40

ATG GTC TTC ATC GTC ACT TCC TAC AGC ATT GAG ACT GTC GTG GGG GTC          255
Met Val Phe Ile Val Thr Ser Tyr Ser Ile Glu Thr Val Val Gly Val
                 45                  50                  55

CTG GGT AAC CTC TGC CTG ATG TGT GTG ACT GTG AGG CAG AAG GAG AAA          303
Leu Gly Asn Leu Cys Leu Met Cys Val Thr Val Arg Gln Lys Glu Lys
                 60                  65                  70

GCC AAC GTG ACC AAC CTG CTT ATC GCC AAC CTG GCC TTC TCT GAC TTC          351
Ala Asn Val Thr Asn Leu Leu Ile Ala Asn Leu Ala Phe Ser Asp Phe
         75                  80                  85

CTC ATG TGC CTC CTC TGC CAG CCG CTG ACC GCC GTC TAC ACC ATC ATG          399
Leu Met Cys Leu Leu Cys Gln Pro Leu Thr Ala Val Tyr Thr Ile Met
         90                  95                 100

GAC TAC TGG ATC TTT GGA GAG ACC CTC TGC AAG ATG TCG GCC TTC ATC          447
```

```
Asp Tyr Trp Ile Phe Gly Glu Thr Leu Cys Lys Met Ser Ala Phe Ile
105                 110                 115                 120

CAG TGC ATG TCG GTG ACG GTC TCC ATC CTC TCG CTC GTC CTC GTG GCC        495
Gln Cys Met Ser Val Thr Val Ser Ile Leu Ser Leu Val Leu Val Ala
                125                 130                 135

CTG GAG AGG CAT CAG CTC ATC ATC AAC CCA ACA GGC TGG AAG CCC AGC        543
Leu Glu Arg His Gln Leu Ile Ile Asn Pro Thr Gly Trp Lys Pro Ser
                140                 145                 150

ATC TCA CAG GCC TAC CTG GGG ATT GTG CTC ATC TGG GTC ATT GCC TGT        591
Ile Ser Gln Ala Tyr Leu Gly Ile Val Leu Ile Trp Val Ile Ala Cys
                155                 160                 165

GTC CTC TCC CTG CCC TTC CTG GCC AAC AGC ATC CTG GAG AAT GTC TTC        639
Val Leu Ser Leu Pro Phe Leu Ala Asn Ser Ile Leu Glu Asn Val Phe
        170                 175                 180

CAC AAG AAC CAC TCC AAG GCT CTG GAG TTC CTG GCA GAT AAG GTG GTC        687
His Lys Asn His Ser Lys Ala Leu Glu Phe Leu Ala Asp Lys Val Val
185                 190                 195                 200

TGT ACC GAG TCC TGG CCA CTG GCT CAC CAC CGC ACC ATC TAC ACC ACC        735
Cys Thr Glu Ser Trp Pro Leu Ala His His Arg Thr Ile Tyr Thr Thr
                205                 210                 215

TTC CTG CTC CTC TTC CAG TAC TGC CTC CCA CTG GGC TTC ATC CTG GTC        783
Phe Leu Leu Leu Phe Gln Tyr Cys Leu Pro Leu Gly Phe Ile Leu Val
                220                 225                 230

TGT TAT GCA CGC ATC TAC CGG CGC CTG CAG AGG CAG GGG CGC GTG TTT        831
Cys Tyr Ala Arg Ile Tyr Arg Arg Leu Gln Arg Gln Gly Arg Val Phe
            235                 240                 245

CAC AAG GGC ACC TAC AGC TTG CGA GCT GGG CAC ATG AAG CAG GTC AAT        879
His Lys Gly Thr Tyr Ser Leu Arg Ala Gly His Met Lys Gln Val Asn
            250                 255                 260

GTG GTG CTG GTG GTG ATG GTG GTG GCC TTT GCC GTG CTC TGG CTG CCT        927
Val Val Leu Val Val Met Val Val Ala Phe Ala Val Leu Trp Leu Pro
265                 270                 275                 280

CTG CAT GTG TTC AAC AGC CTG GAA GAC TGG CAC CAT GAG GCC ATC CCC        975
Leu His Val Phe Asn Ser Leu Glu Asp Trp His His Glu Ala Ile Pro
                285                 290                 295

ATC TGC CAC GGG AAC CTC ATC TTC TTA GTG TGC CAC TTG CTT GCC ATG       1023
Ile Cys His Gly Asn Leu Ile Phe Leu Val Cys His Leu Leu Ala Met
            300                 305                 310

GCC TCC ACC TGC GTC AAC CCA TTC ATC TAT GGC TTT CTC AAC ACC AAC       1071
Ala Ser Thr Cys Val Asn Pro Phe Ile Tyr Gly Phe Leu Asn Thr Asn
            315                 320                 325

TTC AAG AAG GAG ATC AAG GCC CTG GTG CTG ACT TGC CAG CAG AGC GCC       1119
Phe Lys Lys Glu Ile Lys Ala Leu Val Leu Thr Cys Gln Gln Ser Ala
        330                 335                 340

CCC CTG GAG GAG TCG GAG CAT CTG CCC CTG TCC ACA GTA CAT ACG GAA       1167
Pro Leu Glu Glu Ser Glu His Leu Pro Leu Ser Thr Val His Thr Glu
345                 350                 355                 360

GTC TCC AAA GGG TCC CTG AGG CTA AGT GGC AGG TCC AAT CCC ATT           1212
Val Ser Lys Gly Ser Leu Arg Leu Ser Gly Arg Ser Asn Pro Ile
                365                 370                 375

TAACCAGGTC TAGGTCTTCT CCCTGCCATG TCCCTTGCCA GGCTCTTCCA CTTAGCTAAG     1272

TGGGCACACT GCAAGCTGGG GTGGCACCCC AGCATTCCTG GCTTTCTG                 1320

(2) INFORMATION FOR SEQ ID NO:2:

(i) SEQUENCE CHARACTERISTICS:
        (A) LENGTH: 375 amino acids
        (B) TYPE: amino acid
        (D) TOPOLOGY: linear (ii) MOLECULE TYPE: protein
```

(xi) SEQUENCE DESCRIPTION: SEQ ID NO:2:

```
Met Asn Thr Ser His Leu Leu Ala Leu Leu Leu Pro Lys Ser Pro Gln
 1               5                  10                  15

Gly Glu Asn Arg Ser Lys Pro Leu Gly Thr Pro Tyr Asn Phe Ser Glu
             20                  25                  30

His Cys Gln Asp Ser Val Asp Val Met Val Phe Ile Val Thr Ser Tyr
         35                  40                  45

Ser Ile Glu Thr Val Val Gly Val Leu Gly Asn Leu Cys Leu Met Cys
     50                  55                  60

Val Thr Val Arg Gln Lys Glu Lys Ala Asn Val Thr Asn Leu Leu Ile
 65                  70                  75                  80

Ala Asn Leu Ala Phe Ser Asp Phe Leu Met Cys Leu Leu Cys Gln Pro
                 85                  90                  95

Leu Thr Ala Val Tyr Thr Ile Met Asp Tyr Trp Ile Phe Gly Glu Thr
            100                 105                 110

Leu Cys Lys Met Ser Ala Phe Ile Gln Cys Met Ser Val Thr Val Ser
        115                 120                 125

Ile Leu Ser Leu Val Leu Val Ala Leu Glu Arg His Gln Leu Ile Ile
130                 135                 140

Asn Pro Thr Gly Trp Lys Pro Ser Ile Ser Gln Ala Tyr Leu Gly Ile
145                 150                 155                 160

Val Leu Ile Trp Val Ile Ala Cys Val Leu Ser Leu Pro Phe Leu Ala
                165                 170                 175

Asn Ser Ile Leu Glu Asn Val Phe His Lys Asn His Ser Lys Ala Leu
            180                 185                 190

Glu Phe Leu Ala Asp Lys Val Val Cys Thr Glu Ser Trp Pro Leu Ala
        195                 200                 205

His His Arg Thr Ile Tyr Thr Thr Phe Leu Leu Leu Phe Gln Tyr Cys
210                 215                 220

Leu Pro Leu Gly Phe Ile Leu Val Cys Tyr Ala Arg Ile Tyr Arg Arg
225                 230                 235                 240

Leu Gln Arg Gln Gly Arg Val Phe His Lys Gly Thr Tyr Ser Leu Arg
                245                 250                 255

Ala Gly His Met Lys Gln Val Asn Val Val Leu Val Val Met Val Val
            260                 265                 270

Ala Phe Ala Val Leu Trp Leu Pro Leu His Val Phe Asn Ser Leu Glu
        275                 280                 285

Asp Trp His His Glu Ala Ile Pro Ile Cys His Gly Asn Leu Ile Phe
290                 295                 300

Leu Val Cys His Leu Leu Ala Met Ala Ser Thr Cys Val Asn Pro Phe
305                 310                 315                 320

Ile Tyr Gly Phe Leu Asn Thr Asn Phe Lys Lys Glu Ile Lys Ala Leu
                325                 330                 335

Val Leu Thr Cys Gln Gln Ser Ala Pro Leu Glu Glu Ser Glu His Leu
            340                 345                 350

Pro Leu Ser Thr Val His Thr Glu Val Ser Lys Gly Ser Leu Arg Leu
        355                 360                 365

Ser Gly Arg Ser Asn Pro Ile
370                 375
```

(2) INFORMATION FOR SEQ ID NO:3:

(i) SEQUENCE CHARACTERISTICS:
        (A) LENGTH: 45 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

TTGCTTATGG GGCTGTGATT ATTCTTGGGG TCTCTGGAAA CCTGG                45

(2) INFORMATION FOR SEQ ID NO:4:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:4:

TAGGATGATT ATGATCAATG CCAGGTTTCC AGAGACCCCA AGAAT                45

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

AAAGAGATGA GGAATGTCAC CAACATTCTG ATCGTGAACC TCTCC                45

(2) INFORMATION FOR SEQ ID NO:6:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:6:

CAGCAAGTCT GAGAAGGAGA GGTTCACGAT CAGAATGTTG GTGAC                45

(2) INFORMATION FOR SEQ ID NO:7:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

TGCAAACTGA ATCCTTTTGT GCAATGCGTC TCCATTACAG TATCCATTTT CTCT          54

(2) INFORMATION FOR SEQ ID NO:8:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:8:

ACGTTCCACA GCGATGAGAA CCAGAGAGAA AATGGATACT GTAATGGAGA CGCA          54

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

CTGCAGTATT TTGGCCCACT CTGTTTCATA TTCATATGCT AC          42

(2) INFORMATION FOR SEQ ID NO:10:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:10:

CAAGCGAATG TATATCTTGA AGTAGCATAT GAATATGAAA CA          42

(2) INFORMATION FOR SEQ ID NO:11:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

CTGCTCTGCC ACCTCACGGC CATGATCTCC ACCTGCGTCA ACCCCATC         48

(2) INFORMATION FOR SEQ ID NO:12:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:12:

GAAATTTTTG TTCAGGAATC CATAAAAGAT GGGGTTGACG CAGGTGGA         48

(2) INFORMATION FOR SEQ ID NO:13:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

TCATCGTCAC TTCCTACAGC ATTGAGACTG TCGTGGGGGT CCTGGGT          47

(2) INFORMATION FOR SEQ ID NO:14:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

ACAGTCACAC ACATCAGGCA GAGGTTACCC AGGACCCCCA CGACAG           46

(2) INFORMATION FOR SEQ ID NO:15:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

TGCTTATCGC CAACCTGGCC TTCTCTGACT TCCTCATGTG CCTCC                    45

(2) INFORMATION FOR SEQ ID NO:16:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

TAGACGGCGG TCAGCGGCTG GCAGAGGAGG CACATGAGGA AGTCA                    45

(2) INFORMATION FOR SEQ ID NO:17:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

TGTCGGCCTT CATCCAGTGC ATGTCGGTGA CGGTCTCCAT CCTCT                    45

(2) INFORMATION FOR SEQ ID NO:18:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

CTCTCCAGGG CCACGAGGAC GAGCGAGAGG ATGGAGACCG TCACC                    45

(2) INFORMATION FOR SEQ ID NO:19:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

GCCTACCTGG GGATTGTGCT CATCTGGGTC ATTGCCTGTG TCCTC                    45

(2) INFORMATION FOR SEQ ID NO:20:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

TGCTGTTGGC CAGGAAGGGC AGGGAGAGGA CACAGGCAAT GACCC                45

(2) INFORMATION FOR SEQ ID NO:21:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

CATCTACACC ACCTTCCTGC TCCTCTTCCA GTACTGCCTC CCACT                45

(2) INFORMATION FOR SEQ ID NO:22:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

TGCATAACAG ACCAGGATGA AGCCCAGTGG GAGGCAGTAC TGGAA                45

(2) INFORMATION FOR SEQ ID NO:23:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

CTGGTGGTGA TGGTGGTGGC CTTTGCCGTG CTCTGGCTGC CTCTGC               46

(2) INFORMATION FOR SEQ ID NO:24:

(i) SEQUENCE CHARACTERISTICS:
            (A) LENGTH: 45 base pairs
            (B) TYPE: nucleic acid

```
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

CAGTCTTCCA GGCTGTTGAA CACATGCAGA GGCAGCCAGA GCACG                       45

(2) INFORMATION FOR SEQ ID NO:25:

(i) SEQUENCE CHARACTERISTICS:
          (A) LENGTH: 45 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

ATCTTCTTAG TGTGCCACTT GCTTGCCATG GCCTCCACCT GCGTC                       45

(2) INFORMATION FOR SEQ ID NO:26:

(i) SEQUENCE CHARACTERISTICS:
          (A) LENGTH: 45 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

TGAGAAAGCC ATAGATGAAT GGGTTGACGC AGGTGGAGGC CATGG                       45

(2) INFORMATION FOR SEQ ID NO:27:

(i) SEQUENCE CHARACTERISTICS:
          (A) LENGTH: 1439 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (ix) FEATURE:
          (A) NAME/KEY: CDS
          (B) LOCATION: 178..1306

(xi) SEQUENCE DESCRIPTION: SEQ ID NO:27:

ATAGCTCTCA AGCCATAAGA TATAAGTAGC TAAGAATTGT CTCCCTCTCC CTGTCCCTTG        60

TTCTTACCTG GTTCCATTTT ACATGCCTGG ACCTTTGAGT TCCATTTGTT TGTTTTGCAG       120

GCTACACTCA GAAGTGGGCC CTTTAGTCTT GAAGTTCCTG GTCTTCTCAC ACCCACC          177

ATG AAT ACC TCT CAT CTC ATG GCC TCC CTT TCT CCG GCA TTC CTA CAA         225
Met Asn Thr Ser His Leu Met Ala Ser Leu Ser Pro Ala Phe Leu Gln
```

```
              1                   5                  10                  15
GGT AAG AAT GGG ACC AAC CCA CTG GAT TCC CTC TAT AAT CTC TCT GAC       273
Gly Lys Asn Gly Thr Asn Pro Leu Asp Ser Leu Tyr Asn Leu Ser Asp
                      20                  25                  30

GGC TGC CAG GAT TCG GCA GAT CTG TTG GCC TTC ATC ATC ACC ACC TAC       321
Gly Cys Gln Asp Ser Ala Asp Leu Leu Ala Phe Ile Ile Thr Thr Tyr
             35                  40                  45

AGC GTT GAG ACC GTC TTG GGG GTC CTA GGA AAC CTC TGC TTG ATA TTT       369
Ser Val Glu Thr Val Leu Gly Val Leu Gly Asn Leu Cys Leu Ile Phe
         50                  55                  60

GTG ACC ACA AGG CAA AAG GAA AAG TCC AAT GTG ACC AAC CTA CTC ATT       417
Val Thr Thr Arg Gln Lys Glu Lys Ser Asn Val Thr Asn Leu Leu Ile
 65                  70                  75                  80

GCC AAC CTG GCC TTC TCT GAC TTC CTC ATG TGT CTC ATC TGC CAG CCG       465
Ala Asn Leu Ala Phe Ser Asp Phe Leu Met Cys Leu Ile Cys Gln Pro
                 85                  90                  95

CTC ACG GTC ACC TAC ACC ATC ATG GAC TAC TGG ATC TTC GGC GAA GTC       513
Leu Thr Val Thr Tyr Thr Ile Met Asp Tyr Trp Ile Phe Gly Glu Val
            100                 105                 110

CTT TGC AAG ATG TTA ACG TTC ATC CAG TGT ATG TCG GTG ACA GTC TCC       561
Leu Cys Lys Met Leu Thr Phe Ile Gln Cys Met Ser Val Thr Val Ser
        115                 120                 125

ATC CTC TCA CTG GTC CTT GTG GCC CTG GAG AGG CAC CAG CTC ATT ATC       609
Ile Leu Ser Leu Val Leu Val Ala Leu Glu Arg His Gln Leu Ile Ile
130                 135                 140

AAC CCG ACT GGC TGG AAA CCC AGC ATT TCC CAG GCC TAC CTG GGG ATT       657
Asn Pro Thr Gly Trp Lys Pro Ser Ile Ser Gln Ala Tyr Leu Gly Ile
145                 150                 155                 160

GTG GTC ATC TGG TTC ATT TCT TGT TTC CTC TCC TTG CCC TTC CTG GCC       705
Val Val Ile Trp Phe Ile Ser Cys Phe Leu Ser Leu Pro Phe Leu Ala
                165                 170                 175

AAT AGC ATC CTG AAC GAC CTC TTC CAC TAC AAC CAC TCT AAG GTT GTG       753
Asn Ser Ile Leu Asn Asp Leu Phe His Tyr Asn His Ser Lys Val Val
            180                 185                 190

GAG TTT CTG GAA GAC AAG GTT GTC TGC TTT GTG TCC TGG TCC TCG GAT       801
Glu Phe Leu Glu Asp Lys Val Val Cys Phe Val Ser Trp Ser Ser Asp
        195                 200                 205

CAC CAC CGC CTC ATC TAC ACC ACC TTT CTG CTG CTC TTC CAA TAC TGC       849
His His Arg Leu Ile Tyr Thr Thr Phe Leu Leu Leu Phe Gln Tyr Cys
210                 215                 220

GTC CCT CTG GCC TTC ATC CTG GTC TGC TAC ATG CGT ATC TAT CAG CGC       897
Val Pro Leu Ala Phe Ile Leu Val Cys Tyr Met Arg Ile Tyr Gln Arg
225                 230                 235                 240

CTG CAG AGG CAG AGG CGT GCG TTC CAC ACG CAC ACT TGC AGC TCA CGA       945
Leu Gln Arg Gln Arg Arg Ala Phe His Thr His Thr Cys Ser Ser Arg
                245                 250                 255

GTG GGG CAG ATG AAG CGG ATC AAT GGC ATG CTC ATG GCA ATG GTG ACT       993
Val Gly Gln Met Lys Arg Ile Asn Gly Met Leu Met Ala Met Val Thr
            260                 265                 270

GCC TTT GCA GTT CTC TGG CTG CCC CTG CAT GTG TTC AAC ACT CTG GAG       1041
Ala Phe Ala Val Leu Trp Leu Pro Leu His Val Phe Asn Thr Leu Glu
        275                 280                 285

GAC TGG TAC CAG GAA GCC ATC CCT GCT TGC CAT GGC AAC CTC ATC TTC       1089
Asp Trp Tyr Gln Glu Ala Ile Pro Ala Cys His Gly Asn Leu Ile Phe
    290                 295                 300

TTG ATG TGC CAC CTG TTT GCC ATG GCT TCC ACC TGT GTC AAC CCT TTC       1137
Leu Met Cys His Leu Phe Ala Met Ala Ser Thr Cys Val Asn Pro Phe
305                 310                 315                 320

ATC TAT GGC TTT CTC AAC ATC AAC TTC AAG AAG GAC ATC AAG GCT CTG       1185
Ile Tyr Gly Phe Leu Asn Ile Asn Phe Lys Lys Asp Ile Lys Ala Leu
```

-continued

```
                        325                 330                 335
GTT CTG ACC TGC CGT TGC AGG CCA CCT CAA GGG GAG CCT GAG CCT CTG      1233
Val Leu Thr Cys Arg Cys Arg Pro Pro Gln Gly Glu Pro Glu Pro Leu
                    340                 345                 350

CCC CTG TCC ACT GTG CAC ACG GAC CTC TCC AAG GGA TCT ATG AGG ATG      1281
Pro Leu Ser Thr Val His Thr Asp Leu Ser Lys Gly Ser Met Arg Met
                355                 360                 365

GGT AGC AAG TCT AAC GTC ATG TAG T CATGTCTAGG CTCTTCCGCC               1326
Gly Ser Lys Ser Asn Val Met  *
            370                 375

ATTTCTTTCG ACACACCCTT TCACTGAGCT AAGTAGACAC AATGCAAGCT GTGGTATCAT    1386

CCTGCCATTT CTGGTCTTTG GGGCCCAGAC AGGCGGCAAG AGACTTGAAG CTT           1439
```

(2) INFORMATION FOR SEQ ID NO:28:

(i) SEQUENCE CHARACTERISTICS:
        (A) LENGTH: 375 amino acids
        (B) TYPE: amino acid
        (D) TOPOLOGY: linear (ii) MOLECULE TYPE: protein (xi) SEQUENCE DESCRIPTION: SEQ ID NO:28:

```
Met Asn Thr Ser His Leu Met Ala Ser Leu Ser Pro Ala Phe Leu Gln
 1               5                  10                  15

Gly Lys Asn Gly Thr Asn Pro Leu Asp Ser Leu Tyr Asn Leu Ser Asp
                20                  25                  30

Gly Cys Gln Asp Ser Ala Asp Leu Leu Ala Phe Ile Ile Thr Thr Tyr
            35                  40                  45

Ser Val Glu Thr Val Leu Gly Val Leu Gly Asn Leu Cys Leu Ile Phe
         50                  55                  60

Val Thr Thr Arg Gln Lys Glu Lys Ser Asn Val Thr Asn Leu Leu Ile
 65                  70                  75                  80

Ala Asn Leu Ala Phe Ser Asp Phe Leu Met Cys Leu Ile Cys Gln Pro
                 85                  90                  95

Leu Thr Val Thr Tyr Thr Ile Met Asp Tyr Trp Ile Phe Gly Glu Val
            100                 105                 110

Leu Cys Lys Met Leu Thr Phe Ile Gln Cys Met Ser Val Thr Val Ser
        115                 120                 125

Ile Leu Ser Leu Val Leu Val Ala Leu Glu Arg His Gln Leu Ile Ile
130                 135                 140

Asn Pro Thr Gly Trp Lys Pro Ser Ile Ser Gln Ala Tyr Leu Gly Ile
145                 150                 155                 160

Val Val Ile Trp Phe Ile Ser Cys Phe Leu Ser Leu Pro Phe Leu Ala
                165                 170                 175

Asn Ser Ile Leu Asn Asp Leu Phe His Tyr Asn His Ser Lys Val Val
            180                 185                 190

Glu Phe Leu Glu Asp Lys Val Val Cys Phe Val Ser Trp Ser Ser Asp
        195                 200                 205

His His Arg Leu Ile Tyr Thr Thr Phe Leu Leu Leu Phe Gln Tyr Cys
210                 215                 220

Val Pro Leu Ala Phe Ile Leu Val Cys Tyr Met Arg Ile Tyr Gln Arg
225                 230                 235                 240

Leu Gln Arg Gln Arg Arg Ala Phe His Thr His Thr Cys Ser Ser Arg
                245                 250                 255

Val Gly Gln Met Lys Pro Ile Asn Gly Met Leu Met Ala Met Val Thr
            260                 265                 270
```

```
Ala Phe Ala Val Leu Trp Leu Pro Leu His Val Phe Asn Thr Leu Glu
            275                 280                 285
Asp Trp Tyr Gln Glu Ala Ile Pro Ala Cys His Gly Asn Leu Ile Phe
            290                 295                 300
Leu Met Cys His Leu Phe Ala Met Ala Ser Thr Cys Val Asn Pro Phe
305                 310                 315                 320
Ile Tyr Gly Phe Leu Asn Ile Asn Phe Lys Lys Asp Ile Lys Ala Leu
                325                 330                 335
Val Leu Thr Cys Arg Cys Arg Pro Pro Gln Gly Glu Pro Glu Pro Leu
            340                 345                 350
Pro Leu Ser Thr Val His Thr Asp Leu Ser Lys Gly Ser Met Arg Met
            355                 360                 365
Gly Ser Lys Ser Asn Val Met
370                 375
```

(2) INFORMATION FOR SEQ ID NO:29:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CGCGTGTTTC ACAAGGGCAC CTA                              23

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

TGCCACTTAG CCTCAGGGAC CC                              22

(2) INFORMATION FOR SEQ ID NO:31:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

TCCGTATGTA CTGTGGACAG GGGCAGATGC TCCGACTCCT CCAGG             45

(2) INFORMATION FOR SEQ ID NO:32:

(i) SEQUENCE CHARACTERISTICS:
        (A) LENGTH: 350 amino acids
        (B) TYPE: amino acid
        (D) TOPOLOGY: linear (ii) MOLECULE TYPE: protein (xi) SEQUENCE DESCRIPTION: SEQ ID NO:32:

Met Asn Thr Ser His Leu Met Ala Ser Leu Ser Pro Ala Phe Leu Gln

```
 1               5                   10                  15
Gly Lys Asn Gly Thr Asn Pro Leu Asp Ser Leu Tyr Asn Leu Ser Asp
                20                  25                  30

Gly Cys Gln Asp Ser Ala Asp Leu Leu Ala Phe Ile Ile Thr Thr Tyr
                35              40                  45

Ser Val Glu Thr Val Leu Gly Val Leu Gly Asn Leu Cys Leu Ile Phe
 50                      55                  60

Val Thr Thr Arg Gln Lys Glu Lys Ser Asn Val Thr Asn Leu Leu Ile
 65                  70              75                      80

Ala Asn Leu Ala Phe Ser Asp Phe Leu Met Cys Leu Ile Cys Gln Pro
                85                  90                  95

Leu Thr Val Thr Tyr Thr Ile Met Asp Tyr Trp Ile Phe Gly Glu Val
                100                 105                 110

Leu Cys Lys Met Leu Thr Phe Ile Gln Cys Met Ser Val Thr Val Ser
                115                 120                 125

Ile Leu Ser Leu Val Leu Val Ala Leu Glu Arg His Gln Leu Ile Ile
                130                 135                 140

Asn Pro Thr Gly Trp Lys Pro Ser Ile Ser Gln Ala Tyr Leu Gly Ile
 145                 150                 155                 160

Val Val Ile Trp Phe Ile Ser Cys Phe Leu Ser Leu Pro Phe Leu Ala
                165                 170                 175

Asn Ser Ile Leu Asn Asp Leu Phe His Tyr Asn His Ser Lys Val Val
                180                 185                 190

Glu Phe Leu Glu Asp Lys Val Val Cys Phe Val Ser Trp Ser Ser Asp
                195                 200                 205

His His Arg Leu Ile Tyr Thr Thr Phe Leu Leu Phe Gln Tyr Cys
 210                 215                 220

Val Pro Leu Ala Phe Ile Leu Val Cys Tyr Met Arg Ile Tyr Gln Arg
 225                 230                 235                 240

Leu Gln Arg Gln Arg Ala Phe His Thr His Thr Cys Ser Ser Arg
                245                 250                 255

Val Gly Gln Met Lys Arg Ile Asn Gly Met Leu Met Ala Met Val Thr
                260                 265                 270

Ala Phe Ala Val Leu Trp Leu Pro Leu His Val Phe Asn Thr Leu Glu
                275                 280                 285

Asp Trp Tyr Gln Glu Ala Ile Pro Ala Cys His Gly Asn Leu Ile Phe
 290                 295                 300

Leu Met Cys His Leu Phe Ala Met Ala Ser Thr Cys Val Asn Pro Phe
 305                 310                 315                 320

Ile Tyr Gly Phe Leu Asn Ile Asn Phe Lys Lys Asp Ile Lys Ala Leu
                325                 330                 335

Val Leu Thr Cys Arg Cys Arg Pro Pro Gln Gly Glu Pro Glu
                340                 345                 350
```

(2) INFORMATION FOR SEQ ID NO:33:

(i) SEQUENCE CHARACTERISTICS:
        (A) LENGTH: 350 amino acids
        (B) TYPE: amino acid
        (D) TOPOLOGY: linear (ii) MOLECULE TYPE: protein (xi) SEQUENCE DESCRIPTION: SEQ ID NO:33:

```
Met Asn Thr Ser His Leu Leu Ala Leu Leu Pro Lys Ser Pro Gln
 1               5                   10                  15
```

-continued

```
Gly Glu Asn Arg Ser Lys Pro Leu Gly Thr Pro Tyr Asn Phe Ser Glu
            20                  25                  30

His Cys Gln Asp Ser Val Asp Val Met Val Phe Ile Val Thr Ser Tyr
            35                  40                  45

Ser Ile Glu Thr Val Val Gly Val Leu Gly Asn Leu Cys Leu Met Cys
    50                  55                  60

Val Thr Val Arg Gln Lys Glu Lys Ala Asn Val Thr Asn Leu Leu Ile
65                  70                  75                  80

Ala Asn Leu Ala Phe Ser Asp Phe Leu Met Cys Leu Leu Cys Gln Pro
                85                  90                  95

Leu Thr Ala Val Tyr Thr Ile Met Asp Tyr Trp Ile Phe Gly Glu Thr
                100                 105                 110

Leu Cys Lys Met Ser Ala Phe Ile Gln Cys Met Ser Val Thr Val Ser
            115                 120                 125

Ile Leu Ser Leu Val Leu Val Ala Leu Glu Arg His Gln Leu Ile Ile
            130                 135                 140

Asn Pro Thr Gly Trp Lys Pro Ser Ile Ser Gln Ala Tyr Leu Gly Ile
145                 150                 155                 160

Val Leu Ile Trp Val Ile Ala Cys Val Leu Ser Leu Pro Phe Leu Ala
                165                 170                 175

Asn Ser Ile Leu Glu Asn Val Phe His Lys Asn His Ser Lys Ala Leu
                180                 185                 190

Glu Phe Leu Ala Asp Lys Val Val Cys Thr Glu Ser Trp Pro Leu Ala
            195                 200                 205

His His Arg Thr Ile Tyr Thr Thr Phe Leu Leu Leu Phe Gln Tyr Cys
    210                 215                 220

Leu Pro Leu Gly Phe Ile Leu Val Cys Tyr Ala Arg Ile Tyr Arg Arg
225                 230                 235                 240

Leu Gln Arg Gln Gly Arg Val Phe His Lys Gly Thr Tyr Ser Leu Arg
                245                 250                 255

Ala Gly His Met Lys Gln Val Asn Val Val Leu Val Val Met Val Val
            260                 265                 270

Ala Phe Ala Val Leu Trp Leu Pro Leu His Val Phe Asn Ser Leu Glu
            275                 280                 285

Asp Trp His His Glu Ala Ile Pro Ile Cys His Gly Asn Leu Ile Phe
            290                 295                 300

Leu Val Cys His Leu Leu Ala Met Ala Ser Thr Cys Val Asn Pro Phe
305                 310                 315                 320

Ile Tyr Gly Phe Leu Asn Thr Asn Phe Lys Lys Glu Ile Lys Ala Leu
                325                 330                 335

Val Leu Thr Cys Gln Gln Ser Ala Pro Leu Glu Glu Ser Glu
            340                 345                 350
```

DNA ENCODING A HUMAN NEUROPEPTIDE Y/PEPTIDE YY/ PANCREATIC POLYPEPTIDE RECEPTOR (Y4) AND USES THEREOF

This application is a 371 national stage filing of PCT/US94/14436, filed Dec. 28, 1994, which is continuation-in-part of U.S. Ser. No. 08/176,412, filed Dec. 28, 1993, now U.S. Pat. No. 5,516,653, issued May 14, 1996.

BACKGROUND OF THE INVENTION

Throughout this application, various publications are referenced in parenthesis by Author and year. Full citations for these references may be found at the end of the specification immediately preceding the claims. The disclosure of these publications is hereby incorporated by reference into this application to describe more fully the art to which this invention pertains.

Neuropeptides are small peptides originating from large precursor proteins synthesized by peptidergic neurons and endocrine/paracrine cells. They hold promise for treatment of neurological, psychiatric, and endocrine disorders (De Wied, 1990). Often the precursors contain multiple biologically active peptides. There is great diversity of neuropeptides in the brain caused by alternative splicing of primary gene transcripts and differential precursor processing. The neuropeptide receptors serve to discriminate between ligands and to activate the appropriate signals. Thus, it is expected that the receptors for neuropeptides consist of a large number of members.

Neuropeptide Y (NPY), a 36-amino acid peptide, is the most abundant neuropeptide to be identified in mammalian brain. NPY is an important regulator in both the central and peripheral nervous systems (Heilig et al., 1990) and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and has contributed to vasoconstriction. NPY binding sites have been identified in a variety of tissues, including spleen (Lundberg et al., 1988), intestinal membranes, brain (Hinson et al., 1988), aortic smooth muscle (Mihara et al., 1989), kidney, testis, and placenta (Dumont et al., 1992). In addition, binding sites have been reported in a number of rat and human cell lines (eg. Y1 in SK-N-MC, MC-IXC, CHP-212, and PC12 cells; Y2 in SK-N-Be(2), CHP-234, and SMS-MSN)(Aakerlund et al., 1990; Grundemar et al., 1993).

NPY forms a family (called the pancreatic polypeptide family) together with pancreatic polypeptide (PP) and peptide YY (PYY) which all consist of 36 amino acids and have a common tertiary structure, the so-called PP-fold (Glover et al., 1985). Specific features of this family include a polyproline helix in residues 1 through 8, a β-turn in residues 9 through 14, an α-helix in residues 15 through 30, an outward-projecting C-terminus in residues 30 through 36, and a carboxy terminal amide which appears to be critical for biological activity (Schwartz et al., 1990). The C-terminal amidated residue of these peptides is essential for biological activity (Wahlestedt et al., 1986). Studies with peptide fragments of NPY have indicated that multiple NPY receptor subtypes exist (Wahlestedt et al., 1986). Three major NPY receptor subtypes (Y1, Y2 and Y3) have been defined by pharmacological criteria, with a fourth "atypical" Y1 receptor that has been proposed to regulate feeding behavior. The only NPY receptor which has been cloned to date is the Y1 receptor gene, from mouse (Eva et al., 1992), rat (Eva et al., 1990), and human (Larhammar et al., 1992). One of the key pharmacological features which distinguish Y1 and Y2 is the fact that the Y1 receptor (and not the Y2 receptor) responds to an analog of NPY modified at residues 31 and 34 ([Leu31,Pro34]NPY), whereas the Y2 receptor (and not the Y1 receptor) has high affinity for the NPY peptide carboxyl-terminal fragment NPY-(13–36) (Wahlstedt et al., 1986; Fuhlendorff et al., 1990).

Receptor genes for the other two structurally related peptides, peptide YY (PYY) and pancreatic polypeptide (PP), also have not been cloned. Peptide YY occurs mainly in endocrine cells in the lower gastrointestinal tract (Bottcher et al., 1984). Receptors for PYY were first described in the rat small intestine (Laburthe et al., 1986). This receptor has been defined as PYY-preferring because it displays a 5–10 fold higher affinity for PYY than for NPY (Laburthe et al., 1986; Laburthe, 1990). Recently, a cell line, PKSV-PCT, derived from the proximal tubules of kidneys, has been described to express receptors for PYY (Voisin et al., 1993). Pancreatic polypeptide is predominantly located in endocrine cells of the pancreatic islets (Alumets et al., 1978). PP inhibits pancreatic exocrine secretion and gall bladder contraction (Schwartz, 1983). Interestingly, PP does not appear to be synthesized in or localized to the central nervous system (Di Maggio et al., 1985), but selective PP binding sites have been found in various brain areas, such as the area postrema and adjacent nuclei, regions permeable at the blood-brain barrier (Whitcomb et al., 1990). PP receptors have a much higher affinity for PP than for NPY or PYY (Inui et al., 1990). PP has been shown to bind with high affinity to binding sites on a pheochromocytoma cell line, PC12 (Schwartz et al., 1987). The rank order of affinity for the pharmacologically defined receptors of NPY and related peptides are listed in Table 1.

Using an homology screening approach to clone novel NPY receptor genes, we describe here the isolation and characterization of a novel NPY/PYY/PP receptor clone which we have designated Y4. The Y4 receptor appears to have a unique pharmacological profile, relative to other NPY-related receptors, exhibiting highest affinity for pancreatic polypeptide itself. This receptor clone will enable us to further examine the possibility of receptor diversity and the existence of multiple subtypes within this family of receptors. These could then serve as invaluable tools for drug design for several pathophysiological conditions such as memory loss, depression, anxiety, epilepsy, pain, hypertension, locomotor problems, circadian rhythm disorders, eating/body weight disorders, sexual/reproductive disorders, nasal congestion, diarrhea, gastrointestinal and cardiovascular disorders.

SUMMARY OF THE INVENTION

This invention provides an isolated nucleic acid molecule encoding a Y4 receptor.

This invention also provides an isolated protein which is a Y4 receptor.

This invention provides a vector comprising an isolated nucleic acid molecule encoding a Y4 receptor.

This invention also provides vectors such as plasmids and baculovirus comprising a nucleic acid molecule encoding a Y4 receptor, adapted for expression in a bacterial cell, a yeast cell, an insect cell or a mammalian cell which additionally comprise the regulatory elements necessary for expression of the nucleic acid in the bacterial, yeast, insect or mammalian cells operatively linked to the nucleic acid encoding the Y4 receptor as to permit expression thereof.

This invention provides a mammalian cell comprising nucleic acid encoding a Y4 receptor.

This invention provides a method for determining whether a ligand can specifically bind to a Y4 receptor which comprises contacting cell transfected with and expressing nucleic acid encoding a Y4 receptor with the ligand under conditions permitting binding of ligands to such Y4 receptor, and detecting the presence of any of the ligand bound to a Y4 receptor, thereby determining whether the ligand binds specifically to a Y4 receptor.

This invention also provides a method for determining whether a ligand is a Y4 receptor agonist which comprises contacting a cell transfected with and expressing nucleic acid encoding a Y4 receptor with the ligand under conditions permitting the activation of a Y4 receptor functional response from the cell, and detecting by means of a bioassay, such as a second messenger response, an increase in Y4 receptor activity, thereby determining whether the ligand is a Y4 receptor agonist.

This invention further provides a method for determining whether a ligand is a Y4 receptor antagonist which comprises contacting a cell transfected with and expressing nucleic acid encoding a Y4 receptor with the ligand under conditions permitting the activation of a functional Y4 receptor response, and detecting by means of a bioassay, such as a second messenger response, a decrease in Y4 receptor activity, and thereby determining whether the ligand is a Y4 receptor antagonist.

This invention further provides a method of screening drugs to identify drugs which specifically bind to a Y4 receptor which comprises contacting a cell transfected with and expressing nucleic acid encoding a Y4 receptor with a plurality of drugs, and determining those drugs which bind to the cell, thereby identifying drugs which specifically bind to a Y4 receptor.

This invention also provides a method of screening drugs to identify which act as agonists of a Y4 receptor which comprises contacting a cell transfected with and expressing a Y4 receptor with a plurality of drugs under conditions permitting the activation of a functional Y4 receptor response, and determining those drugs which activate the receptor in the cell using a bioassay such as a second messenger assay, thereby identifying drugs Y4 receptor agonists.

This invention also provides a method of screening drugs to identify drugs which act as antagonists of a Y4 receptor which comprises contacting a cell transfected with and expressing a Y4 receptor with a plurality of drugs in the presence of a known human Y4 receptor agonist, such as PP, under conditions permitting the activation of a functional Y4 receptor response and determining those drugs which inhibit the activation of the receptor in the cell using a bioassay, such as a second messenger assay, thereby identifying drugs which act as antagonists of a Y4 receptor.

This invention provides a nucleic acid probe comprising a nucleic acid molecule of at least 15 nucleotides capable of specifically hybridizing with a unique sequence included within the sequence of a nucleic acid molecule encoding a Y4 receptor.

This invention also provides a method of detecting expression of the Y4 receptor on the surface of a cell by detecting the presence of mRNA coding for a Y4 receptor which comprises obtaining total mRNA from the cell and contacting the mRNA so obtained with a nucleic acid probe comprising a nucleic acid molecule of at least 15 nucleotides capable of specifically hybridizing with a unique sequence included within the sequence of a nucleic acid molecule encoding a Y4 receptor under hybridizing conditions, detecting the presence of mRNA hybridized to the probe, and thereby detecting the expression of the Y4 receptor by the cell.

This invention provides an antisense oligonucleotide having a sequence capable of hybridizing specifically an mRNA molecule which encodes a Y4 receptor so as to prevent translation of the mRNA molecule.

This invention provides an antibody directed to a Y4 receptor.

This invention provides a transgenic nonhuman mammal expressing nucleic acid encoding a Y4 receptor. This invention further provides a transgenic nonhuman mammal whose genome comprises antisense DNA complementary to DNA encoding a Y4 receptor so placed as to be transcribed into antisense mRNA which is complementary to mRNA encoding a Y4 receptor and which hybridizes to mRNA encoding a Y4 receptor thereby reducing its translation.

This invention provides a method of determining the physiological effects of expressing varying levels of Y4 receptors which comprises producing a transgenic nonhuman animal whose levels of Y4 receptor expression are varied by use of an inducible promoter which regulates Y4 receptor expression.

This invention also provides a method of determining the physiological effects of expressing varying levels of Y4 receptors which comprises producing a panel of transgenic nonhuman animals each expressing a different amount of Y4 receptor.

This invention provides a method for diagnosing a predisposition to a disorder associated with the activity of a specific human Y4 receptor allele which comprises: a. obtaining nucleic acid of subjects suffering from the disorder; b. performing a restriction digest of the nucleic acid with a panel of restriction enzymes; c. electrophoretically separating the resulting nucleic acid fragments on a sizing gel; d. contacting the resulting gel with a nucleic acid probe capable of specifically hybridizing to nucleic acid encoding a Y4 receptor and labelled with a detectable marker; e. detecting labelled bands which have hybridized to the nucleic acid encoding a Y4 receptor labelled with a detectable marker to create a unique band pattern specific to the DNA of subjects suffering from the disorder; f. preparing nucleic acid obtained for diagnosis by steps a–e; and g. comparing the unique band pattern specific to the nucleic acid of subjects suffering from the disorder from step e and the nucleic acid obtained for diagnosis from step f to determine whether the patterns are the same or different and to diagnose thereby predisposition to the disorder if the patterns are the same.

This invention provides a method of preparing the purified, isolated Y4 receptor which comprises a) constructing a vector adapted for expression in a cell which comprises the regulatory elements necessary for the expression of nucleic acid in the cell operativley linked to the nucleic acid encoding a Y4 receptor as to permit expression thereof, wherein the cell is selected from the group consisting of bacterial cells, yeast cells, insect cells and mammalian cells; b) inserting the vector of step in a suitable host cell; c) incubating the cells of step b under conditions allowing the expression of a Y4 receptor; d) recovering the receptor so produced; and e) purifying the receptor so recovered, thereby preparing an isolated, purified Y4 receptor.

This invention also provides a method of preparing the isolated Y4 receptor which comprises inserting nucleic acid encoding Y4 receptor in a suitable vector, inserting the resulting vector in a suitable host cell, recovering the receptor produced by the resulting cell, and purifying the receptor so recovered.

This invention provides an antisense oligonucleotide having a sequence capable of binding specifically with any sequences of an mRNA molecule which encodes the Y4 receptor so as to prevent translation of mRNA molecules which encode the Y4 receptor.

This invention also provides a transgenic nonhuman mammal expressing DNA encoding a human Y4 receptor.

This invention further provides a transgenic nonhuman mammal comprising a homologous recombination knockout of the native Y4 receptor.

This invention also provides a method of determining the physiological effects of expressing varying levels of a receptor which comprises producing a transgenic nonhuman animal whose levels of human Y4 receptor expression are varied by use of an inducible promoter which regulates receptor expression.

This invention also provides a method of determining the physiological effects of expressing varying levels of a human Y4 receptor which comprises producing a panel of transgenic nonhuman animals each expressing a different amount of the receptor.

This invention further provides a transgenic nonhuman mammal whose genome comprises antisense DNA complementary to DNA encoding a human Y4 receptor so placed as to be transcribed into antisense mRNA which is complementary to mRNA encoding the receptor and which hybridizes to MRNA encoding the receptor thereby preventing its translation.

This invention provides a method for determining whether a ligand not known to be capable of binding to the Y4 receptor can bind to the receptor which comprises contacting a mammalian cell comprising an isolated DNA molecule encoding the Y4 receptor with the ligand under conditions permitting binding of ligands known to bind to the receptor, detecting the presence of any of the ligand bound to the Y4 receptor, and thereby determining whether the ligand binds to the Y4 receptor.

BRIEF DESCRIPTION OF THE DRAWINGS

FIGS. 1A to 1E

Figure 5:
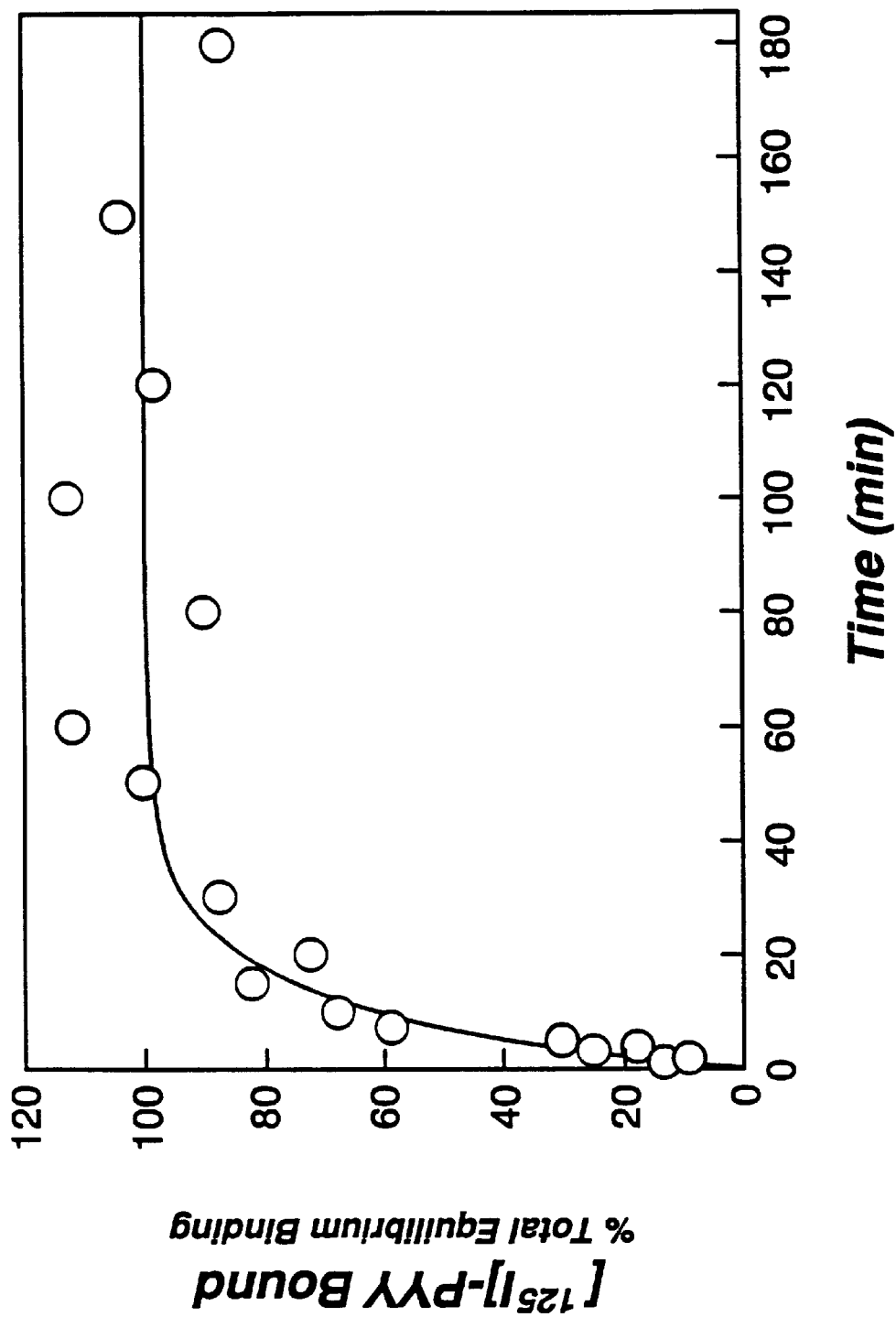

Nucleotide Sequence and Deduced Amino Acid Sequence of a Novel Human hp25a Neuropeptide Receptor (Sequence I.D. Nos. 1 and 2). Nucleotides are presented in the 5' to 3' orientation and the coding region is numbered starting from the initiating methionine and ending in the termination codon. Deduced amino acid sequence by translation of a long open reading frame is shown, along with the 5' and 3' untranslated regions. Numbers in the left and right margins represent nucleotide (top line) and amino acid (bottom line) numberings, starting with the first position as the adenosine (A) and the initiating methionine (M), respectively.

FIGS. 2A–2C

Sequence Alignment of the Human hp25a clone with human Y1, rat Y1, and mouse Y1 receptor genes. The deduced amino acid sequence of the human hp25a (Y4) receptor (first line) (SEQ ID NO: 2), from the starting methionine (M) to the stop codon (*), is aligned with the human Y1 receptor clone (SEQ ID NO: 15) (Larhammar et al., 1992), rat Y1 (SEQ ID NO: 13) receptor clone (Eva et al., 1990), and mouse Y1 (SEQ ID NO: 14) receptor clone (Eva et al., 1992). Hyphens represent added spaces necessary for proper alignment. Gray shading indicates residues in receptor clones which are identical to hp25a. Numbers above amino acid sequences correspond to amino acid positions of hp78a, starting with the initiating methionine (M) and ending with the termination codon (*), and including spaces to account for proper alignment. Solid bars above the sequence indicate the seven putative transmembrane (TM) spanning regions (TM I–VII).

FIGS. 3A–3D.

Nucleotide sequence and deduced amino acid sequence of the rat Y4 receptor encoded by rs16b (SEQ ID NOS: 27 and 28). Nucleotides are presented in the 5' to 3' orientation and the coding region is numbered starting from the putative initiating methionine and ending in the termination codon. Deduced amino acid sequence by translation of a long open reading frame is shown, along with 5' and 3' untranslated regions. The amino acid sequence is represented using single-letter abbreviations.

FIG. 4. Alignment of rat and human Y4 receptors. Predicted amino acid sequences of the rat Y4 receptor (Y4rat) (SEQ ID NO. 32) and human Y4 receptor (Y4hum) (SEQ ID NO: 33) are shown; the sequences are 75% identical overall and 84% identical in the transmembrane domains. Single letter abbreviations for amino acids are shown. The seven putative transmembrane (TM) spanning regions (TM I–VII) are indicated by brackets above the sequence.

FIG. 5

Equilibrium binding of $^{125}$I-PYY to membranes from COS-7 cells transiently expressing hp25a receptors. Membranes were incubated with $^{125}$I-PYY for the times indicated, in the presence or absence of 100 nM human PP. Specific binding, B, was plotted against time, t, to obtain the maximum number of equilibrium binding sites, $B_t$, and observed association rate, $K_{obs}$, according to the equation, $B=B_t*(1-e^{-(kobs*t)})$. Binding is shown as the percentage of total equilibrium binding, $B_t$, determined by nonlinear regression analysis. Data are representative of three independent experiments, with each point measured in triplicate.

FIG. 6A

Saturable equilibrium binding of $^{125}$I-PYY to membranes from COS-7 cells transiently expressing hp25a receptors. Membranes were incubated with $^{125}$I-PYY ranging in concentration from 0.003 nM to 2 nM, in the presence or absence of 100 nM human PP.

FIG. 6B

Figure 6A:
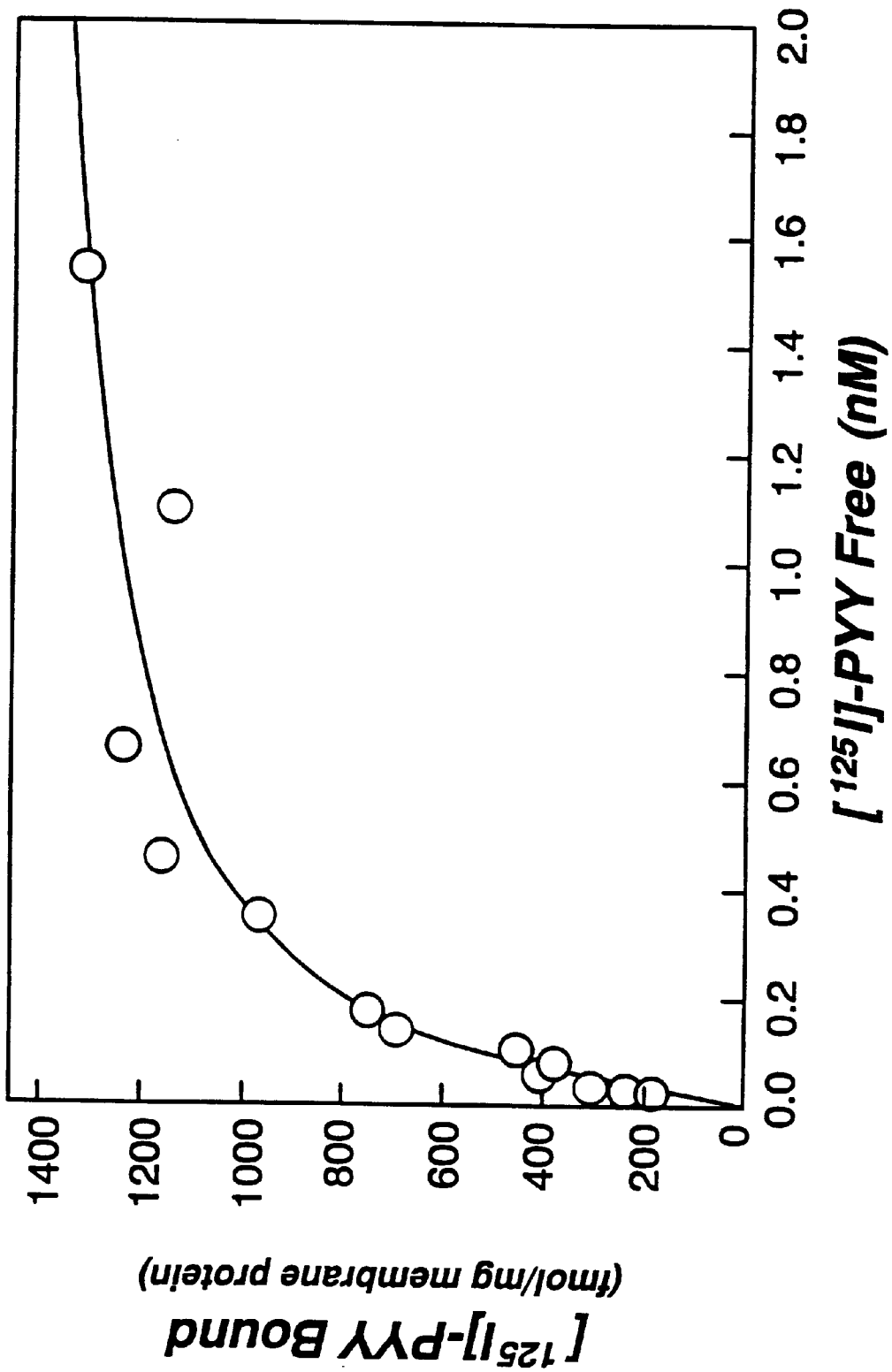

Specific binding of the $^{125}$I-PYY to membranes from COS-7 cells transiently expressing hp25a receptors under the conditions described in FIG. 6A was plotted against the free $^{125}$I-PYY concentration, [L], to obtain the maximum number of saturable binding sites, $B_{max}$, and the $^{125}$I-PYY equilibrium dissociation constant, $K_d$, according to the binding isotherm, $B=B_{max}[L]/([L]+K_d)$. Specific binding is shown for data from a representative of four independent experiments, with each point measured in quadruplicate.

FIG. 7.

Competitive displacement of $^{125}$I-PYY from COS-7 cells transiently expressing hp25a receptors. Membranes were incubated with $^{125}$I-PYY and increasing concentrations of peptide competitors. $IC_{50}$ values corresponding to 50% displacement were determined by nonlinear regression analysis and converted to $K_i$ values according to the equation, $K_i=IC_{50}/(1+[L]/K_d)$, where [L] is the $^{125}$I-PYY concentration and $K_d$ is the equilibrium dissociation constant of $^{125}$I-PYY. Data are representative of at least two independent experiments, with each point measured once or in duplicate. Rank orders of affinity for these and other compounds are listed separately in Table 2.

FIG. 8.

Inhibition of forskolin-stimulated cAMP accumulation in intact LM(tk−) cells stably expressing the human Y4 receptor. Functional data were derived from radioimmunoassay of cAMP in LM(tk−) cells stimulated with 10 μM forskolin over a 5 minute period. Human PP was tested for agonist activity at concentrations ranging from 0.03 pM to 0.3 μM over the same period. Data were fit to a four parameter logistic equation by nonlinear regression. The data shown are representative of three independent experiments.

FIGS. 9A and 9B.

FIG. 9A. Stimulation of intracellular free calcium concentration in intact LM(tk−) cells stably expressing the human Y4 receptor. Representative time course. Functional data were derived from Fura-2/AM fluorescence in LM(tk−) cells stimulated with 100 nM human PP (open squares) or 100 nM human NPY (closed squares) at the time indicated by the arrow. The data shown are representative of two independent experiments. FIG. 9B. Concentration/response curve. Data were fit to a four parameter logistic equation by nonlinear regression."

DETAILED DESCRIPTION OF THE INVENTION

Throughout this application, the following standard abbreviations are used to indicate specific nucleotide bases:

C = cytosine    A = adenine

T = thymine     G = guanine

This invention provides isolated nucleic acid molecules which encode Y4 receptors. In one embodiment the Y4 receptor encoded is a rat Y4 receptor. In another embodiment, the Y4 receptor encoded is a human Y4 receptor. In an embodiment, the isolated nucleic acid molecule encodes a Y4 receptor being characterized by an amino acid sequence in the transmembrane region, wherein the amino acid sequence has 60% homology or higher to the amino acid sequence in the transmembrane region of the human Y4 receptor shown in FIGS. 2A–2C. In another embodiment, the Y4 receptor has substantially the same amino acid sequence as the human Y4 receptor as described in FIGS. 1A–1E. In yet another embodiment, the Y4 receptor has substantially the same amino acid sequence as the rat Y4 receptor as described in FIGS. 3A–3D. In another embodiment, the Y4 receptor has the amino acid sequence as shown in FIGS. 1A–1E. In another embodiment, the Y4 receptor has the amino acid sequence as shown in FIGS. 3A–3D. As used herein, the term Y4 receptor encompasses any amino acid sequence, polypeptide or protein having substantially the same pharmacology provided subject human Y4 receptor as shown in Tables 1–3 and Table 6 and FIGS. 5–7. As described herein the human Y4 receptor has a pharmacological profile that differs from any known neuropeptide Y receptor subtype (i.e. Y1, Y2 and Y3), Neuropeptide YY receptor, and pancreatic polypeptide receptor, and is therefore designated as the human Y4 receptor.

The only NPY receptor which has been cloned to date is the Y1 receptor gene, from mouse (Eva et al., 1992), rat (Eva et al., 1990), and human (Larhammar et al., 1992). The Y4 receptor's greatest homology with any known receptor disclosed in the Genbank/EMBL databases is a 42% overall amino acid identity with the human Y1 receptor.

This invention provides an isolated nucleic acid molecule encoding a Y4 receptor. In one embodiment, the Y4 receptor is a human Y4 receptor. In another embodiment, the Y4 receptor is a rat Y4 receptor. As used herein, the term "isolated nucleic acid molecule" means a nucleic acid molecule that is a molecule in a form which does not occur in nature. Examples of such an isolated nucleic acid molecule are an RNA, cDNA, or isolated genomic DNA molecule encoding a Y4 receptor. One means of isolating a human Y4 receptor is to probe a human genomic library with a natural or artificially designed DNA probe, using methods well known in the art. DNA probes derived from the human receptor gene Y4 are particularly useful probes for this purpose. DNA and cDNA molecules which encode human Y4 receptors may be used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clones, and other stability, processing, transcription, translation, and tissue specificity-determining regions from the 3' and 5' untranslated regions of the isolated genes are thereby obtained. Examples of a nucleic acid molecule are an RNA, cDNA, or isolated genomic DNA molecule encoding a Y4 receptor. Such molecules may have coding sequences such as the coding sequences shown in FIGS. 1A–1E or FIGS. 3A–3D. The DNA molecule of FIGS. 1A–1E encodes the amino acid sequence of a human Y4 receptor protein, while the DNA molecule of FIG. 3 encodes the amino acid sequence of the rat Y4 receptor.

This invention further provides a cDNA molecule encoding a Y4 receptor having a coding sequence substantially the same as the coding sequence shown in FIGS. 1A–1E and FIGS. 3A–3D. This molecule is obtained by the means described above.

This invention also provides an isolated protein which is a Y4 receptor. In one embodiment, the Y4 receptor is a human Y4 receptor. In another embodiment, the Y4 receptor is a rat Y4 receptor. As used hereinin, the term "isolated protein" means a protein molecule free of other cellular components. An example of such a protein is an isolated protein having substantially the same amino acid sequence as the amino acid sequence shown in FIGS. 1A–1E which is a human Y4 receptor or the amino acid sequence shown in FIGS. 3A–3D which is a rat Y4 receptor. One means for obtaining isolated Y4 receptor is to express DNA encoding the receptor in a suitable host, such as a bacterial, yeast, insect or mammalian cell, using methods well known in the art, and recovering the receptor protein after it has been expressed in such a host, again using methods well known in the art. The receptor may also be isolated from cells which express it, in particular from cells which have been transfected with the expression vectors described below in more detail.

This invention provides vectors comprising isolated nucleic acid molecules such as DNA, RNA, or cDNA encoding a Y4 receptor. In one embodiment the Y4 receptor is a human Y4 receptor. In another embodiment the Y4 receptor is a rat Y4 receptor. Examples of vectors are viruses such as bacteriophages (such as phage lambda), animal viruses (such as Herpes virus, Murine Leukemia virus, and Baculovirus), cosmids, plasmids (such as pUC18, available from Pharmacia, Piscataway, N.J.), and other recombination vectors. Nucleic acid molecules are inserted into vector genomes by methods well known in the art. For example, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available. Specific examples of such plasmids are plasmids comprising cDNA having a coding sequence substantially the same as the coding sequence shown in FIGS. 1A–1E and designated clone hp25a (Seq. I.D. No. 1) or the coding sequence shown in FIGS. 3A–3D and designated clone rs16b (Sequence I.D. No. 27).

This invention also provides vectors comprising DNA molecules encoding Y4 receptors, adapted for expression in a bacterial cell, a yeast cell, an insect cell or a mammalian cell which additionally comprise the regulatory elements necessary for expression of the DNA in the bacterial, yeast, insect or mammalian cells operatively linked to the DNA encoding a Y4 receptor as to permit expression thereof. DNA having coding sequences substantially the same as the coding sequence shown in FIGS. 1A–1E may usefully be inserted into the vectors to express human Y4 receptors. DNA having coding sequences substantially the same as the coding sequence shown in FIGS. 3A–3D may usefully be inserted into the vectors to express rat Y4 receptors. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., Molecular Cloning, Cold Spring Harbor Laboratory, 1982).

Similarly, a eukaryotic expression vector includes a heterologous or homologous promoter for RNA polymerase II, a downstream polyadenylation signal, the start codon AUG, and a termination codon for detachment of the ribosome. Furthermore, an insect expression vector, such as recombinant Baculovirus, uses the polyhedrin gene expression signals for expression of the inserted gene in insect cells. Such vectors may be obtained commercially or assembled from the sequences described by methods well known in the art, for example the methods described above for constructing vectors in general. Expression vectors are useful to produce cells that express the receptor. Certain uses for such cells are described in more detail below.

This invention further provides a plasmid adapted for expression in a bacterial, yeast, insect, or, in particular, a mammalian cell which comprises a DNA molecule encoding a Y4 receptor and the regulatory elements necessary for expression of the DNA in the bacterial, yeast, insect, or mammalian cell operatively linked to the DNA encoding a Y4 receptor as to permit expression thereof. Some plasmids adapted for expression in a mammalian cell are pSVL (available from Pharmacia, Piscataway, N.J.) and pcEXV-3 (Miller J. and Germain R. N., J. Exp. Med. 164:1478 (1986)). A specific example of such plasmid is a plasmid adapted for expression in a mammalian cell comprising cDNA having coding sequences substantially the same as the coding sequence shown in FIGS. 1A–1E and the regulatory elements necessary for expression of the DNA in the mammalian cell which is designated pcEXV-Y4 and deposited under ATCC Accession No. 75631. Another example of such plasmid is a plasmid adapted for expression in a mammalian cell comprising cDNA having coding sequences substantially the same as the coding sequence shown in FIGS. 3A–3D (SEQ ID NO: 27) and the regulatory elements necessary for expression of the DNA in the mammalian cell which is designated pcEXV-rY4 and deposited under ATCC Accession number 75984. Those skilled in the art will readily appreciate that numerous plasmids adapted for expression in a mammalian cell which comprise DNA encoding Y4 receptors and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

The deposit discussed supra, and the other deposits discussed herein, were made pursuant to, and in satisfaction of, the Budapest Treaty on the International Recognition of the Deposit of Microorganisms for the Purpose of Patent Procedure with the American Type Culture Collection (ATCC), 10801 University Boulevard, Manassas, Va. 20110-2209.

This invention provides a cell comprising a nucleic acid encoding a Y4 receptor, such as a mammalian cell comprising a plasmid adapted for expression in a mammalian cell, which comprises a nucleic acid molecule encoding a Y4 receptor, the protein encoded thereby is expressed on the cell surface, and the regulatory elements necessary for expression of the nucleic acid in the mammalian cell operatively linked to the nucleic acid encoding a Y4 receptor as to permit expression thereof. Numerous mammalian cells may be used as hosts, including, for example, the mouse fibroblast cell NIH-3T3, CHO cells, HeLa cells, LM(tk–) cells, Y1 cells, etc. Expression plasmids such as that described supra may be used to transfect mammalian cells by methods well known in the art such as calcium phosphate precipitation, or DNA encoding these Y4 receptors may be otherwise introduced into mammalian cells, e.g., by microinjection, to obtain mammalian cells which comprise DNA, e.g., cDNA or a plasmid, encoding either Y4 receptor. In one embodiment, the LM(tk–) cell is designated L-hY4-3 (ATCC Accession No. CRL-11779). In another embodiment, the NIH-3t3 cell is designated N-hY4-5 (ATCC Accession No. CRL-11779).

This invention provides a method for determining whether a ligand can specifically bind to a Y4 receptor which comprises contacting a cell transfected with and expressing nucleic acid encoding the Y4 receptor with the ligand under conditions permitting binding of ligands to such receptor, and detecting the presence of any such ligand bound specifically to the Y4 receptor, thereby determining whether the ligand binds specifically to a Y4 receptor. In one embodiment, the Y4 receptor is a human Y4 receptor. In another embodiment, the Y4 receptor is a rat Y4 receptor.

This invention provides a method for determining whether a ligand can specifically bind to a Y4 receptor which comprises contacting a cell transfected with and expressing nucleic acid encoding the Y4 receptor with the ligand under conditions permitting binding of ligands to such receptor, and detecting the presence of any such ligand bound specifically to the Y4 receptor, thereby determining whether the ligand binds specifically to a Y4 receptor, wherein the Y4 receptor is characterized by an amino acid sequence in the transmembrane region, wherein the amino acid sequence has 60% homology or higher to the amino acid sequence in the transmembrane region of the human Y4 receptor shown in FIGS. 2A–2C. In one embodiment, the Y4 receptor is a human Y4 receptor. In another embodiment, the Y4 receptor is a rat Y4 receptor.

This invention provides a method for determining whether a ligand can bind specifically to a Y4 receptor which comprises preparing a cell extract from cells transfected with and expressing nucleic acid encoding a Y4 receptor, isolating a membrane fraction from the cell extract, contacting the ligand with the membrane fraction under conditions permitting binding of ligands to such receptor, and detecting the presence of any ligand bound to the Y4 receptor, thereby determining whether the compound is capable of specifically binding to a Y4 receptor. In one embodiment, the Y4 receptor is a human Y4 receptor. In another embodiment, the Y4 receptor is a rat Y4 receptor.

This invention provides a method for determining whether a ligand is a Y4 receptor agonist which comprises contacting a cell transfected with and expressing nucleic acid encoding a Y4 receptor with the ligand under conditions permitting the activation of a functional Y4 receptor response from the cell, and detecting by means of a bioassay, such as a second messenger response, an increase in Y4 receptor activity, thereby determining whether the ligand is a Y4 receptor agonist. In one embodiment, the Y4 receptor is a human Y4 receptor. In another embodiment, the Y4 receptor is a rat Y4 receptor.

This invention provides a method for determining whether a ligand is a Y4 receptor agonist which comprises preparing a cell extract from cells transfected with and expressing nucleic acid encoding a Y4 receptor, isolating a membrane fraction from the cell extract, contacting the membrane fraction with the ligand under conditions permitting the activation of a functional Y4 receptor response, and detecting by means of a bioassay, such as a second messenger response, an increase in Y4 receptor activity, thereby determining whether the ligand is a Y4 receptor agonist. In one embodiment, the Y4 receptor is a human Y4 receptor. In another embodiment, the Y4 receptor is a rat Y4 receptor.

This invention provides a method for determining whether a ligand is a Y4 receptor antagonist which comprises contacting a cell transfected with and expressing nucleic acid encoding a Y4 receptor with the ligand in the presence of a known Y4 receptor agonist, such as PP, under conditions permitting the activation of a functional Y4 receptor response and detecting by means of a bioassay, such as a second messenger response, a decrease in Y4 receptor activity, thereby determining whether the ligand is a Y4 receptor antagonist. In one embodiment, the Y4 receptor is a human Y4 receptor. In another embodiment, the Y4 receptor is a rat Y4 receptor.

This invention provides a method for determining whether a ligand is a Y4 receptor antagonist which comprises preparing a cell extract from cells transfected with and expressing nucleic acid encoding a Y4 receptor, isolating a membrane fraction from the cell extract, contacting the membrane fraction with the ligand in the presence of a known Y4 receptor agonist, such as PP, under conditions permitting the activation of a functional Y4 receptor response and detecting by means of a bioassay, such as a second messenger response, a decrease in Y4 receptor activity, thereby determining whether the ligand is a Y4 receptor antagonist. In one embodiment, the Y4 receptor is a human Y4 receptor. In another embodiment, the Y4 receptor is a rat Y4 receptor.

In one embodiment of the above-described methods, the ligand is not previously known.

This invention provides a Y4 receptor agonist detected by the above-described method. This invention provides a Y4 receptor antagonist detected by the above-described method.

As used herein, the term "agonist" means any ligand capable of increasing Y4 receptor activity. As used herein, the term "antagonist" means any ligand capable of decreasing Y4 receptor activity.

In one embodiment of the above-described methods, the cell is a mammalian cell. In a further embodiment, the cell is non-neuronal in origin. In another embodiment, the non-neuronal cell is a COS-7 cell, a CHO cell, an NIH-3T3 cell or an LM(tk−) cell.

One method for determining whether a ligand is capable of binding to the human Y4 receptor comprises contacting a transfected nonneuronal cell (i.e. a cell that does not naturally express any type of NPY, PP, or PYY receptor, thus will only express such a receptor if it is transfected into the cell) expressing a Y4 receptor on its surface, or contacting a membrane preparation derived from such a transfected cell, with the ligand under conditions which are known to prevail, and thus to be associated with, in vivo binding of the ligands to a Y4 receptor, detecting the presence of any of the ligand being tested bound to the Y4 receptor on the surface of the cell, and thereby determining whether the ligand binds to, activates or inhibits the activation of the Y4 receptor. A response system for detecting the activation or inhibition of activation of the Y4 receptor is obtained by transfection of isolated DNA into a suitable host cell containing the desired second messenger system such as phosphoinositide hydrolysis, adenylate cyclase, guanylate cyclase or ion channels. Such a suitable host cell system is isolated from pre-existing cell lines, or can be generated by inserting appropriate components of second messenger systems into existing cell lines. Such a transfection system provides a complete response system for investigation or assay of the activity of Y4 receptors with ligands as described above. Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the Y4 receptor. The transfection system is also useful for determining the affinity and efficacy of known drugs at the Y4 receptor sites.

This invention also provides a method of screening drugs to identify drugs which specifically bind to a Y4 receptor on the surface of a cell which comprises contacting a cell transfected with and expressing nucleic acid encoding a Y4 receptor with a plurality of drugs, and determining those drugs which bind to the cell, thereby identifying drugs which specifically bind to a Y4 receptor.

This invention also provides a method of screening drugs to identify drugs which specifically bind to a Y4 receptor on the surface of a cell which comprises preparing a cell extract from cells transfected with and expressing nucleic acid encoding a Y4 receptor, isolating a membrane fraction from the cell extract, contacting the membrane fraction with a plurality of drugs, and determining those drugs which bind to the membrane fraction, thereby identifying drugs which specifically bind to a Y4 receptor.

This invention also provides a method of screening drugs to identify drugs which act as Y4 receptor agonists which comprises contacting a cell transfected with and expressing nucleic acid encoding a Y4 receptor with a plurality of drugs under conditions permitting the activation of a functional Y4 receptor response, determining those drugs which activate the Y4 receptor in the cell using a bioassay, such as a second messenger assay, thereby identifying drugs which act as Y4 receptor agonists.

This invention also provides a method of screening drugs to identify drugs which act as Y4 receptor agonists which comprises preparing a cell extract from cells transfected with and expressing nucleic acid encoding a Y4 receptor, isolating a membrane fraction from the cell extract, contacting the membrane fraction with a plurality of drugs under conditions permitting the activation of a functional Y4 receptor response, determining those drugs which activate the Y4 receptor in the cell using a bioassay, such as a second messenger assay, thereby identifying drugs which act as Y4 receptor agonists.

This invention also provides a method of screening drugs to identify drugs which act as Y4 receptor antagonists which comprises contacting a cell transfected with and expressing DNA encoding a Y4 receptor with a plurality of drugs in the presence of a known Y4 receptor agonist, such as PP, under conditions permitting the activation of a functional Y4 receptor response, and determining those drugs which inhibit the activation of the Y4 receptor in the cell using a bioassay, such as a second messenger assay, thereby identifying drugs which act as Y4 receptor antagonists.

This invention also provides a method of screening drugs to identify drugs which act as Y4 receptor antagonists which comprises preparing a cell extract from cells transfected with and expressing nucleic acid encoding a Y4 receptor, isolating a membrane fraction from the cell extract, contacting the membrane fraction with a plurality of drugs in the presence of a known Y4 receptor agonist, such as PP, under conditions permitting the activation of a functional Y4 receptor response, and determining those drugs which inhibit the activation of the Y4 receptor in the cell using a bioassay, such as a second messenger assay, thereby identifying drugs which act as Y4 receptor antagonists.

In one embodiment of the above-identified methods, the Y4 receptor is a human Y4 receptor. In another embodiment, the Y4 receptor is a rat Y4 receptor. In one embodiment, the cell is a mammalian cell. In another embodiment, the mammalian cell is non-neuronal in origin. In a further embodiment, the mammalian cell non-neuronal in origin is a Cos-7 cell, a CHO cell, an LM(tk-) cell, a Y1 murine adrenal cell, or an NIH-3T3 cell.

The nucleic acid in the cell may have a coding sequence substantially the same as the coding sequences shown in FIGS. 1A–1E and FIGS. 3A–3D. Drug candidates are identified by choosing chemical compounds which bind with high affinity to the expressed Y4 receptor protein in transfected cells, using radioligand binding methods well known in the art, examples of which are shown in the binding assays described herein. Drug candidates are also screened for selectivity by identifying compounds which bind with high affinity to the Y4 receptor but do not bind with high affinity to any other NPY receptor subtype or to any other known receptor site. Because selective, high affinity compounds interact primarily with the target Y4 receptor site after administration to the patient, the chances of producing a drug with unwanted side effects are minimized by this approach.

This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bio-available following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bio-available, in an appropriate solid or solution formulation, to gain the desired therapeutic benefit.

This invention provides a nucleic acid probe comprising a nucleic acid molecule of at least 15 nucleotides capable of specifically hybridizing with a unique sequence included within the coding sequence of a nucleic acid molecule encoding a Y4 receptor, for example with a coding sequence included within the sequences shown in FIGS. 1A–1E and FIGS. 3A–3D. In one embodiment, the nucleic acid encodes a human Y4 receptor. In another embodiment, the nucleic acid encodes a rat Y4 receptor. As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding a Y4 receptor. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding human Y4 receptors is useful as a diagnostic test for any disease process in which levels of expression of the corresponding Y4 receptor is altered. Nucleic acid probe molecules are produced by insertion of a nucleic acid molecule which encodes a Y4 receptor or fragments thereof into suitable vectors, such as plasmids or bacteriophages, followed by insertion into suitable bacterial host cells and replication and harvesting of the nucleic acid probes, all using methods well known in the art. For example, the nucleic acid may be extracted from a cell lysate using phenol and ethanol, digested with restriction enzymes corresponding to the insertion sites of the nucleic acid into the vector (discussed above), electrophoresed, and cut out of the resulting gel. Example of such nucleic acid molecules are shown in FIGS. 1A–1E (SEQ ID NO: 1) and FIGS. 3A–3D (SEQ ID NO: 27). The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a Y4 receptor of are useful as probes for these genes, for their associated mRNA, or for the isolation of related genes by homology screening of genomic or cDNA libraries, or by the use of amplification techniques such as the Polymerase Chain Reaction. Synthesized oligonucleotides as described may also be used to determine the cellular localization of the mRNA produced by the Y4 gene by in situ hybridization.

This invention also provides a method of detecting expression of a Y4 receptor by detecting the presence of mRNA coding for a Y4 receptor which comprises obtaining total mRNA from the cell using methods well known in the art and contacting the mRNA so obtained with a nucleic acid probe comprising a nucleic acid molecule of at least 15 nucleotides capable of specifically hybridizing with a sequence included within the sequence of a nucleic acid molecule encoding a Y4 receptor under hybridizing conditions, and detecting the presence of mRNA hybridized to the probe, thereby detecting the expression of the Y4 receptor by the cell. Hybridization of probes to target nucleic acid molecules such as mRNA molecules employs techniques well known in the art. In one possible means of performing this method, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of specifically hybridizing with any sequences of an mRNA molecule which encodes a Y4 receptor so as to prevent translation of the mRNA molecule. The antisense oligonucleotide may have a sequence capable of specifically hybridizing with any sequences of the cDNA molecule whose sequence is shown in FIGS. 1A–1E or FIGS. 3A–3D. A particular example of an antisense oligonucleotide is an antisense oligonucleotide comprising chemical analogues of nucleotides.

This invention also provides a pharmaceutical composition comprising an amount of the oligonucleotide described above effective to reduce activity of a human Y4 receptor by passing through a cell membrane and specifically binding with mRNA encoding a Y4 receptor in the cell so as to prevent its translation and a pharmaceutically acceptable carrier capable of passing through a cell membrane. The oligonucleotide may be coupled to a substance which inactivates mRNA, such as a ribozyme. The pharmaceutically acceptable carrier capable of passing through cell membranes may also comprise a structure which binds to a receptor on a cell capable of being taken up by cells after binding to the structure. The structure of the pharmaceutically acceptable carrier may be capable of binding to a receptor which is specific for a xelected cell type. The structure may be part of a protein known to bind a cell-type specific receptor, for example an insulin molecule, which would target pancreatic cells. Nucleic molecules having coding sequences substantially the same as the coding sequences shown in FIGS. 1A–1E and FIGS. 3A–3D may be used as the oligonucleotides of the pharmaceutical composition.

This invention also provides a method of treating an abnormality wherein the abnormality is alleviated by decreasing the activity of a Y4 receptor which comprises administering to a subject an amount of the pharmaceutical composition described above effective to decrease the activity of the Y4 receptor. Several examples of such abnormal conditions are amnesia, anxiety, epilepsy, pain, hypertension, locomotor problems, circadian rhythm disorders, eating/body weight disorders, sexual/reproductive disorders, nasal congestion, diarrhea, gastrointestinal and cardiovascular disorders, and sleep and eating disorders.

Antisense oligonucleotide drugs inhibit translation of mRNA encoding these receptors. Synthetic oligonucleotides, or other antisense chemical structures are designed to bind to mRNA encoding the Y4 receptor and inhibit translation of mRNA and are useful as drugs to inhibit expression of Y4 receptor genes in patients. This invention provides a means to therapeutically alter levels of expression of human Y4 receptors by the use of a synthetic antisense oligonucleotide drug (SAOD) which inhibits translation of mRNA encoding these receptors. Synthetic oligonucleotides, or other antisense chemical structures designed to recognize and selectively bind to mRNA, are constructed to be complementary to portions of the nucleotide sequences shown in FIGS. 1A–1E and FIGS. 3A–3D of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g. by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which binds and takes up the SAOD only within certain selected cell populations. For example, the SAOD may be designed to bind to a receptor found only in a certain cell type, as discussed above. The SAOD is also designed to recognize and selectively bind to the target mRNA sequence, which may correspond to a sequence contained within the sequences shown in FIGS. 1A–1E and FIGS. 3A–3D by virtue of complementary base pairing to the mRNA. Finally, the SAOD. is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (J. S. Cohen, Trends in Pharm. Sci. 10, 435 (1989); H. M. Weintraub, Sci. Am. January (1990) p. 40). In addition, coupling of ribozymes to antisense oligonucleotides is a promising strategy for inactivating target mRNA (N. Sarver et al., Science 247, 1222 (1990)). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce receptor expression in particular target cells of a patient, in any clinical condition which may benefit from reduced expression of Y4 receptors.

This invention provides an antibody directed to a Y4 receptor, for example a monoclonal antibody directed to an epitope of a Y4 receptor present on the surface of a cell and having an amino acid sequence substantially the same as an amino acid sequence for a cell surface epitope of the human Y4 receptor included in the amino acid sequence shown in FIGS. 1A–1E (Seq. I.D. No. 2) or the rat Y4 receptor included in the amino acid sequence shown in FIGS. 3A–3D (Seq. I.D. No. 28). Amino acid sequences may be analyzed by methods well known in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIGS. 1A–1E and FIGS. 3A–3D will probably bind to a surface epitope of a human or rat Y4 receptor, respectivley, as described. Antibodies directed to Y4 receptors may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as COS-7 cells or LM(tk–) cells comprising DNA encoding the human Y4 receptor and thereby expressing the human Y4 receptor may be used as immunogens to raise such an antibody. Alternatively, synthetic peptides may be prepared using commercially available machines and the amino acid sequences shown in FIGS. 1A–1E and FIGS. 3A–3D (Seq. I.D. Nos. 2 and 28). As a still further alternative, DNA, such as a cDNA or a fragment thereof, may be cloned and expressed and the resulting polypeptide recovered and used as an immunogen. These antibodies are useful to detect the presence of human Y4 receptors encoded by the isolated DNA, or to inhibit the function of the receptors in living animals, in humans, or in biological tissues or fluids isolated from animals or humans.

This invention provides a pharmaceutical composition which comprises an amount of an antibody directed to the human Y4 receptor effective to block binding of ligands to the Y4 receptor, and a pharmaceutically acceptable carrier. A monoclonal antibody directed to an epitope of a Y4 receptor present on the surface of a cell and having an amino acid sequence substantially the same as an amino acid sequence for a cell surface epitope of the Y4 receptor included in the amino acid sequences shown in FIGS. 1A–1E and FIGS. 3A–3D is useful for this purpose. In one embodiment, the Y4 receptor is a human Y4 receptor. In another embodiment, the Y4 receptor is a rat Y4 receptor.

This invention also provides a method of treating an abnormality wherein the abnormality is alleviated by decreasing the activity of a Y4 receptor which comprises administering to a subject an amount of the pharmaceutical composition described above effective to block binding of ligands to the Y4 receptor, thereby treating the abnormality. Binding of the antibody to the receptor prevents the receptor from functioning, thereby neutralizing the effects of Y4 receptor activity. The monoclonal antibodies described above are both useful for this purpose. Some examples of abnormalities are amnesia, depression, anxiety, epilepsy, pain, depression, hypertension, and sleep and eating disorders.

This invention provides a method of detecting the presence of a Y4 receptor on the surface of a cell which comprises contacting the cell with an antibody directed to the Y4 receptor, under conditions permitting binding of the antibody to the receptor, and detecting the presence of the antibody bound to the cell, thereby detecting the presence of the Y4 receptor on the surface of the cell. Such a method is useful for determining whether a given cell is defective in activity of Y4 receptors on the surface of the cell. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing nucleic acid encoding a Y4 receptor. This invention also provides a transgenic nonhuman mammal comprising a homologous recombination knockout of the native Y4 receptor. This invention also provides a transgenic nonhuman mammal whose genome comprises antisense DNA complementary to DNA encoding a Y4 receptor so placed as to be transcribed into antisense mRNA which is complementary to mRNA encoding a Y4 receptor and which hybridizes to mRNA encoding a Y4 receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIGS. 1A–1E and FIGS. 3A–3D. An example of a transgenic animal is a transgenic mouse. Examples of tissue specificity-determining regions are the metallothionein promotor (Low, M. J., Lechan, R. M., Hammer, R. E. et al. Science 231:1002–1004 (1986)) and the L7 promotor (Oberdick, J., Smeyne, R. J., Mann, J. R., Jackson, S. and Morgan, J. I. Science 248:223–226 (1990)).

Animal model systems which elucidate the physiological and behavioral roles of Y4 receptors are produced by creating transgenic animals in which the activity of a Y4 receptor is either increased or decreased, or the amino acid sequence of the expressed Y4 receptor protein is altered, by a variety of techniques. Examples of these techniques include: 1) Insertion of normal or mutant versions of DNA encoding a Y4 receptor or homologous animal versions of these genes, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)). 2) Homologous recombination (Capecchi M. R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these Y4 receptors. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor. One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a human Y4 receptor is purified from a vector (such as plasmid pcEXV-Y4 described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit receptor activity, the transgenic animal model systems described above are useful for testing the biological activity of drugs directed against these Y4 receptors even before such drugs become available. These animal model systems are useful for predicting or evaluating possible therapeutic applications of drugs which activate or inhibit Y4 receptor activity by inducing or inhibiting expression of the native or trans-gene and thus increasing or decreasing activity of normal or mutant Y4 receptors in the living animal. Thus, a model system is produced in which the biological activity of drugs directed against these Y4 receptors are evaluated before such drugs become available. The transgenic animals which have increased or decreased Y4 receptor activity indicate by their physiological state whether increase or decrease of the Y4 receptor activity is therapeutically useful. It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to decreased activity of the receptor. Therefore, an animal which has decreased receptor activity is useful as a test system to investigate whether the actions of such drugs which result in decreased receptor activity are in fact therapeutic. Another use is that if increased receptor activity is found to lead to abnormalities, then a drug which down-regulates or acts as an antagonist to Y4 receptor is indicated as worth developing, and if a promising therapeutic application is uncovered by these animal model systems, activation or inhibition of Y4 receptor activity is achieved therapeutically either by producing agonist or antagonist drugs directed against these Y4 receptors or by any method which increases or decreases the activity of these Y4 receptors.

This invention provides a method of determining the physiological effects of expressing varying levels of human Y4 receptors which comprises producing a transgenic non-human animal whose levels of human Y4 receptor activity are varied by use of an inducible promoter which regulates Y4 receptor expression. This invention also provides a method of determining the physiological effects of expressing varying levels of Y4 receptors which comprises producing a panel of transgenic nonhuman animals each expressing a different amount of Y4 receptor activity. Such animals may be produced by introducing different amounts of nucleic acid encoding a Y4 receptor into the oocytes from which the transgenic animals are developed.

This invention also provides a method for identifying a Y4 receptor antagonist capable of alleviating an abnormality in a subject, wherein the abnormailty is alleviated by decreasing the activity of a Y4 receptor which comprises administering the antagonist to a transgenic nonhuman mammal expressing at least one artificially introduced nucleic acid molecule encoding a Y4 receptor and determining whether the antagonist alleviates the physical and behavioral abnormalities displayed by the transgenic nonhuman mammal as a result of activity of a Y4 receptor, thereby identifying a Y4 receptor antagonist. As used herein, the term "antagonist" means a compound or composition which may be natural, synthetic, or a product derived from screening. Examples of nucleic acid molecules are DNA, cDNA, genomic DNA, synthetic DNA or RNA molecules having coding sequences substantially the same as the coding sequences shown in FIGS. 1A–1E and FIGS. 3A–3D. This invention also provides an antagonist identified by the method described above.

This invention provides a pharmaceutical composition comprising an amount of the antagonist described supra and a pharmaceutically acceptable carrier.

This invention further provides a method for treating an abnormality in a subject wherein the abnormality is alleviated by decreasing the activity of a Y4 receptor which comprises administering to the subject an effective amount of the pharmaceutical composition described above, thereby treating the abnormality.

This invention provides a method for identifying a Y4 receptor agonist capable of alleviating an abnormality in a subject wherein the abnormality is alleviated by activation of a Y4 receptor which comprises administering the agonist to the transgenic nonhuman mammals described above determining whether the agonist alleviates the physical and behavioral abnormalities displayed by the transgenic nonhuman mammal, the alleviation of the abnormality indicating the identification of a Y4 receptor agonist.

This invention provides an agonist identified by the method described above.

This invention also provides a pharmaceutical composition comprising an amount of the agonist identified by the method described above and a pharmaceutically acceptable carrier.

This invention further provides a method for treating an abnormality in a subject wherein the abnormailty is alleviated by activation of a Y4 receptor which comprises administering to a subject an effective amount of the pharmaceutical composition described above, thereby treating the abnormality.

This invention provides a method for diagnosing a predisposition to a disorder associated with the activity of a specific Y4 receptor allele which comprises: a) obtaining DNA of subjects suffering from the disorder; b) performing a restriction digest of the DNA with a panel of restriction enzymes; c. electrophoretically separating the resulting DNA fragments on a sizing gel; d) contacting the resulting gel with a nucleic acid probe capable of specifically hybridizing to DNA encoding a Y4 receptor and labelled with a detectable marker; e) detecting labelled bands which have hybridized to the DNA encoding a Y4 receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific Y4 receptor allele.

This invention provides a method of preparing the purified, isolated Y4 receptor which comprises a) constructing a vector adapted for expression in a cell which comprises the regulatory elements necessary for the expression of nucleic acid in the cell operatively linked to the nucleic acid encoding a Y4 receptor as to permit expression thereof, wherein the cell is selected from the group consisting of bacterial cells, yeast cells, insect cells and mammalian cells; b) inserting the vector of step a in a suitable host cell; c) incubating the cells of step b under conditions allowing the expression of a Y4 receptor; d) recovering the receptor so produced; and e) purifying the receptor so recovered, thereby preparing the purified, isolated Y4 receptor. An example of an isolated Y4 receptor is an isolated protein having substantially the same amino acid sequence as the amino acid sequences shown in FIGS. 1A–1E and FIGS. 3A–3D. For example, cells can be induced to express receptors by exposure to substances such as hormones. The cells can then be homogenized and the receptor isolated from the homogenate using an affinity column comprising, for example, PP or another substance which is known to bind to the receptor. The resulting fractions can then be purified by contacting them with an ion exchange column, and determining which fraction contains receptor activity or binds anti-receptor antibodies. This method for preparing Y4 receptor uses recombinant DNA technology methods well known in the art. For example, isolated nucleic acid encoding Y4 receptor is inserted in a suitable vector, such as an expression vector. A suitable host cell, such as a bacterial cell, or a eukaryotic cell such as a yeast cell, is transfected with the vector. Y4 receptor is isolated from the culture medium by affinity purification or by chromatography or by other methods well known in the art.

This invention identifies for the first time a new receptor protein, its amino acid sequence, and its human gene. Furthermore, this invention describes a previously unrecognized group of receptors within the definition of a Y4 receptor. The information and experimental tools provided by this discovery are useful to generate new therapeutic agents, and new therapeutic or diagnostic assays for this new receptor protein, its associated mRNA molecule or its associated genomic DNA. The information and experimental tools provided by this discovery will be useful to generate new therapeutic agents, and new therapeutic or diagnostic assays for this new receptor protein, its associated mRNA molecule, or its associated genomic DNA.

Specifically, this invention relates to the first isolation of a human and a rat genomic clone encoding a Y4 receptor. A new human gene for the receptor identified herein as Y4 has been identified and characterized. In addition, the human Y4 receptor has been expressed in COS-7 cells. The pharmacological binding properties of the protein encoded have been determined, and these binding properties classify this protein as a novel NPY/PYY/PP receptor which we designate as a Y4 receptor. Mammalian cell lines expressing this Y4 receptor at the cell surface have been constructed, thus establishing the first well-defined, cultured cell lines with which to study this Y4 receptor.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Cloning and Sequencing of a human (Y4) Neuropeptide Receptor. A human placenta genomic library in λ dash II ($\approx 1.5 \times 10^6$ total recombinants; Stratagene, LaJolla, Calif.) was screened using overlapping transmembrane (TM) oligonucleotide probes (TM 1, 2, 3, 5 and 7) derived from the rat Y1 neuropeptide receptor gene (Eva, C. et al., 1990; GenBank accession No. Z11504). overlapping oligomers (TM1: nts. 198—251, (+) strand/5'-TTGCTTATGGGGCTGTGATTATTCT-TGGGGTCTCTGG AAACCTGG-3' (Sequence I.D. No. 3) and (-) strand/5'-TAGGATGATTATGATCAATGCCAGGTTTCCAGAGAC CCCAAGAAT-3' (Sequence I.D. No. 4); TM2: nts. 269–328, (+) strand/5'-AAAGAGATGAGGAATGTCACCAACATTCTGATCGT GAACCTCTCC-3' (Sequence I.D. No. 5) and (-)strand/5'-CAGCAAGTCTGAGAAGGA GAGGTTCAC-GATCAGAA TGTTGGTGAC-3' (Sequence I.D. No. 6); TM3: nts. 401–478, (+) strand/5'-TGCAAACTGAATCCTTTTGTGCAAT-GCGTCTCCATTA CAGTATCCATTTTCTCT-3' (Sequence I.D. No. 7) and (-) strand/5'-ACGTTCCACAGCGATGAGAACCA-GAGAGAAAATGG ATACTGTAATGGAGACGCA-3' (Sequence I.D. No. 8); TM5: nts. 716–778, (+) strand/5'-CTGCAGTATTTTGGCCCACTCTGTTTCATATTCATAT GCTAC-3' (Sequence I.D. No. 9) and (-)strand/5'-CAAGCGAATGTATATCTTGAAGTAGCATATGAATAT GAAACA-3' (Sequence I.D. No. 10); TM7: nts. 971–1045, (+) strand/5'-CTGCTCTGCCACCTCACGGCCATGATCTCCACCTGC GTCAACCCCATC-3' (Sequence I.D. No. 11) and (-) strand/5'-GAAATTTTTGTTCAGGAATCCATAAAAGATGGGGTT GACGCAGGTGGA-3' (Sequence I.D. No. 12); GenBank accession No. Z11504) were labeled with [$^{32}$P]dATP and [$^{32}$P]dCTP by synthesis with the large fragment of DNA polymerase. Hybridization was performed at low stringency conditions: 40° C. in a solution containing 25.0% formamide, 5× SSC (1× SSC is 0.15M sodium chloride, 0.15M sodium citrate), (1× Denhardt's solution (0.02% polyvinylpyrrolindone, 0.02% Ficoll, 0.02% bovine serum albumin), and 25 µg/µl sonicated salmon sperm DNA. The filters were washed at 40° C. in 0.1× SSC containing 0.1% sodium dodecyl sulfate and exposed at -70° C. to Kodak XAR film in the presence of an intensifying screen. Lambda phage clones hybridizing with the probes were plaque purified and DNA was prepared for Southern blot analysis (Southern, 1975; Sambrook et al., 1989). A Genomic clone hybridizing with all five of the rat Y1 TM probes, designated hp25a, was isolated using this method. For subcloning and further Southern blot analysis, the hp25a DNA was cloned into pUC18 (Pharmacia, Piscataway, N.J.). Nucleotide sequence analysis was accomplished by the Sanger dideoxy nucleotide chain termination method (Sanger et al., 1977) on denatured double-stranded plasmid templates, using Sequenase (US Biochemical Corp., Cleveland, Ohio).

Cloning and Sequencing of a rat NPY (Y4) neuropeptide receptor:

A rat spleen genomic library (Stratagene, La Jolla, Calif.) was screened using overlapping TM oligonucleotide probes (TM 1–7) derived from the nucleotide sequences corre sponding approximately to the TM regions of the amino acid sequence of the human Y4 receptor as shown in FIGS. 2A–2C. The overlapping oligomers used were as follows:

TM1: nts. #129–201,
(+) strand/5'-TCATCGTCACTTCCTACAGCATTGAGACTGTCGTGGGGGTCCTGGGT (Sequence I.D. No. 13) and
(−) strand/5'-ACAGTCACACACATCAGGCAGAGGTTACCCAGGACCCCCACGACAG (Seq. I.D. No. 14);

TM2: nts. #234–303,
(+) strand/5'-TGCTTATCGCCAACCTGGCCTTCTCTGACTTCCTCATGTGCCTCC (Seq. I.D. No. 15) and
(−) strand/5'-TAGACGGCGGTCAGCGGCTGGCAGAGGAGGCACATGAGGAAGTCA (Seq. I.D. No. 16);

TM3: nts. #348–417,
(+) strand/5'-TGTCGGCCTTCATCCAGTGCATGTCGGTGACGGTCTCCATCCTCT (Seq. I.D. No. 17) and
(−) strand/5'-CTCTCCAGGGCCACGAGGACGAGCGAGAGGATGGAGACCGTCACC (Seq. I.D. No. 18);

TM4: nts. #467–536,
(+) strand/5'-GCCTACCTGGGGATTGTGCTCATCTGGGTCATTGCCTGTGTCCTC (Seq. I.D. No. 19) and
(−) strand/5'-TGCTGTTGGCCAGGAAGGGCAGGGAGAGGACACAGGCAATGACCC (Seq. I.D. No. 20);

TMS: nts. #637–706,
(+) strand/5'-CATCTACACCACCTTCCTGCTCCTCTTCCAGTACTGCCTCCCACT (Seq. I.D. No. 21) and
(−) strand/5'-TGCATAACAGACCAGGATGAAGCCCAGTGGGAGGCAGTACTGGAA (Seq. I.D. No. 22);

TM6: nts. #800–870,
(+) strand/5'-CTGGTGGTGATGGTGGTGGCCTTTGCCGTGCTCTGGCTGCCTCTGC (Seq. I.D. No. 23) and
(−) strand/5'-CAGTCTTCCAGGCTGTTGAACACATGCAGAGGCAGCCAGAGCACG (Seq. I.D. No. 24);

TM7: NTS. #908–977,
(+) strand/5'-ATCTTCTTAGTGTGCCACTTGCTTGCCATGGCCTCCACCTGCGTC (Seq. I.D. No. 25) and
(−) strand/5'-TGAGAAAGCCATAGATGAATGGGTTGACGCAGGTGGAGGCCATGG (Seq. I.D. No. 26) were labeled with [$^{32}$P]-ATP and [$^{32}$P]-CTP by synthesis with the large fragment of DNA polymerase. Hybridization was performed at reduced stringency conditions: 40° C. in a solution containing 37.5% formamide, 10% dextran sulfate, 5× SSC, 1× Denhardt's solution, and 100 µg/ml of sonicated salmon sperm DNA. The filters were washed at 45° C. in 0.1× SSC containing 0.1% sodium dodecyl sulfate (SDS) and exposed at −70° C. to Kodak XAR film in the presence of an intensifying screen. Lambda phage clones hybridizing to the probes were plaque purified by successive plating and rescreening. A genomic clone hybridizing with all seven human Y4 receptor TM probes, designated rs16b, was isolated using this method. For expression and sequence analysis, a 2.0 kb BamHI/HindIII fragment of rs16b was subcloned into the corresponding polylinker sites of a pcEXV-3 eukaryotic expression vector (Miller and Germain, 1986) modified to include a polylinker with EcoRI, SstI, ClaI, KpnI, SmaI, XbaI, BamHI, SalI and HindIII restriction sites and designated EXJ.RH. Nucleotide sequence analysis was accomplished by the Sanger dideoxy nucleotide chain-termination method (Sanger, 1977) on double stranded plasmid templates, using Sequenase (U.S. Biochemical Corp., Cleveland, Ohio).

Transient Transfection: The entire coding region of hp25a (1127 bp), including 680 bp of 5' untranslated (5' UT) and 205 bp of 3' untranslated sequence (3' UT), was cloned into the BamHI and EcoRI sites of the polylinker-modified eukaryotic expression vector pCEXV-3 (Miller et al., 1986), called EXJ.HR (J.B., unpublished data). Monkey kidney cells (Cos-7) were transiently transfected with plasmid hp2Sa/EXJ (expression vector containing the hp25a receptor gene) using DEAE dextran methodology (reagents obtained from Specialty Media, Lavellette, N.J.).

The plasmid rs16b/EXJ (the expression vector containing the rs16b receptor gene), was transiently transfected into Cos-7 cells using similar methods, as were the human Y1 receptor (Larhammar, 1992) and the human Y2 receptor. The cloned Y2 receptor was disclosed in U.S. patent application Ser. No. 08/192,288 filed on Feb. 2, 1994, currently pending, the foregoing contents of which are hereby incorporated by reference.

Stable Transfection

Human Y4 receptors were co-transfected with a G-418 resistant gene into the mouse embryonic NIH-3T3 cell line by a calcium phosphate transfection method (Cullen, 1987). Stably transfected cells were selected with G-418. Human Y4 receptors were similarly transfected into mouse fibroblast LM(tk−) cells.

Cell culture: COS-7 cells were grown on 150 mm plates (Corning) in D-MEM with supplements (Dulbecco's Modified Eagle Medium with 10% bovine calf serum, 2 mM glutamine, 100 units/ml penicillin/80 units/ml streptomycin) at 37° C., 5% $CO_2$. Stock plates of COS-7 cells were trypsinized and split 1:6 every 3–4 days. SK-N-Be(2) human neuroblastoma cells were grown similarly in 225 cm$^2$ flasks (Co-star) using 50% Eagle's Modified Essential Media, 50% Ham's Nutrient Mixture F-12, 15% fetal bovine serum, 2 mM glutamine, 100 units/ml penicillin/80 units/ml streptomycin, and 1% non-essential amino acids. Stock flasks of SK-N-Be(2) cells were trypsinized and split 1:10 every 7 days.

Mouse embryonic NIH-3T3 cells were grown on 150 mm plates in Dulbecco's Modified Eagle Medium (DMEM) with supplements (10% bovine calf serum, 4 mM glutamine, 100 units/ml penicillin/100 µg/ml streptomycin) at 37° C., 5% $CO_2$. Stock plates of NIH-3T3 cells were trypsinized and split 1:15 every 3–4 days. Mouse fibroblast LM(tk−) cells were grown on 150 mm plates in Dulbecco's Modified Eagle Medium (DMEM) with supplements (10% bovine calf serum, 4 mM glutamine, 100 units/ml penicillin/100 µg/ml streptomycin) at 37° C., 5% $CO_2$. Stock plates of LM(tk−) cells were trypsinized and split 1:10 every 3–4 days.

Cell culture media and supplements were from Specialty Media (Lavallette, N.J.). Cell culture plates (150 mm) were from Corning (Corning, N.Y.). Cell culture flasks (225 cm²) and polypropylene microtiter plates were from Co-star (Cambridge, Mass.).

Membrane Harvest: Membranes were harvested from COS-7 cells 48 hours after transfection and from SK-N-Be (2) seven days after splitting. Adherent cells were washed twice in ice-cold phosphate buffered saline (138 mM NaCl, 8.1 mM $Na_2HPO_4$, 2.5 mM KCl, 1.2 mM $KH_2PO_4$, 0.9 mM $CaCl_2$, 0.5 mM $MgCl_2$, pH 7.4) and lysed by sonication in ice-cold hypotonic buffer (20 mM Tris-HCl, 5 mM EDTA, pH 7.7). Large particles and debris were cleared by low speed centrifugation (200×g, 10 min, 4° C.). Membranes were collected from the supernatant fraction by high speed centrifugation (32,000×g, 18 min, 4° C.), washed with ice-cold hypotonic buffer, and collected again by high speed centrifugation (32,000×g, 18 min, 4° C.). The final membrane pellet was resuspended by sonication into a small volume (~500 μl) of ice-cold binding buffer (10 mM NaCl, 20 mM HEPES, 0.22 mM $KH_2PO_4$, 1.26 mM $CaCl_2$, 0.81 mM $MgSO_4$, pH 7.4). Protein concentration was measured by the Bradford method (Bradford, 1976) using Bio-Rad Reagent, with bovine serum albumin as a standard.

Radioligand Binding to Membrane Suspensions: Membrane suspensions were diluted in binding buffer supplemented with 0.1% bovine serum albumin and 0.1% bacitracin to yield an optimal membrane protein concentration: ~0.02 mg/ml for human Y1 receptors, ~0.015 mg/ml for hp25a receptors, and ~0.25 mg/ml for SK-N-Be(2). (Under these conditions, $^{125}$I-PYY bound by membranes in the assay was less than 10% of $^{125}$I-PYY delivered to the sample.) $^{125}$I-PYY and non-labeled peptide competitors were also diluted to desired concentrations in supplemented binding buffer. Individual samples were then prepared in 96-well polypropylene microtiter plates by mixing membrane suspensions (200 ul), $^{125}$I-PYY (25 ul), and non-labeled peptides or supplemented binding buffer (25 ul). Samples were incubated in a 30° C. water bath with constant shaking for 120 min. Incubations were terminated by filtration over Whatman GF/C filters (pre-coated with polyethyleneimine and air-dried before use). Filter-trapped membranes were counted for $^{125}$I in a gamma counter. Non-specific binding was defined by 100 nM human PP for hp25a receptors and by 100 nM NPY for Y1 and SK-N-Be(2) receptors. Specific binding in time course and competition studies was typically 80%; most non-specific binding was associated with the filter. Binding data were analyzed using nonlinear regression and statistical techniques available in the GraphPAD InPlot package (San Diego, Calif). Porcine $^{125}$I-PYY was from New England Nuclear (Boston, Mass). NPY and related peptide analogs were from either Bachem California (Torrance, Calif.) or Peninsula (Belmont, Calif.). Whatman GF/C filters were from Brandel (Gaithersburg, Md.). Bio-Rad Reagent was from Bio-Rad (Hercules, Calif.). Bovine serum albumin and bacitracin were from Sigma (St. Louis. Mo.). All other materials were reagent grade. Functional Assay: Radioimmunoassay of cAMP Stably transfected cells were seeded into 96-well microtiter plates and cultured until confluent. To reduce the potential for receptor desensitization, the serum component of the media was reduced to 1.5% for 4 to 16 hours before the assay. Cells were washed in Hank's buffered saline, or HBS (150 mM NaCl, 20 mM HEPES, 1 mM $CaCl_2$, 5 mM KCl, 1 mM $MgCl_2$, and 10 mM glucose) supplemented with 0.1 bovine serum albumin plus 5 mM theophylline and pre-equilibrated in the same solution for 20 min at 37° C. in 5% $CO_2$. Cells were then incubated 5 min with 10 μM forskolin and various concentrations of receptor-selective ligands. The assay was terminated by the removal of HBS and acidification of the cells with 100 mM HCl. Intracellular cAMP was extracted and quantified with a modified version of a magnetic bead-based radioimmunoassay (Advanced Magnetics, Cambridge, Mass.). The final antigen/antibody complex was separated from free $^{125}$I-cAMP by vacuum filtration through a PVDF filter in a microtiter plate (Millipore, Bedford, Mass.). Filters were punched and counted for $^{125}$I in a Packard gamma counter. Binding data were analyzed using nonlinear regression and statistical techniques available in the GraphPAD Prism package (San Diego, Calif.).

Functional Assay: Intracellular Calcium Mobilization

The intracellular free calcium concentration was measured by microspectroflourometry using the fluorescent indicator dye Fura-2/AM. Stably transfected cells were seeded onto a 35 mm culture dish containing a glass coverslip insert. Cells were washed with HBS and then loaded with 100 μl of Fura-2/AM (10 μM) for 20 to 40 min. After washing with HBS to remove the Fura-2/AM solution, cells were equilibrated in HBS for 10 to 20 min. Cells were then visualized under the 40× objective of a Leitz Fluovert FS microscope and fluorescence emission was determined at 510 nM with excitation wave lengths alternating between 340 and 380 nM. Raw fluorescence data were converted to calcium concentrations using standard calcium concentration curves and software analysis techniques.

Tissue Localization and Gene Expression: Reverse Transcriptase PCR

Human tissues (obtained from National Disease Research Interchange) were homogenized and total RNA extracted using guanidine isothiocyanate/CsCl cushion method (Kingston, 1987). RNA was treated with DNase to remove any contaminating genomic DNA. cDNA was prepared from total RNA with random hexanucleotide primers using reverse transcriptase (Superscript II; BRL). An aliquot of the first strand cDNA (250 ng of total RNA) was amplified in a 50 μl PCR reaction mixture (200 μM dNTPs final concentration) containing 1.2 U of Taq polymerase in the buffer supplied by the manufacturer (Perkin-Elmer Corporation), and 1 μM of primers, using a program consisting of 30 cycles of 94° C./2', 68° C./2', and 72° C./3', with a pre- and post-incubation of 95° C./5' and 72° C./10' , respectively. PCR primers for human Y4 were designed against the human Y4 sequence in the third intracellular loop and carboxy terminal regions: 5'-CGCGTGTTTCACAAGGGCACCTA-3' (SEQ ID NO: 29) and 5'-TGCCACTTAGCCTCAGGGACCC-3' (SEQ ID NO: 30), respectively.

The PCR products were run on a 1.5% agarose gel and transferred to charged nylon membranes (Zetaprobe GT, BioRad), and analyzed as Southern blots. Hybridization probes corresponding to the receptor region flanked by PCR primers were prepared (5'-TCCGTATGTACTGTGGACAGGGGCAGAT-GCTCCGAC
TCCTCCAGG-3' (SEQ ID NO: 31)) and pre-screened for the absence of cross-reactivity with human Y1 and human Y2 receptor subtypes. Filters were hybridized with end-labeled [γ-$^{32}$P]ATP internal probe to the PCR primers, washed under high stringency, and exposed to Kodak XAR film in the presence of an intensifying screen, as described above. Similar PCR and Southern blot analysis were conducted with primers and probe directed to the housekeeping gene, glyceraldehyde-3-phosphate dehydrogenase (Clontech, Palo Alto, Calif.), and demonstrated that equal amounts of cDNA from the different tissues were being assayed for NPY expression.

Results

A human genomic placenta library was screened, under reduced stringency conditions, with oligonucleotide probes directed to the first, second, third, fifth, and seventh transmembrane regions of the rat Y1 neuropeptide receptor gene (Eva, C. et al., 1990; GenBank accession No. Z11504). Positively-hybridizing clones (≈100–150) were isolated, plaque-purified and characterized by Southern blot analysis and sequencing. One clone, hp25a, contained a 1.3 kb PstI fragment which hybridized with the rat Y1-derived oligonucleotide probes and was subsequently subcloned into a pUC vector. DNA sequence analysis indicated greatest homology to the rat and human Y1 receptor genes. This clone was a partial intronless gene fragment, encoding part of the third intracellular loop through the carboxyl terminus, including a termination codon.

In order to obtain a full-length clone, a 2.0 kb BamHI/EcoRI hybridizing fragment, containing the entire coding region, which was intronless, was subcloned into an expression vector and sequenced. The genomic full-length construct in the expression vector (called hp25a/EXJ) contains an open reading frame of 1127 bp, with 680 bp of the predicted 5' UT and 205 bp of predicted 3' UT sequence, and encodes a protein of 375 aa in length, with a relative molecular mass of ≈41,000 daltons. Hydropathy analysis of the protein is consistent with a putative topography of seven transmembrane domains, indicative of the G protein-coupled receptor family.

Initial sequence analysis revealed that clone hp25a/EXJ contained several conserved structural features/residues found among the members of the neuropeptide receptor family, including two alycines and asparagine in TM1 (positions 55, 58 and 59, respectively, in FIGS. 2A–2C), an asparagine, leucine and aspartic acid in TM2 (positions 82, 83, and 87, respectively, in FIGS. 2A–2C), a serine and leucine in TM3 (positions 128 and 132, respectively, in FIGS. 2A–2C), a tryptophan and proline in TM4 (positions 164 and 173, respectively, in FIGS. 2A–2C), a tyrosine and proline in TM5 (positions 223 and 226, respectively, in FIGS. 2A–2C), a phenylalanine, tryptophan, and proline in TM6 (positions 275, 279, and 281, respectively, in FIGS. 2A–2C), and a serine, threonine, asparagine, and proline in TM7 (positions 315, 316, 319, and 320, respectively, in FIGS. 2A–2C). Other features of this human hp25a receptor gene are the presence of three potential sites for N-linked glycosylation in the amino terminus (asparagine residues 2, 19, and 29; FIGS. 1A–1E) and the presence of several serines and threonines in the carboxyl terminus and intracellular loops, which may serve as sites for potential phosphorylation by protein kinases.

A comparison of nucleotide and peptide sequences of clone hp25a/EXJ with sequences contained in the Genbank/EMBL databases reveals that the clone is most related to the rat, mouse and human Y1 receptor genes and proteins (see FIGS. 2A–2C). The hp25a clone exhibits 42% overall amino acid identity with the human NPY-1 receptor and 55% identity when comparing only the transmembrane domains between hp25a and Y1. The comparison of the individual amino acid residues in the TM domains between hp25a and Y1 reveal <30%, 57%, 57%, 57%, 52%, 63%, and 71% identity in the corresponding one through seven TM regions, repectively. The hp25a clone hybridized only with the TM7-specific probe from the original set of rat-derived TM probes originally used to screen the library which is consistent with the hp25a clone sharing the highest degree of amino acid identity with the TM7 domain of the rat Y1 receptor.

A rat homolog of the human Y4 receptor, designated rs16b, was isolated from a rat spleen genomic library using probes derived from the transmembrane regions of the human Y4 receptor. The nucleotide sequence of rs16b is 80% identical in the coding region to the nucleotide sequence of the human Y4 receptor, and encodes a protein 375 amino acids in length (FIGS. 3A–3D). The rs16b clone exhibits 75% overall amino acid identity with the human Y4 amino acid sequence, and in the putative transmembrane domains (TMs), the protein predicted by rs16b exhibits 84% amino acid identity with the human Y4 receptor. This degree of primary amino acid sequence identity is lower than is typically seen for species homologues, and suggests that rat and human Y4 receptors may exhibit functional variations as well. The predicted intracellular loop between TMs V and VI is particularly divergent, showing only 56% amino acid identity between rat and human Y4; divergence in this region could potentially mediate differences in G-protein coupling between the rat and human receptors. The primary sequences of rat and human Y4 receptors also show differences in their patterns of sequence motifs for casein kinase II phosphorylation, N-myristoylation, and protein kinase C phosphorylation; these sites could potentially mediate differences in the function or regulation of the two receptors.

Monkey kidney cells transiently expressing the gene encoding the hp25a receptor were used for pharmacological evaluation. Membranes harvested from transiently transfected Cos-7 cells exhibited high affinity, saturable [$^{125}$I] PYY binding. The time course of specific binding was measured in the presence of 0.06 rM $^{125}$I-PYY (FIG. 5). The association curve was monophasic, with a an observed association rate ($K_{obs}$) of 0.12±0.02 min$^{-1}$ and a $t_{1/2}$ of 6 min; equilibrium binding was 95% complete within 26 min and 100% complete within 50 min (n=3). For comparison, we also measured the time course of binding to human Y1 receptors transiently expressed in COS-7 cells. The association curve was monophasic, with a $K_{obs}$ of 0.06±0.02 min$^{-1}$ and a $t_{1/2}$ of 12 min; equilibrium binding was 95% complete within 51 min and 100% complete within 90 min (n=3) (data not shown). The different patterns of radioligand association for hp25a and human Y1 receptors suggest novel mechanisms of receptor/ligand interaction.

Figure 6B:
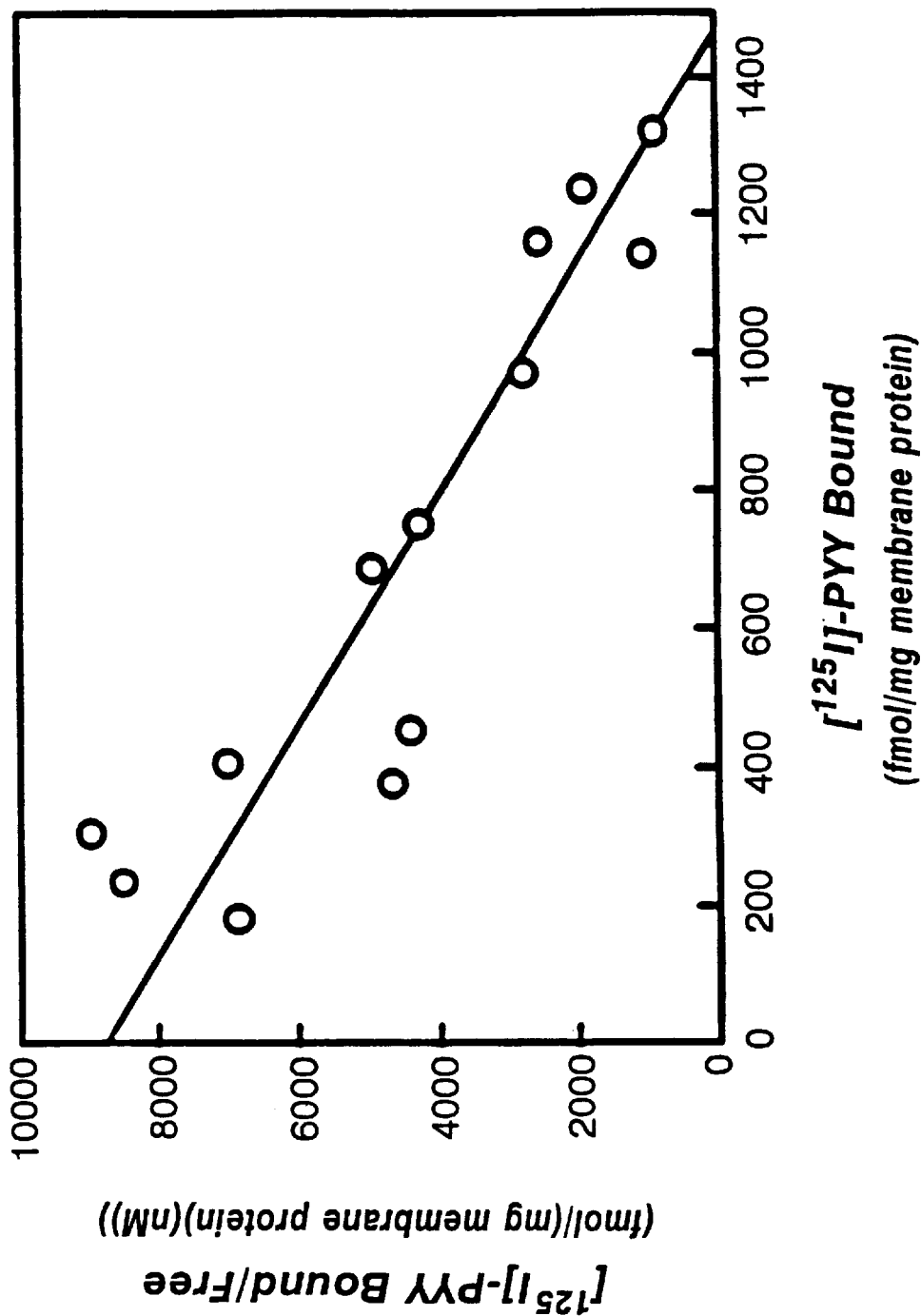

Saturation binding data for $^{125}$I-pYY were fit to a one-site model with an apparent $K_d$ of 0.11±0.01 nM and an apparent $B_{max}$ of 1.42±0.05 pmol/mg membrane protein, corresponding to approximately 1.4×10$^5$ receptors/cell (n=4; FIGS. 6A and 6B). Given that the transfection efficiency was 20–30% (data not shown), the receptor density on transfected cells was probably closer to 7×10$^5$/cell. Membranes from mock-transfected cells, when prepared and analyzed in the same way as those from hp25a-transfected cells, displayed no specific binding of $^{125}$I-PYY. We conclude that the $^{125}$I-PYY binding sites observed under the described conditions were derived from the hp25a construct.

Figure 7:
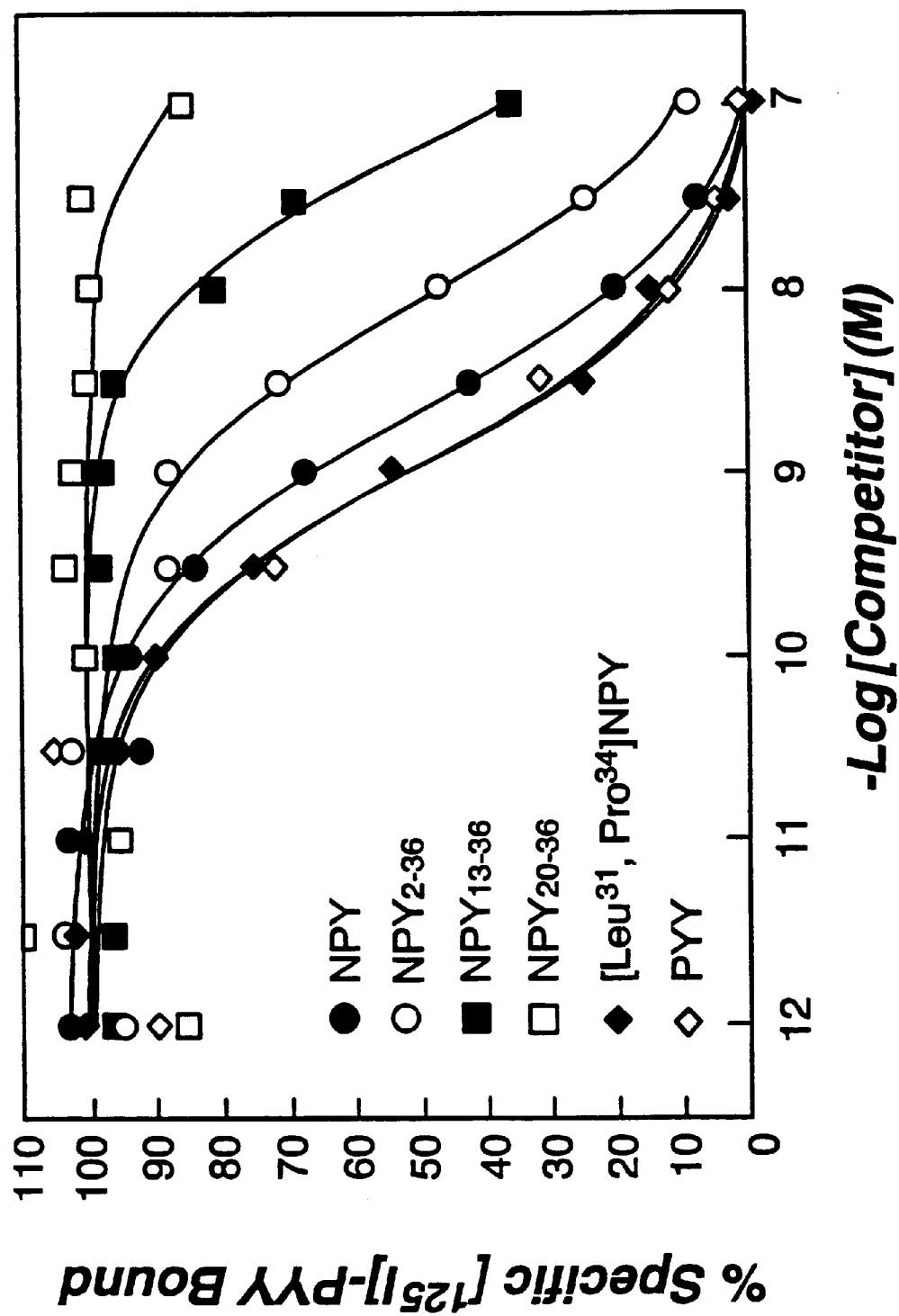

The pharmacological profile of hp25a was defined by membrane binding assays. The receptor was probed for features of all well characterized pancreatic polypeptide family receptors including Y1, Y2, Y3, and PP. The rank order of affinity for several peptide analogs was derived from competitive displacement of $^{125}$I-PYY (FIG. 7 and Table 2). The hp25a receptor was compared with two model systems: 1) the cloned human Y1 receptor (Larhammar et al., 1992; Herzog et al., 1992) transiently expressed in COS-7 cells, and 2) the Y2-like receptor population expressed by human SK-N-Be(2) neuroblastoma cells (Wahlestedt et al., 1991; Dumont et al., 1992). No models for human Y3 and human PP receptors have been described.

PP bound to hp25a with extremely high affinity ($K_i$=0.029 nM) and dramatic selectivity: PP was >6000-fold selective for hp25a over human Y1 receptors ($K_i$=200 nM) and SK-N-Be(2) receptors ($K_i$>300 nM). This profile suggests that hp25a could function selectively as a PP receptor in vivo. The data further indicated, however, that hp25a bound quite well to human NPY ($K_i$=1.4 nM) and even better to human PYY ($K_i$=0.62 nM). These $K_i$ values, while lower than the $K_i$ for PP, are comparable to the effective concentrations of NPY and PYY from numerous physiological and pharmacological studies (Dumont, 1992). In our investigation, SK-N-Be(2) receptors bound human NPY and human PYY in the same rank order as hp25a but with 5- to 10-fold higher affinity, whereas human Y1 receptors bound human NPY and human PYY in the opposite rank order with 5- to 30-fold higher affinity. Hydrolysis of the carboxy terminal amide to free carboxylic acid, as in human NPY free acid, was disruptive for binding to all receptors. A requirement for a carboxy terminal amide appears to be a common structural feature of all pancreatic polypeptide family peptide/receptor interactions.

Fuhlendorff and co-workers replaced Ile$^{31}$ and Gln$^{34}$ in NPY with the corresponding residues from PP to create [Leu$^{31}$,Pro$^{34}$]NPY, which is commonly used to distinguish Y1 from Y2 receptors (Fuhlendorff, 1990). Human [Leu$^{31}$, Pro$^{34}$]NPY displayed >2300-fold selectivity for human Y1 receptors over SK-N-Be(2), but only 5-fold selectivity for human Y1 receptors over hp25a. Human [Leu$^{31}$,Pro$^{34}$]NPY was a better ligand for hp25a ($K_i$=0.60 nM) than was human NPY itself ($K_i$=1.4 nM). This is possibly a reflection of the way in which [Leu$^{31}$,Pro$^{34}$]NPY mimics PP at positions 31 and 34. In contrast, the [Leu$^{31}$,Pro$^{34}$]NPY analog was well tolerated by the human Y1 receptor ($K_i$=0.13 nM), but not preferred over the parent peptide ($K_i$=0.049 nM).

hp25a displayed an intermediate level of sensitivity to N-terminal deletions of NPY and PYY, less so than human Y1 receptors. Removing Tyr$^1$ from porcine NPY resulted in a 29-fold loss in affinity for human Y1 receptors when compared with the full length parent peptide. The same modification decreased affinity 4-fold for hp25a receptors and 3-fold for SK-N-Be(2) receptors. It is interesting in this regard that human PP contains Ala$^1$; the Tyr$^1$ of NPY may not play much of a role in receptor recognition. Truncation to NPY$_{13-36}$ decreased affinity 1000-fold for human Y1 receptors, 33-fold for hp25a, and 4-fold for SK-N-Be(2) receptors. Further truncation to porcine NPY$_{22-36}$ decreased affinity 3500-fold for human Y1 receptors, 120-fold for hp25a, and 11-fold for SK-N-Be(2) receptors. In this regard, the hp25a receptor shares features of both Y1- and Y2-like pharmacology, as would be expected if the N-terminal region of porcine NPY were only moderately involved in receptor recognition.

An important structural difference between human PP, human PYY and human NPY is that both human NPY and PYY contain Gln$^{34}$, whereas human PP contains Pro$^{34}$. When Gln$^{34}$ in NPY was replaced with Pro$^{34}$ (as in the analog [Leu$^{31}$, Pro$^{34}$]NPY), an increase in binding affinity for the human Y4 receptor was observed. A similar increase in binding affinity was detected when Gln$^{34}$ of PYY was replaced with Pro$^{34}$, supporting the proposal that PP-like peptides are preferred by the Y4 receptor. Replacement of Pro$^{34}$ in human PP by Gln$^{34}$ (as in [Ile$^{31}$, Gln$^{34}$]PP) caused very little change in PP binding affinity, however, suggesting that in the case of PP there are significant contributions to binding affinity from other regions of the peptide structure.

Applicants further extended the structure/activity data for human PP fragments (PP$_{2-36}$, PP$_{13-36}$, PP$_{20-36}$, PP$_{27-36}$, and PP$_{31-36}$) PP binding was unaffected by N-terminal truncation to PP$_{2-36}$, but further truncation to PP$_{13-36}$ and beyond was disruptive. The shortest PP fragment tested, PP$_{31-36}$, bound selectively to the Y4 receptor with $K_i$=350 nM, and hydrolysis of the C-terminal amide was detrimental ($K_i$>10,000 nM for human PP$_{31-36}$ free acid), as reported earlier for NPY. We conclude that the binding of PP to the Y4 receptor resembles the binding of NPY to the Y1 receptor, in that 1) Pro$^{34}$ is well-tolerated and 2) both ends of the peptide are required for optimal binding activity. This is in contrast to the Y2 binding model, in which 1) Pro$^{34}$ is not well-tolerated and 2) the N-terminal region of NPY does not contribute significantly to binding affinity. Note also that the Y2-selective ligands human PYY$_{3-36}$ and C2-NPY display relatively low affinity for the human Y4 receptor.

Additionally, the binding of the tetrapeptide invertebrate neurotransmitter Phe-Met-Arg-Phe-Amide (FMRF-amide) was investigated. This peptide has been shown to mimic several functions of NPY including the stimulation of food intake in rats (Robert, 1988). FMRFamide bound selectively to the Y4 receptor with a $K_i$ value of 4000 nM. A closely related derivative, Phe-Leu-Arg-Phe-amide (FLRFamide), displayed improved Y4 binding affinity ($K_i$=750 nM) while maintaining selectivity. We also investigated the binding of [D-Trp$^{32}$]NPY. This peptide was reported to stimulate food intake when injected into rat hypothalamus, and also to attenuate NPY-induced feeding in the same paradigm (Balasubramaniam, 1994). [D-Trp$^{32}$]NPY displayed relatively low binding affinity for the human Y4 receptor as well as for the human Y1 and Y2 receptor subtypes. Data for these and other new peptides not included in the original patent filing are listed in Table 3.

Untransfected NIH-3T3 and LM(tk-) were pre-screened for specific $^{125}$I-PYY binding and found to be negative (data not shown). After co-transfection with the human Y4 cDNA and a G418-resistant gene and selection with G-418, surviving colonies were screened for specific binding of 125I-PYY. Two positive clones were identified and isolated for further study (NIH-3T3 hY4 clone #5 and LM(tk-) hY4 clone #3). The binding of $^{125}$I-PYY to membranes from the NIH-3T3 stable clone was saturable over a radioligand concentration range of 0.5 pM to 2.5 nM. Binding data were fit to a one-site binding model with an apparent $K_d$ of 0.17 nM +0.005 and a receptor density of 350±80 fmol/mg membrane protein (mean±s.e.m., n=2). The LM(tk-) clone displayed an estimated receptor density of 7 fmol/mg membrane protein during the primary selection screen and was not analyzed further in a saturation assay.

Figure 8:
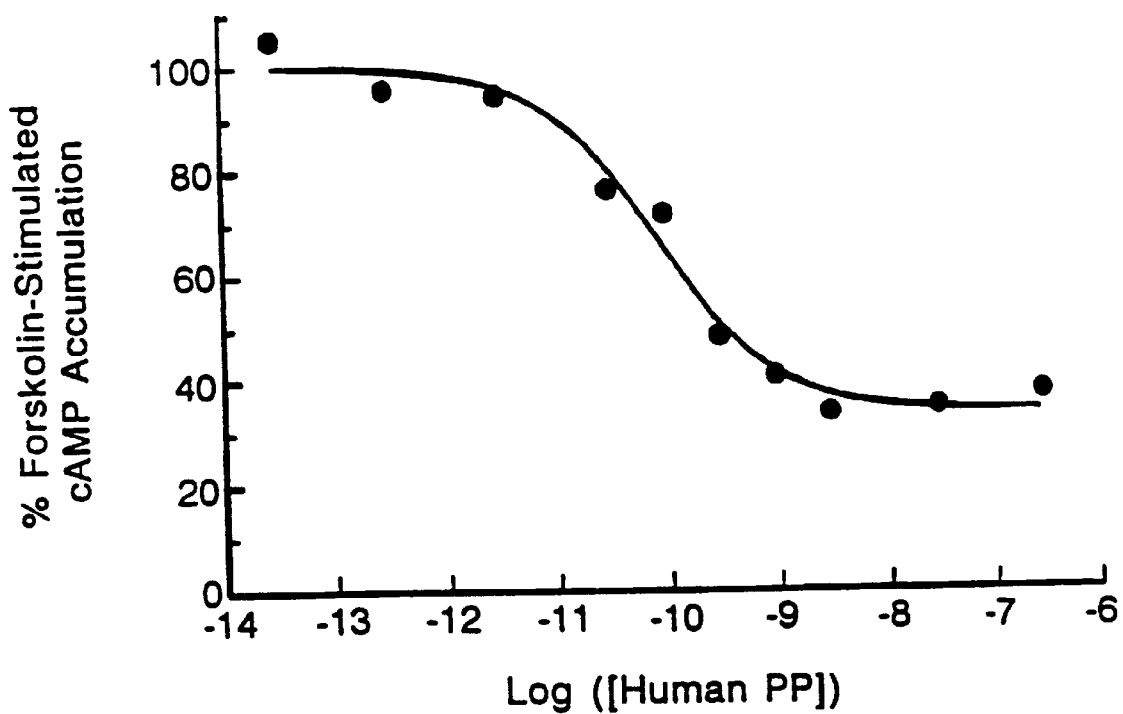

Activation of all Y-type receptors described thus far is thought to involve coupling to pertussis toxin-sensitive G-proteins which are inhibitory for adenylate cyclase activity ($G_i$ or $G_o$) (Wahlestedt and Reis, 1993). Based on these prior observations, we investigated the ability of PP to inhibit forskolin-stimulated cAMP accumulation in LM(tk-) cells stably expressing the human Y4 receptor. Incubation of intact cells with 10 μM forskolin produced ~10-fold increase in cAMP accumulation over a 5 minute period, as determined by radioimmunoassay. Simultaneous incubation with human PP decreased the forskolin-stimulated cAMP accumulation by 67% in stably transfected LM(tk-) cells (FIG. 8) but not in untransfected cells (data not shown). Applicants conclude that human Y4 receptor activation can result in decreased cAMP accumulation, very likely through inhibition of adenylate cyclase activity.

Peptides selected for their ability to bind to the transiently expressed human Y4 receptor were investigated for their ability to activate the human Y4 in the cAMP assay (Table 4). Note that both human PP and human PP$_{2-36}$ bound the Y4 receptor with a K$_i$ value of 0.06 nM, and that each displayed comparable activity in the cAMP assay with closely matching EC$_{50}$ values of 0.09 nM and 0.08 nM, respectively. The truncated PP fragments PP$_{27-36}$ and PP$_{31-36}$ were relatively weak ligands in the binding assay and were also less than 50% as effective as the full length PP in reducing forskolin-stimulated cAMP, thereby acting as partial agonists. Similarly, both NPY and PYY (which deviate from PP primarily in the N-terminal regions) yielded EC$_{50}$ values >10-fold larger than their K$_i$ values. Receptor activation (more so than binding) may therefore depend heavily upon N-terminal PP structure. The functional activity of the reported feeding behavior modulator [D-Trp$^{32}$]NPY was also investigated. Consistent with this peptide's low binding affinity for the human Y4 receptor, no functional activity of the peptide was detected at concentrations up to 0.3 uM (see Table 4), or when tested at 0.3 uM for antagonism of the PP functional response (data not shown).

The intracellular free calcium concentration was markedly increased in LM(tk−) cells stably transfected with the human Y4 receptor after application of 100 nM human PP (Δ [Ca$^{2+}$]$_i$=325 nM; FIG. 9). The response to 100 nM NPY was relatively small (Δ [Ca$^{2+}$]$_i$=68 nM). Untransfected LM(tk−) cells were unresponsive to either peptide (data not shown). When human PP was further analyzed in a concentration/response curve, the maximum Δ [Ca$^{2+}$]$_i$ measured was 334 nM and the EC$_{50}$ was 35 nM (FIG. 9, Inset). This greater activity of PP over NPY is consistent with the pharmacological profiles derived from both binding and cAMP assays described above. The calcium mobilization assay thereby provides a second pathway through which Y4 receptor activation can be measured.

Y4 mRNA was detected by PCR techniques in a broad range of human tissues. Relatively intense hybridization signals were detected in total brain, coronary artery, and ileum, suggesting a potential role for Y4 receptors in CNS function, cardiovascular regulation, and gastrointestinal physiology (Table 5).

The cDNA corresponding to the rat Y4 homolog was transiently expressed in COS-7 cells for membrane binding studies. The binding of $^{125}$I-PYY to the rat Y4 receptor was saturable over a radioligand concentration of 0.5 pM to 2.5 nM. Binding data were fit to a one-site model with an apparent K$_d$ of 0.15 nM±0.005 and a receptor density of 275±3 fmol/mg membrane protein (mean±s.e.m., n=2). As determined by using peptide analogs within the pancreatic polypeptide family, the rat Y4 pharmacological profile bears a resemblance to the human Y4 receptor; there are several interesting exceptions, however, including frog PP, salmon PP, human PP$_{31-36}$, and avian PP, each of which discriminated ~10-fold between the rat and human receptor subtypes (Table 6). The differences may reflect the fact that PP is not well conserved among species relative to NPY and PYY; hence the species homologs of PP are likely to exhibit more variability in ligand binding.

In summary, both the human Y4 receptor and the rat Y4 receptor displayed features unique among the neuropeptide receptors, exhibiting a profile which is divergent from their closest relatives, Y1 or Y2, in that each binds optimally to PP rather than to NPY or PYY (see Tables 1, 2 and 6). Unlike the Y1 and Y2 receptor models, the Y4 receptor appears to be a reasonable target for all three peptide ligands.

TABLE I

Pharmacologically defined receptors for NPY and related pancreatic polypeptides.
Rank orders of affinity are based on published reports of binding and functional data (Wahlestedt et al., 1991; Schwartz et al., 1990; Wahlestedt et al., 1993; Dumont et al., 1992). Missing peptides in the series reflect a lack of published information.

| Receptor | Affinity (-pK$_i$ or -pEC$_{50}$) | | | | | |
|---|---|---|---|---|---|---|
| | 11 to 10 | 10 to 9 | 9 to 8 | 8 to 7 | 7 to 6 | <6 |
| Y1 | NPY<br>PYY<br>[Leu$^{31}$,Pro$^{34}$]NPY | | NPY$_{2-36}$ | NPY$_{13-36}$ | PP | |
| Y2 | | PYY<br>NPY<br>NPY$_{2-36}$ | NPY$_{13-36}$ | | | [Leu$^{31}$,Pro$^{34}$]NPY<br>PP |
| Y3 | | NPY | [Pro$^{34}$]NPY | NPY$_{13-36}$<br>PP | | PYY |
| PP | PP | | [Leu$^{31}$,Pro$^{34}$]NPY | | | NPY |

TABLE 2

Pharmacological profile of the hp25a receptor.
Binding data reflect competitive displacement of $^{125}$I-PYY from membranes of COS-7 cells transiently expressing hp25a receptors. Peptides were tested at concentrations ranging from 0.001 nM to 100 nM. IC$_{50}$ values corresponding to 50% displacement were determined by nonlinear regression analysis and converted to K$_i$ values according to the equation, K$_i$ = IC$_{50}$/(1 + [L]/K$_d$), where [L] is the $^{125}$I-PYY concentration and K$_d$ is the equilibrium dissociation constant of $^{125}$I-PYY. The data shown are representative of at least two independent experiments.

| Competitor | Human Y1, K$_1$ (nM) | hp25a, K$_i$ (nM) | SK-N-Be(2), K$_i$ (nM) |
|---|---|---|---|
| human PP | 200 ± 68 | 0.029 ± 0.006 | >300 |
| human [Leu$^{31,Pro}$34]NPY | 0.13 ± 0.02 | 0.60 ± 0.09 | >300 |
| human PYY | 0.085 ± 0.021 | 0.62 ± 0.15 | 0.11 ± 0.02 |
| porcine NPY | 0.049 ± 0.001 | 1.2 ± 0.2 | 0.28 ± 0.04 |
| human NPY | 0.049 ± 0.009 | 1.4 ± 0.1 | 0.13 ± 0.02 |
| porcine NPY$_{2-36}$ | 1.4 ± 0.2 | 4.4 ± 1.3 | 0.41 ± 0.09 |
| porcine NPY$_{13-36}$ | 51 ± 16 | 39 ± 5 | 1.8 ± 0.4 |
| porcine PYY$_{13-36}$ | 32 ± 7 | 47 ± 6 | 0.86 ± 0.14 |
| porcine NPY$_{16-36}$ | 45 ± 4 | 54 ± 2 | 5.0 ± 0.5 |
| porcine NPY$_{18-36}$ | 28 ± 5 | 63 ± 7 | 2.1 ± 0.5 |
| human NPY free acid | >300 | 79 ± 17 | 280 ± 120 |
| porcine NPY$_{20-36}$ | 62 ± 6 | 100 ± 20 | 3.1 ± 0.6 |
| porcine NPY$_{22-36}$ | 170 ± 30 | 140 ± 63 | 3.2 ± 0.6 |

TABLE 2-continued

Pharmacological profile of the hp25a receptor.
Binding data reflect competitive displacement of $^{125}$I-PYY from membranes of COS-7 cells transiently expressing hp25a receptors. Peptides were tested at concentrations ranging from 0.001 nM to 100 nM. $IC_{50}$ values corresponding to 50% displacement were determined by nonlinear regression analysis and converted to $K_i$ values according to the equation, $K_i = IC_{50}/(1 + [L]/K_d)$, where [L] is the $^{125}$I-PYY concentration and $K_d$ is the equilibrium dissociation constant of $^{125}$I-PYY. The data shown are representative of at least two independent experiments.

| Competitor | Human Y1, $K_i$ (nM) | hp25a, $K_i$ (nM) | SK-N-Be(2), $K_i$ (nM) |
|---|---|---|---|
| porcine NPY$_{26-36}$ | >300 | >300 | 70 ± 7 |

Table 3: human Y4 receptor vs. Y-type receptors cloned from human.

Binding data reflect competitive displacement of $^{125}$I-PYY from membranes of COS-7 cells transiently expressing human Y1, human Y2, and human Y4 receptors. $IC_{50}$ values corresponding to 50% displacement were determined by nonlinear regression analysis and converted to $K_i$ values according to the equation Chang-Prusoff equation, $K_i = IC_{50}/(1+[L]/Kd)$, where [L] is the $^{125}$I-PYY concentration and $K_d$ is the equilibrium dissociation constant of $^{125}$I-PYY. Any peptide not included in the original patent filing is referred to as a "new peptide".

TABLE 3

| Peptide | Y1 | Y2 | Y4 | Comments |
|---|---|---|---|---|
| PP, human | 77 | >1000 | 0.06 | |
| PP$_{2-36}$, human | >40 | >100 | 0.06 | new peptide |
| PP$_{13-36}$, human | >100 | >100 | 39 | new peptide |
| PP$_{20-36}$, human | >100 | >100 | >100 | new peptide |
| PP$_{27-36}$, human | >100 | >100 | >88 | new peptide |
| PP$_{31-36}$, human | >10000 | >10000 | 350 | new peptide |
| PP$_{31-36}$ free acid, human | >10000 | >10000 | >10000 | new peptide |
| Phe-Met-Arg-Phe-Amide | 12000 | 75000 | 4000 | |
| Phe-Leu-Arg-Phe-Amide | 15000 | >100000 | 750 | new peptide |
| [Ile$^{31}$,Gln$^{34}$]PP, human | >86 | 20 | 0.09 | new peptide |
| PP, bovine | 240 | >820 | 0.05 | new peptide |
| PP, rat | 460 | >1000 | 0.18 | new peptide |
| PP, salmon | 0.20 | 0.17 | 3.2 | new peptide |
| PP, avian | 400 | >1000 | 7.0 | new peptide |
| PP, frog | 98 | >1000 | 61 | new peptide |
| PYY, human | 0.19 | 0.36 | 0.87 | |
| PYY, porcine | 0.14 | 0.35 | 1.3 | new peptide |
| PYY$_{3-36}$, human | 45 | 0.70 | 14 | new peptide |
| PYY$_{13-36}$, porcine | 33 | 1.5 | 46 | |
| [Pro$^{34}$]PYY, human | 0.14 | >310 | 0.12 | new peptide |
| Peptide | Y1 | Y2 | Y4 | Notes |
| NPY, human | 0.08 | 0.74 | 2.2 | |
| NPY, porcine | 0.07 | 0.81 | 1.1 | |
| Melanostatin (frog NPY) | 0.07 | 0.87 | 1.2 | new peptide |
| NPY$_{2-36}$, human | 3.6 | 2.0 | 16 | new peptide |
| NPY$_{2-36}$, porcine | 2.4 | 1.2 | 5.6 | |
| NPY$_{13-36}$, porcine | 70 | 2.5 | 38 | |
| Peptide | Y1 | Y2 | Y4 | Comments |
| NPY$_{16-36}$, porcine | 41 | 3.6 | 54 | |
| NPY$_{18-36}$, porcine | 70 | 4.2 | >290 | |
| NPY$_{20-36}$, porcine | 63 | 3.6 | 120 | |
| NPY$_{22-36}$, porcine | >1000 | 18 | >990 | |
| NPY$_{26-36}$, porcine | >1000 | 380 | 304 | |
| [Leu$^{31}$, Pro$^{34}$]NPY, human | 0.15 | >120 | 1.1 | |
| [Leu$^{31}$, Pro$^{34}$]NPY, porcine | 0.15 | >540 | 1.5 | new peptide |
| O-Me-Tyr$^{21}$-NPY, human | 0.12 | 1.55 | 6.1 | new peptide |
| NPY free acid, human | 490 | >1000 | >1000 | |
| NPY$_{1-24}$ amide, human | >1000 | >1000 | >1000 | new peptide |
| C2-NPY, porcine | 73 | 3.5 | 120 | new peptide |
| [D-Trp$^{32}$]NPY, human | >1000 | >1000 | >1000 | new peptide |

TABLE 4: Functional activation of the human Y4 receptor and inhibition of cAMP accumulation.

$K_i$ values were derived from binding assays as described in Table 3. Peptides were evaluated for binding affinity and then analyzed for functional activity. Functional data were derived from radioimmunoassay of cAMP accumulation in stably transfected LM(tk-) cells stimulated with 10 μM forskolin. The maximum inhibition of cAMP accumulation relative to that produced by human PP ($E_{max}$) and the concentration producing a half-maximal effect ($EC_{50}$) were determined by nonlinear regression.

TABLE 4

| | Binding | Function | |
|---|---|---|---|
| Peptide | $K_i$ (nM) | $EC_{50}$ (nM) | $E_{max}$ |
| PP, human | 0.06 | 0.09 | 100% |
| PP$_{2-36}$, human | 0.06 | 0.08 | 101% |
| PP$_{13-36}$, human | 39 | 580 | 96% |
| PP$_{27-36}$, human | >88 | 3500 | 50% |
| PP$_{31-36}$, human | >10000 | 89000 | 47% |
| [Ile$^{31}$,Gln$^{34}$]PP, human | 0.09 | 0.27 | 101% |
| salmon PP | 3.2 | 110 | 96% |
| PYY, human | 0.87 | 47 | 118% |
| [Pro$^{34}$]PYY, human | 0.12 | 1.1 | 106% |
| NPY, human | 2.2 | 20 | 98% |
| NPY, porcine | 1.1 | 68 | 105% |

TABLE 4-continued

| Peptide | Binding K$_i$ (nM) | Function EC$_{50}$ (nM) | E$_{max}$ |
|---|---|---|---|
| NPY$_{18-36}$ | >290 | Not detected | |
| [Leu$^{31}$,Pro$^{34}$]NPY human | 1.1 | 35 | 105% |
| [Leu$^{31}$,Pro$^{34}$]NPY,porcine | 1.5 | 26 | 111% |
| [D-Trp$^{32}$]NPY, human | >1000 | Not detected | |

TABLE 5: Macrolocalization of Y4 receptor mRNA in human tissues by PCR.

Localization data reflect PCR-based amplification of human Y4 cDNA derived from mRNA extracts of human tissues. Southern blots of the PCR products were prepared and hybridized with $^{32}$P-labeled oligonucleotide probes selective for Y-type receptor subtypes. The labeled products were recorded on X-ray film and the relative signal density was determined by visual inspection. In this rating scheme, +=faint signal, ++=moderate signal, +++=intense signal.

TABLE 5

| Human tissues | human Y4 PCR product |
|---|---|
| total brain | +++ |
| frontal brain | + |
| ventricle (heart) | ++ |
| atrium (heart) | + |
| thoracic aorta | ++ |
| coronary artery | +++ |
| nasal mucosa | + |
| mesentery | ++ |
| stomach | ++ |
| ileum | +++ |
| pancreas | not determined |
| liver | (−) |
| kidney | not determined |
| bladder | + |
| penis | + |
| testes | + |
| uterus (endometrium) | ++ |
| uterus (myometrium) | + |

TABLE 6: Pharmacological binding profile of the rat Y4 receptor vs. the human Y4 receptor.

Binding data reflect competitive displacement of $^{125}$I-PYY from membranes of COS-7 cells transiently expressing rat Y4 and human Y4 receptors. IC$_{50}$ values corresponding to 50% displacement were determined by nonlinear regression analysis and converted to K$_i$ values according to the equation Chang-Prusoff equation, K$_i$=IC$_{50}$/(1+[L]/K$_d$), where [L] is the $^{125}$I-PYY concentration and K$_d$ is the equilibrium dissociation constant of $^{125}$I-PYY.

TABLE 6

| Peptide | Rat Y4 | Human Y4 |
|---|---|---|
| PP, human | 0.12 | 0.06 |
| PP, rat | 0.20 | 0.18 |
| PP, bovine | 0.15 | 0.05 |
| PP, frog | 0.19 | 62 |
| PP, salmon | 0.36 | 3.2 |
| PP$_{31-36}$, human | 20 | 350 |

TABLE 6-continued

| Peptide | Rat Y4 | Human Y4 |
|---|---|---|
| PP, avian | >82 | 7 |
| PP$_{31-36}$ free acid, human | >100 | >10000 |
| PYY, porcine | 0.58 | 1.3 |
| NPY, human | 1.7 | 2.2 |
| NPY, porcine | 1.8 | 1.1 |
| NPY$_{2-36}$, human | 5 | 16 |
| NPY$_{13-36}$, porcine | 135 | 38 |
| [Leu$^{31}$,Pro$^{34}$]NPY, human | 0.59 | 1.2 |
| NPY free acid, human | >1000 | >1000 |
| C2-NPY, porcine | 22 | 120 |
| [D-Trp32]NPY, human | >1000 | >1000 |

Discussion

Applicants have cloned DNA representing a novel human neuropeptide Y/peptide YY/pancreatic polypeptide receptor (Y4) from human genomic DNA. Of all known G protein-coupled receptor sequences (EMBL/Genbank Data Base), the greatest homology was displayed between hp25a and the Y1 receptor genes (mouse—Eva et al., 1992; rat—Eva et al., 1990; and human—Larhammar et al., 1992). Comparison of the human hp25a deduced amino acid sequence with known G protein-coupled receptor sequences indicates the greatest concentration of identical amino acids to be in the transmembrane domains. In these TM regions, the percentage of identity for hp25a clone is 55% compared to human Y1, and less than 35% with other members of the peptide subfamily and other G protein-coupled receptor subfamilies. The alignment of this human hp25a sequence, relative to other G protein-coupled receptors or other members of the neuropeptide receptor subfamily, specifically human Y1, indicates a unique sequence, proving hp25a is a newly characterized receptor. The homology of hp25a to Y1 indicates that it is related to the NPY/PYY/PP family of receptors.

While the hp25a human receptor sequence exhibits higher overall and transmembrane identity to the rs16b rat Y4 receptor sequence than to other Y-type receptors such as the human Y1 receptor, the divergence between the rat Y4 and human Y4 sequences may contribute to the pharmacological differences between the two receptors. The isolation of the rat homologue of the Y4 receptor provides the means to compare the pharmacological properties of the rat and human Y4 receptors (see below) in relation to their observed differences in primary structures. These data will be critical to the design and testing of human therapeutic agents acting at these sites.

The unique pharmacological profile of the hp25a human Y4 receptor suggests that this receptor can serve as a novel target for the development of subtype selective ligands. The competitive displacement studies indicate that human PP is the preferred ligand for hp25a. The receptor also binds with high affinity to human NPY and human PYY, which share ≧47% amino acid identity with human PP. Affinity is enhanced by modifying NPY to closely resemble PP, as in [Leu$^{31}$,Pro$^{34}$]NPY. Decreased affinity for C-terminal fragments of NPY suggest that both N- and C-terminal regions of NPY contribute to hp25a receptor recognition. hp25a was less sensitive to N-terminal deletion of NPY than was the human Y1 receptor. One may speculate that both Y1 and hp25a share a common mechanism of peptide interaction which has been optimized for either NPY or PP, respectively.

The pharmacological data do not support classification of hp25a as a Y1 receptor, in which case it would display >4000-fold selectivity for binding to human NPY over human PP (Table 2). Neither do the data support classification as a Y2 receptor, in which case it would tolerate N-terminal deletion of NPY but not exchange of $Gln^{34}$ for $Pro^{34}$ (Table 2). Finally, the data fails to support the classification of hp25a as a Y3 receptor, since it would be expected to display greater affinity for NPY than for PP or PYY (Wahlestedt et al., 1991). Therefore, applicants are designating the hp25a receptor as a Y4 receptor.

The additional data included here reflect an increased understanding of receptor ligand/interactions. Our further characterization of Y4 receptor pharmacology has indicated, for example, that the binding affinity for either human NPY ($K_i$=2.2 nM) or human PYY ($_i$=0.87 nM) can be enhanced by conversion to human $[^{LEG}, Pro^{34}]$NPY ($K_i$=1.1. nM) or human $[Pro^{34}]$PYY ($K_i$=0.14 nM). This information supports the importance of Pro34- in the peptide pharmacophore and could potentially be incorporated into the design of metabolically stable nonpeptide ligands with Y4-selectivity. Additionally, the data prompt a re-evaluation of literature reports in which $[Pro^{34}]$PYY is described as a Y1-selective ligand. Our results indicate that $[Pro^{34}]$PYY does not discriminate between the cloned human Y1 and cloned human Y4 receptor ($K_i$=0.12 and 0.14 nM, respectively) such that $[Pro^{34}]$PYY cannot be used in isolation to define receptor subtypes.

Other particularly interesting peptides include FMRF-amide, FLRF-amide, and $[D-Trp^{32}]$NPY. FMRF-amide and $[D-Trp^{32}]$NPY have both been shown to modulate food intake in rats (get ref from George M). While FMRF-amide and its derivative displayed some degree of Y4-selectivity (albeit relatively low affinity compared to human PP), $[D-Trp^{32}]$NPY was essentially inactive at all Y-receptor subtypes studied. These profiles must be considered as efforts are undertaken to validate the receptor mechanism of NPY-induced food intake. The tetrapeptide FLRF-amide has additional value as a starting point for the design of small nonpeptide compounds with Y4 selectivity.

Applicants now have several Y4 receptor expression systems from which to chose, each uniquely suited to different research questions. The transient expression system in COS-7, for example, allows one to generate sufficient quantities of membranes for routine structure/activity relationship questions. Applicants can also produce mutant receptors by site-directed mutagenesis or other mutagenesis techniques and express them transiently in COS-7 for a comparison of pharmacological properties with those of the wild-type receptor. In this way, one can gain insight into receptor binding pockets, ligand binding domains, and mechanisms of activation. Whereas the transient expression system requires a new transfection for every cell or membrane harvest, the stable expression system offers the convenience of a single transfection step followed by routine passaging techniques. The stable system also offers the opportunity to select receptor density, which could be an important factor in evaluating the intrinsic activity of Y4 receptor ligands.

Applicants' characterization of the stably expressed Y4 receptor now shows definitively that the Y4 receptor can couple simultaneously to both cAMP regulation and calcium mobilization in a single cell type. The $EC_{50}$ for the calcium response is significantly higher than the $EC_{50}$ for the cAMP response, suggesting that calcium mobilization may reflect promiscuous coupling of the receptor to G-protein other than that required for cyclase regulation. The functional assays allow one to assign agonist and antagonist activities to receptor selective compounds and thereby provide one with critical tools for drug design.

The question logically arises as to whether hp25a should be classified as a PP receptor. To applicants' knowledge, no human PP receptor has been described. One must therefore look to the rat PP receptor for comparison. The rat PP receptor bound PP and analogs in the same rank order as hp25a (PP>$[Leu^{31}, Pro^{34}]$NPY>NPY) (Schwartz et al., 1990). The rat PP receptor also appeared to bind both N- and C-terminal regions of the peptide ligand (Schwartz et al., 1987). A glaring discrepancy between hp25a and the rat PP receptor is that the latter displayed >10,000-fold selectivity for PP over NPY (Schwartz et al., 1990).

In applicants' localization experiments Y4 mRNA was detected by PCR techniques in a broad range of human tissues. Relatively intense hybridization signals were detected in total brain, coronary artery, and ileum, suggesting a potential role for Y4 receptors in CNS function, cardiovascular regulation, and gastrointestinal physiology. This localization pattern is consistent with previously reported studies of PP-mediated effects at 1) brainstem sites (McTigue et al., 1993; Whitcomb et al., 1990), 2) on arterial blood pressure (Wager-Page et al., 1993a) and 3) on gastric acid secretion and gastrointestinal motility (McTigue et al, 1993; Wager-Page et al, 1993b. A more definitive localization of the Y4 receptor mRNA and receptor expression (i.e., whether on enterocytes, vascular smooth muscle cells, neurons, etc.) is attainable through in situ hybridization and receptor autoradiography techniques. There are to applicants' knowledge no published reports of PP receptor localization in human tissue as obtained through binding or functional studies. It may be informative, however, to compare the human Y4 macrolocalization data presented here with PP receptor characterization in the rat. PP receptors have been described, for example, in brainstem nuclei such as the area postrema, interpeduncular nucleus, dorsomedial nucleus, and the nucleus tractus solitarius (Whitcomb et al., 1990), consistent with the identification of Y4 mRNA in human brain. The PP receptors in rat brain stem are accessible to circulating PP, which is released upon vagal stimulation of the pancreas during feeding (Whitcomb et al., 1990). Activation of brainstem PP receptors inhibits further pancreatic secretion, increases gastric acid secretion, enhances gastric motility, and increases gastric emptying time (Louie et al., 1985; McTigue and Rogers, 1993). A Y4 receptor antagonist then, would be expected to slow down gastric emptying time and potentially reduce meal size.

Given the similarities in pharmacologic profiles between the published PP receptor and the hp25a human Y4 receptor, it would be tempting to call hp25a the human PP receptor. Applicants believe that calling hp25a the human PP receptor, however, would be misleading. This is because the relatively compressed window of affinity for PP, PYY, and NPY (0.02 nM$\leq K_i \leq$1.5 nM) makes hp25a a potential target for all three peptide ligands. Future localization experiments may help resolve the relationship between hp25a and the PP receptor.

Applicants propose that hp25a be known as the Y4 receptor. The name is not biased toward any one member of the pancreatic polypeptide family. The "Y" has its roots in the original classification of Y1 and Y2 receptor subtypes (Wahlestedt et al., 1987). The letter reflects the conservation in pancreatic polypeptide family members of the C-terminal tyrosine, described as "Y" in the single letter amino acid code. Applicants note that the cloned human Y1 receptor was introduced by Larhammar and co-workers as a "human neuropeptide Y/peptide YY receptor of the Y1 type", with peptide ligands listed in rank order of affinity (Larhammar et al., 1992). Similarly, hp25a could be described as a human pancreatic polypeptide/peptide YY/neuropeptide Y receptor of the Y4 type.

hp25a is to applicants' knowledge the first "Y type" receptor to be cloned from a subtype family other than Y1. The reported Y3 receptor cloned from bovine brain (Rimland et al., 1991) was later described as having been misidentified (Jazin et al., 1993; Herzog et al., 1993). A Y2-like receptor (PR4) was cloned from drosophila and characterized using mammalian analogs of NPY (Li et al., 1992); however, the classification of this receptor is controversial. The receptor was relatively insensitive to NPY; concentrations ranging from 0.3 to 10 $\mu$M were required to elicit calcium mobilization in oocytes injected with PR4 mRNA (Li et al., 1992). The receptor also displayed a rank order of potency for NPY analogs distinct from that observed in mammalian systems (Wahlestedt et al., 1993; Li et al., 1992). Furthermore, an NPY analog has not been isolated from drosophila (Wahlestedt et al., 1993). It is possible that an unidentified ligand in drosophila can activate PR4 more readily than NPY, and as such, the receptor may eventually be reclassified.

The cloning and expression of a Y4 (hp25a) receptor represents a major advance in the ability to analyze numerous physiological processes mediated by the pancreatic polypeptide family. Binding sites for PP, PYY, or NPY have a widespread anatomical distribution in peripheral targets such as neuromuscular junction, smooth muscle, stomach chief cells, intestinal enterocytes, kidney proximal tubule, and fat cells (Dumont et al., 1992; Castan et al., 1992). These receptors are therefore in a position to potentially regulate a variety of physiological functions including cognition, circadian rhythm, EEG synchronization, body temperature, blood pressure, locomotor activity, neuroendocrine release, sexual/reproductive behavior, feeding, sympathetic activation, sensory transmission, gastrointestinal function, intestinal secretion, renal absorption, and cardiovascular function (Wahlestedt et al., 1993).

Y4 receptors are an invaluable resource for drug design. The pancreatic polypeptide family is potentially involved in several pathophysiological conditions including memory loss, depression, anxiety, epileptic seizure, pain, hypertension, locomotor problems, circadian rhythm disorders, eating/body weight disorders, sexual/reproductive disorders, nasal congestion, and diarrhea (Wahlestedt et al., 1993; Dumont et al., 1992). The available data implicate this receptor in the control of obesity and other disorders of feeding including bulimia and anorexia. The chemical synthesis of selective drugs not only for Y4 but for all "Y type" receptors will be greatly accelerated by preliminary screening against a homogeneous population of cloned human Y4 receptors. As more specific pharmacological tools become available for probing receptor function, additional therapeutic indications are likely to be discovered.

Applicants do not know whether hp25a represents the single Y4 receptor expressed in the human genome, or whether there exists a group of structurally related Y4 receptor subtypes. This is an issue which can be resolved using nucleotide sequences from Y4 receptor as the basis for in situ localization, antisense or "knockout" strategies, homology cloning, and related techniques. Such approaches will enable one to investigate the existence of potentially novel receptor subtypes with pharmacologic and therapeutic significance.

In conclusion, the primary structure of the proteins encoded by hp25a (Y4) gene and its homolog in the rat, as well as its unique pharmacological profile obtained for the Y4 receptor subtype, indicate that these genes represent a new pancreatic polypeptide receptor subfamily. Additional cloning efforts will be required to isolate additional members of this newly recognized neuropeptide receptor family.

REFERENCES

Aakerlund, L., U. Gether, J. Fuhlendorff, T. W. Schwartz, and O. Thastrup. Y1 receptors for neuropeptide Y are coupled to mobilization of intracellular calcium and inhibition of adenylate cyclase. FEBS Lett. 260:73–78 (1990).

Alumets, J., R. Hakanson, and F. Sundler. Distribution, ontogeny and ultrastructure of pancreatic polypeptide (PP) cells in pancreas and gut of the chicken. Cell. Tissue Res. 194:377–386 (1978).

Balasubramaniam, A., Sheriff, S., Johnson, M. E., Prabhakaran, M., Huang, Y., Fischer, J. E., and Chance, W. T. [D-Trp$^{32}$]Neuropeptide Y: A competitive antagonist of NPY in rat hypothalamus. J. Med. Chem. 37: 811–815 (1994).

Beck, A. G., G. Jung, W. Gaida, H. Koppen, R. Lang, and G. Schnorrenberg. Highly potent and small neuropeptide Y agonist obtained by linking NPY$_{1-4}$ via a spacer to alpha-helical NPY$_{25-36}$. FEBS Lett. 244: 119–122 (1989).

Beck-Sickinger, A. G., W. Gaida, G. Schnorrenberg, R. Lang, and G. Jung. Neuropeptide Y: Identification of the binding site. Int. J. Peptide Protein Res. 36: 522–530 (1990).

Bottcher, G., K. Sjolund, E. Ekblad, R. Hakanson, T. W. Schwartz, and F. Sundler. Co-existence of peptide YY in glicentin immunoreactivity in endocrine cells of the gut. Regul. Pept. 8:261–273 (1984).

Bradford, M. M. A rapid and sensitive method for the quantitation of microgram quantities of protein utilizing the principle of protein-dye binding. Anal. Biochem. 72: 248–254 (1976).

Branchek, T., N. Adham, M. Macchi, H.-T. Kao, and P. R. Hartig. [$^3$H]-DOB (4-bromo-2,5-dimethoxyphenylisopropylamine) and [$^3$H]ketanserin label two affinity states of the cloned human 5-hydroxytryptamine$_2$ receptor. Mol. Pharmacol. 38:604–609 (1990).

Castan, I., P. Valet, T. Voisin, N. Quideau, M. Laburthe, and M. Lafontan. Identification and functional studies of a specific peptide YY-preferring receptor in dog adipocytes. Endocrinology 131: 1970–1976 (1992).

Clark, J. T., P. S. Kalra, and S. P. Kalra. Neuropeptide Y stimulates feeding but inhibits sexual behavior in rats. Endocrinology 117: 2435–2442 (1985).

De Wied, D. In: Neuropeptides: Basics and Perspectives (Elsevier, Amsterdam-New York-Oxford), 1990.

Heilig, M. and E. Widerlov. Neuropeptide Y: an overview of central distribution, functional aspects, and possible involvement of neuropsychiatric illnesses. Acta Psychiatr. Scand. 82:95–114 (1990).

Di Maggio, D. A., B. M. Chronwall, K. Buchman, and T. L. O'Donohue. Pancreatic polypeptide immunoreactivity in rat brain is actually neuropeptide Y. Neuroscience 15:1149–1157 (1985).

Dumont, Y., J.-C. Martel, A. Fournier, S. St.-Pierre, and R. Quiron. Neuropeptide Y and neuropeptide Y receptor subtypes in brain and peripheral tissues. Prog. Neurobiol. 38:125–167 (1992).

Eva, C., A. Oberto, R. Sprengel, and E. Genazzani. The murine NPY-1 receptor gene: structure and delineation of tissue specific expression. FEBS Lett. 314:285–288 (1992).

Eva, C., K. Keinanen, H. Monyer, P. Seeburg, and R. Sprengel. Molecular cloning of a novel G protein-coupled receptor that may belong to the neuropeptide receptor family. FEBS Lett. 271:80–84 (1990).

Fuhlendorff, J., N. Langeland Johansen, S. G. Melberg, H. Thogersen, and T. W. Schwartz. The antiparallel pancreatic polypeptide fold in the binding of neuropeptide Y to Y1 and Y2 receptors. J. Biol. Chem. 265:11706–11712 (1990).

Fuhlendorff, J., U. Gether, L. Aakerlund, N. Langeland-Johansen, H. Thogersen, S. G. Melberg, U. B. Olsen, O. Thastrup, and T. W. Schwartz. [Leu$^{31}$,Pro$^{34}$]Neuropeptide Y: A specific $Y_1$ receptor agonist. Proc. Natl. Acad. Sci. USA 87: 182–186 (1990).

Glover, I. D., D. J. Barlow, J. E. Pitts, S. P. Wood, I. J. Tickle, T. L. Blundell, K. Tatemoto, J. R. Kimmel, A. Wollmer, W. Strassburger, and Y.-S. Zhang. Conformational studies of the pancreatic polypeptide hormone family. Eur. J. Biochem. 142:379–385 (1985).

Grundemar, L., S. P. Sheikh, and C. Wahlestedt, In: The Biology of Neuropeptide Y and Related Peptides. (Humana Press, Inc., Totawa, N.J.), (1992).

Grundemar, L., J. L. Krstenansky, and R. Hakanson. Activation of neuropeptide Y1 and neuropeptide Y2 receptors by substituted and truncated neuropeptide Y analogs: identification of signal epitopes. Eur. J. Pharmacol. 232: 271–278 (1992).

Herzog, H., Y. J. Hort, H. J. Ball, G. Hayes, J. Shine, and L. Selbie. Cloned human neuropeptide Y receptor couples to two different second messenger systems. Proc. Natl. Acad. Sci. USA 89: 5794–5798 (1992).

Herzog, H., Y. J. Hort, J. Shine, and L. A. Selbie. Molecular Cloning, Characterization, and localization of the human homolog to the reported bovine NPY Y3 receptor: lack of NPY binding and activation. DNA and Cell Biology 12: 465–471 (1993).

Hinson, J., C. Rauh, and J. Coupet. Neuropeptide Y stimulates inositol phospholipid hydrolysis in rat brain microprisms. Brain Res. 446:379–382 (1988).

Inui, A., M. Okita, M. Miura, Y. Hirosue, M. Nakajima, T. Inoue, and S. Baba. Characterization of the receptor for peptide-YY and avian pancreatic polypeptide in chicken and pig brains. Endocrinology 127:934–941 (1990).

Jazin, E. E., Yoo, H., Blomqvist, A. G., Yee, F., Weng, G., Walker, M. W., Salon, J., Larhammar, D., and Wahlestedt, C. A proposed bovine neuropeptide Y (NPY) receptor cDNA clone, or its human homologue, confers neither NPY binding sites nor NPY responsiveness on transfected cells. Reg. Peptides 47: 247–258 (1993).

Jorgensen, J. C., J. Fuhlendorff, and T. W. Schwartz. Structure/function studies on neuropeptide Y and pancreatic polypeptide evidence for two PP-fold receptors in vas deferens. Eur. J. Pharmac. 186: 105–114 (1990).

Kingston, R. E., in Current Protocols in Molecular Biology, 1: 4.2.1–4.2.4 (John Wiley and Sons, N.Y.), 1987.

Laburthe, M. Peptide YY and neuropeptide Y in the gut: Availability, biological actions, and receptors. Trends Endocrinol. Metab. 1:168–174 (1990).

Laburthe, M., B. Chenut, C. Rouyer-Fessard, K. Tatemoto, A. Couvineau, A. Servin, and B. Amiranoff. Interaction of peptide YY with rat intestinal epithelial plasma membranes: binding of the radioiodinated peptide. Endocrinology 118:1910–1917 (1986).

Larhammar, D. G., A. G. Blomqvist, F. Yee, E. E. Jazin, H. Yoo, and C. R. Wahlestedt. Cloning and functional expression of a human neuropeptide Y/peptide YY receptor of the Y1 type. J. Biol. Chem. 267:10935–10938 (1992).

Li, X.-J., Y.-N. Wu, R. A. North, and M. Forte. Cloning, functional expression, and developmental regulation of a neuropeptide Y receptor from drosophila melanogaster. J. Biol. Chem. 267: 9–12 (1992).

Lopata, M. A., Cleveland, D. W., and Sollner-Webb, B. (1984). Nucl. Acids Res. 12:5707–5717.

Louie, D. S., Williams, J. A., and Owyang, C. (1985). Action of pancreatic polypeptide on rat pancreatic secretion: in vivo and in vitro. Am. J. Physiol. 249: G489–G495.

Lundberg, J. M., A. Hemsen, O. Larsson, A. Rudehill, A. Saria, and B. Fredholm. Neuropeptide Y receptor in pig spleen: binding characteristics, reduction of cyclic AMP formation and calcium antagonist inhibition of vasoconstriction. Eur. J. Pharmacol. 145:21–29 (1988).

McTigue, D. M., Edwards, N. K., and Rogers, R. C. (1993) Pancreatic polypeptide in dorsal vagal complex stimulates gastric acid secretion and motility in rats. Am. J. Physiol. 26S: G1169–G1176.

Mihara, S., Y. Shigeri, and M. Fujimoto. Neuropeptide Y-induced intracellular $Ca^{2+}$ increase in vascular smooth muscle cells. FEBS Lett. 259:79–82 (1989)

Miller, J., and R. N. Germain. Efficient cell surface expression of class II MHC molecules in the absence of associated invariant chain. J.Exp.Med. 164:1478–1489 (1986).

Rimland, J., W. Xin, P. Sweetnam, K. Saijoh, E. J. Nestler, and R. S. Duman. Sequence and expression of a neuropeptide Y receptor cDNA. Mol. Pharmacol. 40: 869–875 (1991).

Robert, J. J., Orosco, M., Rouch, C., Jacquot, C., and Cohen, Y. (1988) Unexpected Responses of the Obese "Cafeteria" Rat to the Peptide FMRF-Amide. Pharm., Biochem. and Behavior, 34:341–344.

Sambrook, J., Fritsch, E. F., and Maniatis, T., In: Molecular Cloning: A Laboratory Manual, 2nd Edition (Cold Spring Harbor Laboratory, Cold Spring Harbor, N.Y.), 1989.

Sanger, F., Nicklen, S. and Coulsen, A. R. Proc. Natl. Acad. Sci. USA 74:5463–5467 (1977).

Schwartz, T. W., S. P. Sheikh, and M. M. I. O'Hare. Receptors on pheochromocytoma cells for two members of the PP-fold family—NPY and PP. FEBS Lett. 225:209–214 (1987).

Schwartz, T. W. Pancreatic polypeptide a hormone under vagal control. Gastroenterology 85:1411–1425 (1983).

Schwartz, T. W., J. Fuhlendorff, L. L. Kjems, M. S. Kristensen, M. Vervelde, M. O'Hare, J. L. Krstenansky, and B. Bjornholm. Signal epitopes in the three-dimensional structure of neuropeptide Y. Ann. N.Y. Acad. Sci. 611: 35–47 (1990).

Southern, E. M. Detection of specific sequences among DNA fragments separated by gel electrophoresis. J. Mol. Biol. 98:503–517 (1975).

Stanley, B. G., D. R. Daniel, A. S. Chin, and S. F. Leibowitz. Paraventricular nucleus injections of peptide YY and neuropeptide Y preferentially enhance carbohydrate ingestion. Peptides. 6: 1205–1211 (1985). Stanley, B. G., W. Magdalin, A. Seirafi, M. M. Nguyen, and S. F. Leibowitz. Evidence for neuropeptide Y mediation of eating produced by food deprivation and for a variant of the $Y_1$ receptor mediating this peptide's effect. Peptides 13: 581–587 (1992).

Voisin, T., M. Bens, F. Cluzeaud, A. Vandewalle, and M. Laburthe. Peptide YY receptors in the proximal tubule PKSV-PCT cell line derived from transgenic mice: relation with cell growth. J. Biol. Chem. 268:20547–20554 (1993).

Wager-Page, S. A., Rosenbaum, G., Veale, W. L., and Davison, J. S. (1993a) Spinal and peripheral modulation of gastric acid secretion and arterial pressure by neuropeptide Y, peptide YY and pancreatic polypeptide in rats. Peptides 14: 1299–1308.

Wager-Page, S. A., Ghazali, B., Anderson, W., Veale, W. L., and Davison, J. S. (1993b). Neuropeptide Y, peptide YY, and pancreatic polypeptide modulate duodenal and colonic motility at a thoracic spinal site in rats. Peptides 13: 807–813.

Wahlestedt, C., and D. J. Reis. Neuropeptide Y-Related Peptides and Their Receptors—Are the Receptors Potential Therapeutic Targets? Ann. Rev. Pharmacol. Tox. 32: 309–352. (1993).

Wahlestedt, C., N. Yanaihara, and R. Hakanson. Evidence for different pre- and postjunctional receptors for neuropeptide Y and related peptides. Regul. Pept. 13:307–318 (1986).

Wahlestedt, C., Regunathan, S., and D. J. Reis. Identification of cultured cells selectively expressing Y1-, Y2-, or Y3-type receptors for neuropeptide Y/peptide YY. Life Sciences 50: PL-7–PL-12 (1991).

Wahlestedt, C., L. Edvinsson, E. Ekblad, and R. Hakanson. Effects of neuropeptide Y at sympathetic neuroeffector junctions: Existence of Y1 and Y2 receptors. In: Neuronal messengers in vascular function, Fernstrom Symp. No 10., pp. 231–242. Eds A. Nobin and C. H. Owman. Elsevier: Amsterdam (1987).

Whitcomb, D. C., I. L. Taylor, and S. R. Vigna. Characterization of saturable binding sites for circulating pancreatic polypeptide in rat brain. Am. J. Physiol. 259: G687-G691 (1990).

What is claimed is:

1. A process for determining whether a chemical compound specifically binds to and activates a human or a rat Y4 receptor, which comprises contacting nonneuronal cells producing a second messenger response and expressing on their cell surface a human or a rat Y4 receptor, with the chemical compound under conditions suitable for activation of the human or the rat Y4 receptor, and measuring the second messenger response in the presence and in the absence of the chemical compound, a change in second messenger response in the presence of the chemical compound indicating that the chemical compound activates the human or the rat Y4 receptor, wherein the human Y4 receptor has an amino acid sequence as shown in SEQ ID NO: 2 and the rat Y4 receptor has an amino acid sequence as shown in SEQ ID NO: 28.

2. A process for determining whether a chemical compound specifically binds to and activates a human or rat Y4 receptor, which comprises contacting a membrane fraction from nonneuronal cells producing a second messenger response and expressing on their cell surface a human or rat Y4 receptor, with the chemical compound under conditions suitable for activation of the human or rat Y4 receptor, and measuring the second messenger response in the presence and in the absence of the chemical compound, a change in second messenger response in the presence of the chemical compound indicating that the chemical compound activates the human or rat Y4 receptor, wherein the human Y4 receptor has an amino acid sequence as shown in SEQ ID NO: 2 and the rat Y4 receptor has an amino acid sequence as shown in SEQ ID NO: 28.

3. A process for determining whether a chemical compound specifically binds to and inhibits activation of a human or rat Y4 receptor, which comprises separately contacting nonneuronal cells producing a second messenger response and expressing on their cell surface a human or rat Y4 receptor, with both the chemical compound and a second chemical compound known to activate the human or rat Y4 receptor, and with only the second chemical compound, under conditions suitable for activation of the human or rat Y4 receptor, and measuring the second messenger response in the presence of only the second chemical compound and in the presence of both the second chemical compound and the chemical compound, a smaller change in second messenger response in the presence of both the chemical compound and the second chemical compound than in the presence of only the second chemical compound indicating that the chemical compound inhibits activation of the human or rat Y4 receptor, wherein the human Y4 receptor has an amino acid sequence as shown in SEQ ID NO: 2 and the rat Y4 receptor has an amino acid sequence as shown in SEQ ID NO: 28.

4. A process for determining whether a chemical compound specifically binds to and inhibits activation of a human or rat Y4 receptor, which comprises separately contacting a membrane fraction from nonneuronal cells producing a second messenger response and expressing on their cell surface a human or rat Y4 receptor, with both the chemical compound and a second chemical compound known to activate the human or rat Y4 receptor, and with only the second chemical compound, under conditions suitable for activation of the human or rat Y4 receptor, and measuring the second messenger response in the presence of only the second chemical compound and in the presence of both the second chemical compound and the chemical compound, a smaller change in second messenger response in the presence of both the chemical compound and the second chemical compound than in the presence of only the second chemical compound indicating that the chemical compound inhibits activation of the human or rat Y4 receptor, wherein the human Y4 receptor has an amino acid sequence as shown in SEQ ID NO: 2 and the rat Y4 receptor has an amino acid sequence as shown in SEQ ID NO: 28.

5. The process of claim 1 or 2, wherein the second messenger response comprises cAMP accumulation and the change in second messenger response is a reduction in cAMP accumulation.

6. The process of claim 3 or 4, wherein the second messenger response comprises cAMP accumulation and the change in second messenger response is a smaller reduction in cAMP accumulation in the presence of both the chemical compound and the second chemical compound than in the presence of only the second chemical compound.

7. The process of claim 1, wherein the second messenger response comprises intracellular calcium levels and the change in second messenger response is an increase in intracellular calcium levels.

8. The process of claim 3, wherein the second messenger response comprises intracellular calcium levels and the change in second messenger response is a smaller increase in the level of intracellular calcium in the presence of both the chemical compound and the second chemical compound than in the presence of only the second chemical compound.

9. The process of any one of claims 1, 2, 3, or 4, wherein the cell is a mammalian cell.

10. The process of claim 9, wherein the mammalian cell is a COS-7 cell, a CHO cell, a LM(tk−) cell, a Y1 murine adrenal cell, or a NIH 3T3 cell.

* * * * *